US009580728B2

(12) United States Patent
Kallas et al.

(10) Patent No.: US 9,580,728 B2
(45) Date of Patent: Feb. 28, 2017

(54) METHODS FOR ISOPRENE AND PINENE PRODUCTION IN CYANOBACTERIA

(71) Applicant: WiSys Technology Foundation, Inc., Madison, WI (US)

(72) Inventors: Toivo Kallas, Oshkosh, WI (US); Matthew Nelson, Oshkosh, WI (US); Eric Singsaas, Stevens Point, WI (US)

(73) Assignee: WISYS TECHNOLOGY FOUNDATION, INC., Madison, WI (US)

( * ) Notice: Subject to any disclaimer, the term of this patent is extended or adjusted under 35 U.S.C. 154(b) by 0 days.

(21) Appl. No.: 15/156,557

(22) Filed: May 17, 2016

(65) Prior Publication Data

US 2017/0009260 A1 Jan. 12, 2017

Related U.S. Application Data

(62) Division of application No. 13/952,071, filed on Jul. 26, 2013.

(60) Provisional application No. 61/676,552, filed on Jul. 27, 2012.

(51) Int. Cl.
*C12P 5/02* (2006.01)
*C12P 5/00* (2006.01)

(52) U.S. Cl.
CPC ....... *C12P 5/007* (2013.01); *C12Y 205/01001* (2013.01); *C12Y 402/03015* (2013.01)

(58) Field of Classification Search
CPC ................................ C12P 2/026; C12P 5/002
USPC ......................................................... 435/167
See application file for complete search history.

(56) References Cited

U.S. PATENT DOCUMENTS

| | | | | |
|---|---|---|---|---|
| 8,609,385 | B2 | 12/2013 | Anderson | |
| 8,715,973 | B1 | 5/2014 | Pfleger et al. | |
| 8,753,840 | B2 | 6/2014 | Vermaas | |
| 8,802,407 | B2 | 8/2014 | Melis et al. | |
| 2011/0039323 | A1* | 2/2011 | Singsaas ............. | C12N 9/1022 435/167 |

FOREIGN PATENT DOCUMENTS

| | | | |
|---|---|---|---|
| CN | 103215315 | A | 7/2013 |
| CN | 103789293 | A | 5/2014 |
| WO | 2008137092 | A2 | 11/2008 |
| WO | 2009132220 | A2 | 10/2009 |
| WO | 2013096683 | | 6/2013 |
| WO | 2014037050 | A1 | 3/2014 |

OTHER PUBLICATIONS

Bohlman, et al., Plant terpenoid synthases: molecular biology and phylogenetic analysis, Proceedings National Academy Science USA, 1998, 95:4126-33.

Carter et al., Monoterpene biosynthesis pathway construction in *Escherichia coli*, Phytochemistry, 64:425-33 (2003).

Clerico et al., Specialized techniques for site-directed mutagenesis in cyanobacteria, Methods in Mol. Biol. 362:155-171 (2007).

Keseler et al. (2013), "EcoCyc: fusing model organism databases with systems biology", Nucleic Acids Research 41: D605-12.

Dong et al., ApcD is necessary for efficient energy transfer from phycobilisomes to photosystem I and helps to prevent photoinhibition in the cyanobacterium *Synechococcus* sp. PCC 7002, Biochim Biophys Acta. Sep. 2009;1787 (9):1122-8.

Frigaard et al., Gene inactivation in the cyanobacterium *Synechococcus* sp. PCC 7002 and the green sulfur bacterium Chlorobium tepidum using in vitro-made DNA constructs and natural transformation, Methods Mol Biol. 2004;274:325-40.

Gambliel et al., Pinene cyclases I and II. Two enzymes from sage (*Salvia officinalis*) which catalyze stereospecific cyclizations of geranyl pyrophosphate to monoterpene olefins of opposite configuration, Journal Biological Chemistry, 1984, 259:740-8.

Harvey et al., High-density renewable fuels based on the selective dimerization of pinenes, Energy Fuels, 2010; 24:267-273.

Kroll et al., Plasmid addiction systems: perspectives and applications in biotechnology, Microb. Biotechnol. 3:634-657 (2010).

Kudla et al., Coding-sequence determinants of gene expression in *Escherichia coli*, Science. Apr. 10, 2009;324 (5924):255-8.

Lindberg et al., Engineering a platform for photosynthetic isoprene production in cyanobacteria, using Synechocystis as the model organism, Metab Eng. Jan. 2010;12(1):70-9.

Liu et al., Nickel-inducible lysis system in *Synechocystis* sp. PCC 6803, Proc. Natl. Acad. Sci. USA 106:21550-21544 (2009).

Lu, et al., Cloning and Functional Characterization of a β-Pinene Synthase from Artemisia annua That Shows a Circadian Pattern of Expression, Plant Physiology, 2002,130 (1): 477-486.

Ludwig, et al., *Synechococcus* sp. strain PCC 7002 transcriptome: acclimation to temperature, salinity, oxidative stress, and mixotrophic growth conditions, Frontiers Microbiology Oct. 2012, vol. 3, pp. 1-14.

Melis, Solar energy conversion efficiencies in photosynthesis: Minimizing the chlorophyll antennae to maximize efficiency, vol. 177, Issue 4, Oct. 2009, pp. 272-280.

Nomura et al., Roles for heme-copper oxidases in extreme high-light and oxidative stress response in the cyanobacterium *Synechococcus* sp. PCC 7002, Arch Microbiol. Jun. 2006;185(6):471-9.

Sasaki et al., Gene expression and characterization of isoprene synthase from Populus alba, FEBS Lett. Apr. 25, 2005;579(11):2514-8.

Silver et al., Characterization of aspen isoprene synthase, an enzyme responsible for leaf isoprene emission to the atmosphere, J Biol Chem. Jun. 2, 1995;270(22):13010-6.

(Continued)

*Primary Examiner* — Tekchand Saidha
(74) *Attorney, Agent, or Firm* — Quarles & Brady, LLP

(57) ABSTRACT

Methods of isoprenoid production are provided by the present invention. In particular, transgenic *Synechococcus* sp. PCC 7002 cyanobacteria and methods for producing isoprene and pinene using a host transgenic *Synechococcus* sp. PCC 7002 cyanobacterium are provided.

15 Claims, 22 Drawing Sheets
(20 of 22 Drawing Sheet(s) Filed in Color)

(56) References Cited

OTHER PUBLICATIONS

Takeshima et al., A novel expression vector for the cyanobacterium, Synechococcus PCC 6301, DNA Res. 1:181-189 (1994).

Van Baalen et al., Isolation and Growth of Psychrophilic Diatoms from the Ice-edge in the Bering Sea, Botanica Marina 4:129-139 (1962).

Wiberley et al., Regulation of isoprene emission from poplar leaves throughout a day, Plant Cell Environ. Jul. 2009;32(7):939-47.

Xu et al., Expression of Genes in Cyanobacteria: Adaptation of Endogenous Plasmids as PlaHorms for High-Level Gene Expression in *Synechococcus* sp. PCC 7002, Photosynth. Res. Protocols 684:273-293 (2010).

Xue et al., Enhancing isoprene production by genetic modification of the 1-deoxy-d-xylulose-5-phosphate pathway in Bacillus subtilis, Appl. Environ. Microbiol. 77:2399-2405 (2011).

Zhao et al., Biosynthesis of isoprene in *Escherichia coli* via methylerythritol phosphate (MEP) pathway, Applied Microbiology Biotechnology 90:1915 (2011).

Mark, Encyclopedia of Polymer Science and Technology (1967) vol. 7, pp. 782-854.

Quintana, et al., Renewable Energy from Cyanobacteria: Energy Production Optimization by Metabolic Pathway Engineering, Appl. Microbiol. Biotechnol., 2011, 91:471-490.

Ortiz, et al., Abstract: Investigation of Isoprene Synthase Protein Expression in *Synechococcus* sp. PCC 7002 by Liquid Chromatography Tandem-Mass Spectrometry (LC-MS/MS), Oct. 29, 2011, http://sacnas,confex.com/sacnas/2011/webprogram/Paper3987.html.

* cited by examiner

FIG. 5

EcoRI
GAATTCGTTATAAAATAAACTTAACAAATCTATACCCACCTGTAGAGAAGAGTCCCTGAAT

ATCAAAATGGTGGGATAAAAAGCTCAAAAAGGAAAGTAGGCTGTGGTTCCCTAGGCAACAG
TCTTCCCTACCCCACTGGAAACTAAAAAAACGAGAAAAGTTCGCACCGAACATCAATTGCA
TAATTTTAGCCCTAAAACATAAGCTGAACGAAACTGGTTGTCTTCCCTTCCCAATCCAGGA
CAATCTGAGAATCCCCTGCAACATTACTTAACAAAAAAGCAGGAATAAAATTAACAAGATG
TAACAGACATAAGTCCCATCACCGTTGTATAAAGTTAACTGTGGGATTGCAAAAGCATTCA
AGCCTAGGCGCTGAGCTGTTTGAGCATCCCGGTGGCCCTTGTCGCTGCCTCCGTGTTTCTC
CCTGGATTTATTTAGGTAATATCTCTCATAAATCCCCGGGTAGTTAACGAAAGTTAATGGA
GATCAGTAACAATAACTCTAGGGTCATTACTTTGGACTCCCTCAGTTTATCCGGGGGAATT

NdeI
GTGTTTAAGAAAATCCCAACTCATAAAGTCAAGTAGGAGATTAATTCATATG (SEQ ID NO:1)

FIG. 10

EcoRI gaattcAGGAGCTAGAACTGGTCAGGGCTGGGGCAATTTTTAATTAT

TGTTACGCAGGTCTTGCCTAGGGGGGGGGAGGCCGTATTATCTTCTA

NdeI

GTGATGTTTGCTGAAAACGCCTGAAGGAGAATAAcatATG (SEQ ID NO:2)

Figure 13:
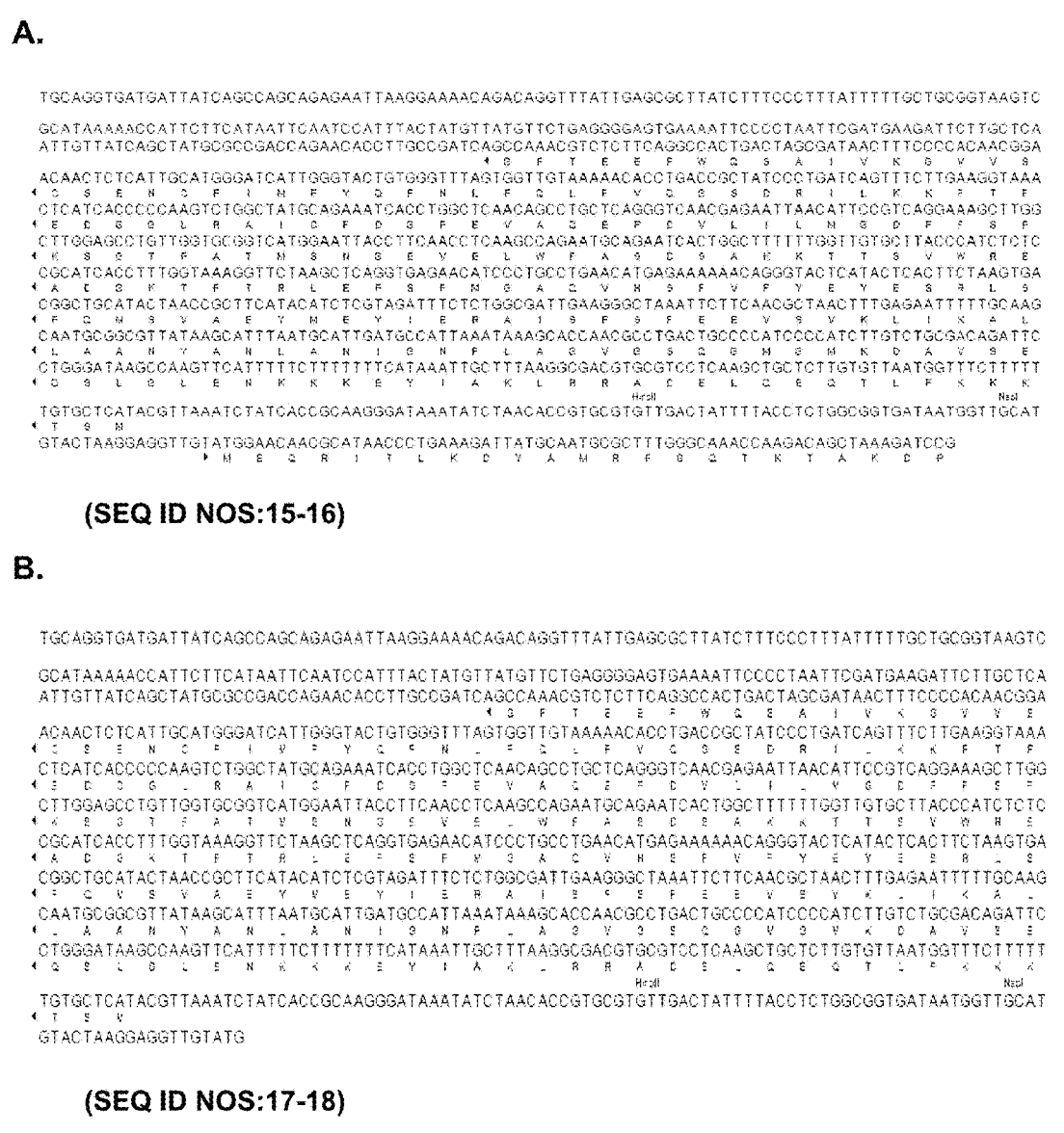

```
TGCAGGTGATGATTATCAGCCAGCAGAGAATTAAGGAAAACAGACAGGTTTATTGAGCGCTTATCTTTCCCTTTATTTTTGCTGCGGTAAGTC

GCATAAAAACCATTCTTCATAATTCAATCCATTTACTATGTTATGTTCTGAGGGGAGTGAAAATTCCCCTAATTCGATGAAGATTCTTGCTCA
ATTGTTATCAGCTATGCGCCGACCAGAACACCTTGCCGATCAGCCAAACGTCTCTTCAGGCCACTGACTAGCGATAACTTTCCCCACAACGGA
                                                   ◀ S  F  T  E  E  F  W  Q  S  A  I  V  K  G  V  V  S
ACAACTCTCATTGCATGGGATCATTGGGTACTGTGGGTTTAGTGGTTGTAAAAACACCTGACCGCTATCCCTGATCAGTTTCTTGAAGGTAAA
◀ C  S  E  N  C  F  I  M  F  Y  Q  F  N  L  F  Q  L  F  V  Q  S  S  D  R  I  L  K  K  F  T  F
CTCATCACCCCCAAGTCTGGCTATGCAGAAATCACCTGGCTCAACAGCCTGCTCAGGGTCAACGAGAATTAACATTCCGTCAGGAAAGCTTGG
◀ E  D  G  G  L  R  A  I  Q  F  D  G  F  E  V  A  Q  E  F  D  V  L  I  L  M  G  D  F  F  S  F
CTTGGAGCCTGTTGGTGCGGTCATGGAATTACCTTCAACCTCAAGCCAGAATGCAGAATCACTGGCTTTTTTGGTTGTGCTTACCCATCTCTC
◀ K  S  G  T  F  A  T  M  S  N  G  E  V  E  L  W  F  A  S  D  S  A  K  K  T  T  S  V  W  R  E
CGCATCACCTTTGGTAAAGGTTCTAAGCTCAGGTGAGAACATCCCTGCCTGAACATGAGAAAAAACAGGGTACTCATACTCACTTCTAAGTGA
◀ A  C  G  K  T  F  T  R  L  E  F  S  F  M  G  A  Q  V  H  S  F  V  F  Y  E  Y  E  S  R  L  S
CGGCTGCATACTAACCGCTTCATACATCTCGTAGATTTCTCTGGCGATTGAAGGGCTAAATTCTTCAACGCTAACTTTGAGAATTTTTGCAAG
◀ F  Q  M  S  V  A  E  Y  M  E  Y  I  E  R  A  I  S  F  S  F  E  E  V  S  V  K  L  I  K  A  L
CAATGCGGCGTTATAAGCATTTAATGCATTGATGCCATTAAATAAAGCACCAACGCCTGACTGCCCCATCCCCATCTTGTCTGCGACAGATTC
◀ L  A  A  N  Y  A  N  L  A  N  I  G  N  F  L  A  G  V  G  S  Q  G  M  G  M  K  D  A  V  S  E
CTGGGATAAGCCAAGTTCATTTTTCTTTTTTTCATAAATTGCTTTAAGGCGACGTGCGTCCTCAAGCTGCTCTTGTGTTAATGGTTTCTTTTT
◀ Q  S  L  G  L  E  N  K  K  K  E  Y  I  A  K  L  R  R  A  C  E  L  Q  E  Q  T  L  F  K  K  K
                                                        HpaII                                NsiI
TGTGCTCATACGTTAAATCTATCACCGCAAGGGATAAATATCTAACACCGTGCGTGTTGACTATTTTACCTCTGGCGGTGATAATGGTTGCAT
◀ T  S  M
GTACTAAGGAGGTTGTATGGAACAACGCATAACCCTGAAAGATTATGCAATGCGCTTTGGGCAAACCAAGACAGCTAAAGATCCG
                  ▶ M  E  Q  R  I  T  L  K  D  Y  A  M  R  F  G  Q  T  K  T  A  K  D  P
```

(SEQ ID NOS:15-16)

B.

```
TGCAGGTGATGATTATCAGCCAGCAGAGAATTAAGGAAAACAGACAGGTTTATTGAGCGCTTATCTTTCCCTTTATTTTTGCTGCGGTAAGTC

GCATAAAAACCATTCTTCATAATTCAATCCATTTACTATGTTATGTTCTGAGGGGAGTGAAAATTCCCCTAATTCGATGAAGATTCTTGCTCA
ATTGTTATCAGCTATGCGCCGACCAGAACACCTTGCCGATCAGCCAAACGTCTCTTCAGGCCACTGACTAGCGATAACTTTCCCCACAACGGA
                                                   ◀ S  F  T  E  E  F  W  Q  S  A  I  V  K  G  V  V  S
ACAACTCTCATTGCATGGGATCATTGGGTACTGTGGGTTTAGTGGTTGTAAAAACACCTGACCGCTATCCCTGATCAGTTTCTTGAAGGTAAA
◀ C  S  E  N  C  F  I  M  F  Y  Q  F  N  L  F  Q  L  F  V  Q  S  S  D  R  I  L  K  K  F  T  F
CTCATCACCCCCAAGTCTGGCTATGCAGAAATCACCTGGCTCAACAGCCTGCTCAGGGTCAACGAGAATTAACATTCCGTCAGGAAAGCTTGG
◀ E  D  G  G  L  R  A  I  Q  F  D  G  F  E  V  A  Q  E  F  D  V  L  I  L  M  G  D  F  F  S  F
CTTGGAGCCTGTTGGTGCGGTCATGGAATTACCTTCAACCTCAAGCCAGAATGCAGAATCACTGGCTTTTTTGGTTGTGCTTACCCATCTCTC
◀ K  S  G  T  F  A  T  M  S  N  G  E  V  E  L  W  F  A  S  D  S  A  K  K  T  T  S  V  W  R  E
CGCATCACCTTTGGTAAAGGTTCTAAGCTCAGGTGAGAACATCCCTGCCTGAACATGAGAAAAAACAGGGTACTCATACTCACTTCTAAGTGA
◀ A  C  G  K  T  F  T  R  L  E  F  S  F  M  G  A  Q  V  H  S  F  V  F  Y  E  Y  E  S  R  L  S
CGGCTGCATACTAACCGCTTCATACATCTCGTAGATTTCTCTGGCGATTGAAGGGCTAAATTCTTCAACGCTAACTTTGAGAATTTTTGCAAG
◀ F  Q  M  S  V  A  E  Y  M  E  Y  I  E  R  A  I  S  F  S  F  E  E  V  S  V  K  L  I  K  A  L
CAATGCGGCGTTATAAGCATTTAATGCATTGATGCCATTAAATAAAGCACCAACGCCTGACTGCCCCATCCCCATCTTGTCTGCGACAGATTC
◀ L  A  A  N  Y  A  N  L  A  N  I  G  N  F  L  A  G  V  G  S  Q  G  M  G  M  K  D  A  V  S  E
CTGGGATAAGCCAAGTTCATTTTTCTTTTTTTCATAAATTGCTTTAAGGCGACGTGCGTCCTCAAGCTGCTCTTGTGTTAATGGTTTCTTTTT
◀ Q  S  L  G  L  E  N  K  K  K  E  Y  I  A  K  L  R  R  A  C  E  L  Q  E  Q  T  L  F  K  K  K
                                                        HpaII                                NsiI
TGTGCTCATACGTTAAATCTATCACCGCAAGGGATAAATATCTAACACCGTGCGTGTTGACTATTTTACCTCTGGCGGTGATAATGGTTGCAT
◀ T  S  M
GTACTAAGGAGGTTGTATG
```

(SEQ ID NOS:17-18)

FIG. 21
A.
B.
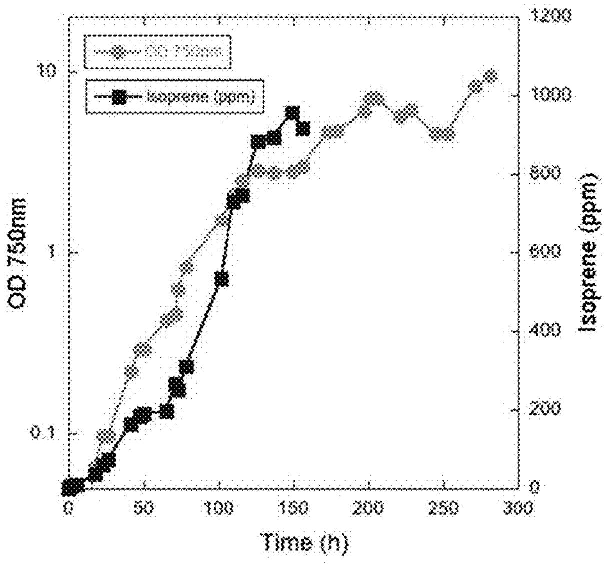

A. B.

METHODS FOR ISOPRENE AND PINENE PRODUCTION IN CYANOBACTERIA

CROSS-REFERENCE TO RELATED APPLICATIONS

This application is a divisional application of U.S. application Ser. No. 13/952,071, filed Jul. 26, 2013, which claims the benefit of U.S. Provisional Application No. 61/676,552, filed on Jul. 27, 2012, each of which is incorporated herein by reference in its entirety.

STATEMENT REGARDING FEDERALLY SPONSORED RESEARCH

This invention was made with government support under W911NF-09-2-0003, awarded by the ARMY/ARO, and 2009-28926-20110 and 2010-38926-20701, awarded by the USDA/NIFA. The government has certain rights in the invention.

FIELD OF THE INVENTION

The present invention provides methods of isoprenoid production. In particular, the present invention provides methods for producing isoprene and pinene in a host transgenic *Synechococcus* sp. PCC 7002 cyanobacterium.

BACKGROUND OF THE INVENTION

The development of fuels from renewable agricultural sources is currently and will likely continue to be important in meeting future energy demands and reducing the production of greenhouse gas emissions from fossil carbon sources. Current “biofuels” under development include “biodiesel,” which is derived via fatty acid synthesis from vegetable oil and ethanol fermented from sucrose obtained from plants such as corn and sugarcane.

More diverse and advanced biofuels and bio-products may be developed by exploiting metabolic pathways other than fatty acid synthesis and fermentation. For example, plants and bacteria use the 2-C-methyl-D-erythritol 4-phosphate (MEP) pathway to synthesize isoprenoids such as isoprene ($C_5H_8$, 2-methyl 1,3-butadiene) and pinene ($C_{10}H_{16}$, bicyclic monoterpene) as well as other terpenoids (see FIG. 1). End products of the MEP pathway are isopentyl diphosphate (IPP) and dimethylallyl diphosphate (DMAPP). Isoprene, which is a monomer of natural rubber and a precursor for synthetic rubber and thermoplastic elastomers, is made from DMAPP by the enzyme isoprene synthase (IspS). Pinene, a liquid bicyclic monoterpene, is made from IPP and DMAPP via geranyl diphosphate synthase (GPPS) and mono-terpene synthase (mono-TPS).

Isoprenoids are currently made industrially from petrochemicals and then converted into synthetic polymers, high-density liquid biofuels, and other materials (Mark et al., *In: Encyclopedia of Polymer Science and Technology* V7:782-854 (1967)). For example, pinene can be dimerized to exo-tetrahydrodicyclopentadiene, the energy value of which is 141,745 BTU/gallon (or 42.1 MJ $kg^{-1}$), nearly identical to that of the tactical jet fuel, JP-10 (Harvey et al., *Energy Fuels* 24:267 (2009)). Isoprene and, more particularly, the polymer cis-polyisoprene find utility in the production of specialty items such as vitamins, pesticides, pharmaceuticals, flavors, epoxy hardeners, and a variety of products containing elastic substances.

As petrochemical sources for industrial feedstocks and fuels become scarce, demand for alternative, carbon-neutral methods of producing isoprenoid feedstock chemicals will increase. Accordingly, there is a need for improved methods of producing isoprene and pinene.

SUMMARY OF THE INVENTION

In one aspect, this document provides methods for isoprenoid production. In some cases, the present invention provides a method comprising obtaining a host transgenic *Synechococcus* sp. PCC 7002 cyanobacterium comprising transgenes encoding isopentenyl diphosphate isomerase (IDI) (SEQ ID NO:8) and isoprene synthase (IspS) (SEQ ID NO:6). The method also can comprise observing, measuring, or recovering isoprene produced by such a transgenic cyanobacterium.

Isoprene can be produced according to the methods provided herein at a rate of at least about 330 μg per gram dry weight (gDW) per hour ($gDW^{-1}$ $h^{-1}$). In some cases, isoprene can be produced at a rate of at least about 660 μg $gDW^{-1}$ $h^{-1}$. In some cases, isoprene can be produced at a rate of at least about 1200 μg $gDW^{-1}$ $h^{-1}$. In some cases, isoprene can be produced at a rate of at least about 1600 μg $gDW^{-1}$.

The cyanobacterium can further comprise a promoter from *Synechocystis* sp. PCC 6803, a bacterial promoter, or a synthetic promoter designed to enhance or regulate gene expression. The *Synechocystis* sp. PCC 6803 promoter can be PcpcB. In some cases, a cyanobacterium of the present invention can comprise a synthetic promoter based on the *Synechocystis* sp. PCC 6803 PcpcB promoter (SEQ ID NO:1). In some cases, the cyanobacterium can comprise a designed, synthetic PpsaA/B promoter (SEQ ID NO:2) based on the native PpsaA/B promoter of *Synechocystis* sp. PCC 6803.

At least one of the transgenes can encode mRNA secondary structure and comprise codons preferred for expression in the cyanobacterium *Synechococcus* sp. PCC 7002. At least one of the transgenes can encode a protein identical to that isolated from a *Populus* species. At least one of the transgenes can encode an isoprene synthase having an amino acid sequence identical to that of *Populus trichocarpa* isoprene synthase (IspS, Accession no. EU693027, v.EU693027.1). At least one of the transgenes can encode an isopentenyl diphosphate isomerase having an amino acid sequence identical to that of *Populus trichocarpa* isopentenyl diphosphate isomerase (IDI, Accession no. EU693026, v. EU693026.1). At least one of the transgenes can encode IspS or IDI enzymes of identical amino acid sequence to those found in *Kudzu* species, *Eucalyptus* species, or *Salix* (willow) species.

At least one of the transgenes can be optimized for mRNA secondary structure and codon-usage in the cyanobacterium *Synechococcus* sp. PCC 7002. At least one of the transgenes can encode any of the 7 additional enzymes of the MEP pathway (see FIG. 1). These are deoxy-xylulose 5-phosphate (DXP) synthase (DXS), DXP reductoisomerase (DXR), diphosphocytidyl-methyl-erythritol (CDP-ME) synthase (IspD), CDP-ME kinase (IspE), methyl-erythritol-2,4-cyclodiphosphate (ME-cPP) synthase (IspF), hydroxymethylbutenyl diphosphate (HMBPP) synthase (IspG), and HMBPP reductase (IspH). At least one of the transgenes can encode MEP pathway enzymes of identical amino acid sequence to those found in *Kudzu* species, *Eucalyptus* species, or *Salix* (willow) species.

The transgenic cyanobacterium can further comprise one or more substitutions in a nucleotide sequence encoding a light-harvesting polypeptide. The light-harvesting polypeptide can be allophycocyanin (APC) and the one or more substitutions can reduce or eliminate expression of mRNA encoding the p-subunit of APC (ApcF, Locus Tag SynPCC7002_A1631) or ApcF polypeptide in the transgenic cyanobacterium. The transgenic cyanobacterium can further comprise one or more substitutions in a nucleotide sequence encoding a glycogen synthase. The glycogen synthase polypeptide can be Glycogen Synthase A1 (GlgA1, Locus Tag SynPCC7002_A1532) or Glycogen Synthase A2 (GlgA2, Locus Tag SynPCC7002_A2125). The one or more substitutions can reduce or eliminate expression of mRNA encoding GlgA1 or GlgA2 or expression of GlgA1 polypeptide or GlgA2 polypeptide. The cyanobacterium can further comprise at least one transgene selected from the group consisting of a transgene encoding hydroxymethylbutenyl diphosphate reductase (HDR, *Synechococcus* sp. PCC 7002 IspH) and 1-deoxy-D-xylulose-5-phosphate synthase (DXS). The cyanobacterium can further comprise at least one transgene selected from the group consisting of a transgene encoding geranyl diphosphate synthase (GPPS), and mono-terpene synthase (mono-TPS). At least one of the transgenes can encode a protein identical to that isolated from an *Artemisia* species. One of the transgenes can encode a protein of identical amino acid sequence to *Artemisia annua* mono-TPS (SEQ ID NO:20).

In some embodiments, isoprene can be produced under high $CO_2$ conditions. High $CO_2$ conditions can comprise 100% $CO_2$ atmospheric conditions. Isoprene production can also comprise subjecting the cyanobacterium to a light-dark cycle, wherein a light portion of the light-dark cycle comprises full intensity sunlight. The method can further comprise recovering the isoprene.

In another aspect, the present invention provides a method for pinene production. The method can comprise obtaining a host transgenic *Synechococcus* sp. PCC 7002 cyanobacterium comprising transgenes encoding geranyl diphosphate synthase (GPPS), and mono-terpene synthase (mono-TPS). The method can further comprise observing the production of pinene by the cyanobacterium, wherein pinene is produced at a rate of at least about 330 μg $gDW^{-1}$ $h^{-1}$. In one embodiment, pinene can be produced at a rate of at least about 660 μg $gDW^{-1}$ $h^{-1}$. In another embodiment, pinene can be produced at a rate of at least about 1200 μg $gDW^{-1}$ $h^{-1}$. In another embodiment, pinene can be produced at a rate of at least about 1600 μg $gDW^{-1}$ $h^{-1}$. In some cases, isoprene can be produced at a rate of at least about 2000 μg $gDW^{-1}$ $h^{-1}$. In some cases, isoprene can be produced at a rate of at least about 4000 μg $gDW^{-1}$ $h^{-1}$. In some cases, isoprene can be produced at a rate of at least about 8000 μg $gDW^{-1}$ $h^{-1}$.

In some embodiments, at least one of the transgenes can comprise codons preferred for expression in the cyanobacterium. At least one of the transgenes can encode a protein identical to that isolated from an *Artemisia* species. One of the transgenes can encode a protein of identical amino acid sequence to *Artemisia annua* mono-TPS (SEQ ID NO:20). The cyanobacterium can further comprise at least one transgene selected from the group consisting of a transgene encoding hydroxymethylbutenyl diphosphate reductase (HDR) and 1-deoxy-D-xylulose-5-phosphate synthase (DXS).

In some embodiments, pinene can be produced under high $CO_2$ conditions. High $CO_2$ conditions comprise 100% $CO_2$ atmospheric conditions. Pinene production can comprise subjecting the cyanobacterium to a light-dark cycle, where a light portion of the light-dark cycle comprises full intensity sunlight. The method can further comprise recovering the pinene.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 shows the *Synechocystis* sp. PCC 6803 c-phycocyanin-b (PcpcB) promoter region (SEQ ID NO:1) used for high-level gene expression in *Synechococcus* sp. PCC 7002.

FIG. 10 presents a promoter region designed for high-level gene expression in *Synechococcus* sp. PCC 7002 based on the *Synechocystis* sp. PCC 6803 P700 apo-protein subunit 1A/1B (psaA/B) promoter (SEQ ID NO:2). The synthetic promoter contains a unique ribosomal binding site located in the region 8 to 13 nucleotides upstream of the ATG start codon embedded within the NdeI restriction site.

FIG. 13 presents nucleotide and encoded amino acid sequences of the bacteriophage lambda $P_R$ promoter with the thermolabile cI857 repressor, Cro ribosomal binding site, with (A) (SEQ ID NOS:15-16) and without (B) (SEQ ID NOS:17-18) a nucleotide sequence encoding the first 22 amino acids of the Cro protein. Both gene constructs are designed for temperature regulated gene expression in *Synechococcus* sp. PCC 7002 cyanobacteria. The sequence shown in (A) allows translational fusion of the N-terminal segment of Cro to sequences of interest (such as DXS in FIG. 12), to improve mRNA and protein stability.

FIG. 21 shows isoprene production and growth to high cell density (B) in a fermenter culture of the *Synechococcus* sp. PCC 7002 (IspS-IDI) strain (A). Cells grown under ~500 μmol photons $m^{-2}$ $s^{-1}$ light intensity, with periodic additions of 100% $CO_2$, grew to a high density of ~2.2 gDW $L^{-1}$ (OD 750 nm ~10).

DETAILED DESCRIPTION OF THE INVENTION

Transgenic *Synechococcus* Cyanobacteria

Figure 1:
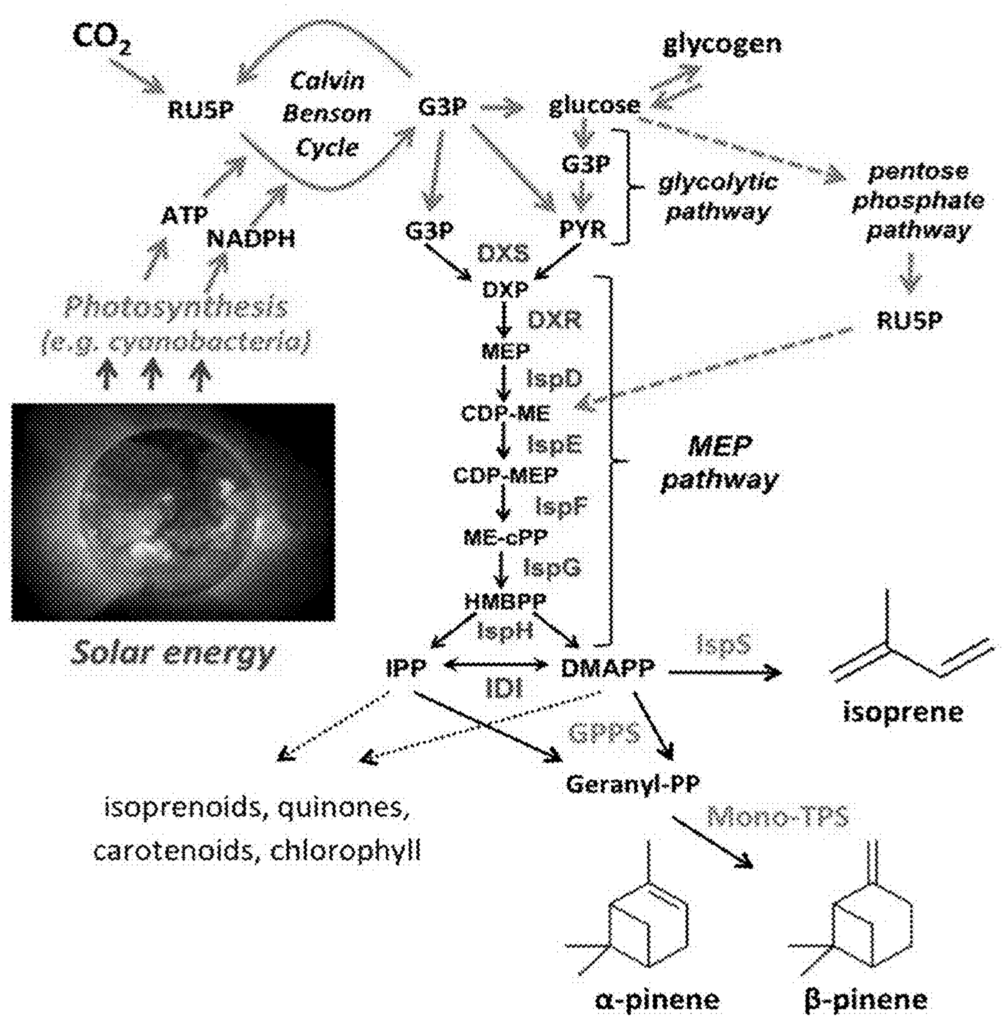
FIG. 1 illustrates pathways of photosynthetic and respiratory carbon flow into the 2-C-methyl-D-erythritol 4-phosphate (MEP) pathway for isoprenoid production in cyanobacteria. Methyl-erythritol phosphate (2-C-methyl-D-erythritol 4-phosphate; MEP) is converted into isopentenyl diphosphate (IPP) and dimethylallyl diphosphate (DMAPP)—the precursors for quinones, carotenoids, chlorophyll, and isoprenoids such as isoprene and pinene. Cyanobacteria possess MEP pathway enzymes but lack isoprene synthase (IspS), the enzyme required for isoprene production, as well as the enzymes necessary for pinene production: geranyl diphosphate synthase (GPPS), and mono-terpene synthase (mono-TPS). ATP and NADPH produced by photosynthesis drive carbon capture by the Calvin-Banson cycle to generate the glyceradehyde 3-phosphate (G3P) and pyruvate (Pyr) precursors of MEP pathway enzymes. Other metabolites in the pathway include Deoxyxylulose 5-phosphate (DXP), methyl-erythritol-4-phosphate (MEP), diphosphocytidyl-methyl-erythritol (CDP-ME), CDP-methylerythritol-2-phosphate (CDP-MEP), methylerythritol-2,4-cyclodiphosphate (ME-cPP), and hydroxymethylbutenyl diphosphate (HMBPP). Enzymes in the MEP pathway and the genes that encode them include DXP synthase (DXS, NCBI Locus Tag SYNPCC7002_A1172), DXP reductoisomerase (DXR; NCBI Locus Tag SYNPCC7002_A0818), CDP-ME synthase (MCT or IspD; NCBI Locus Tag SYNPCC7002_A1905), CDP-ME kinase (CMK or IspE; NCBI Locus Tag SYNPCC7002_A2416), Me-cPP synthase (MDS or IspF; NCBI Locus Tag SYNPCC7002_A1166), HMBPP synthase (HDS, GcpE, or IspG; NCBI Locus Tag SYNPCC7002_A0743), HMBPP reductase (HDR or IspH; NCBI Locus Tag SYNPCC7002_A0517), and IPP-DMAPP isomerase (Fni or IDI; NCBI Locus Tag SYNPCC7002_A1132). The IDI isomerase is a key enzyme for inter-conversion of IPP and DMAPP for efficient isoprene production.

The invention provided herein is based, at least in part, on Applicants' discovery that genetically modified *Synechococcus* cyanobacteria produce isoprene at rates promising for commercial development and that these isoprene-producing cyanobacteria grow efficiently under an atmosphere of up to 100% $CO_2$. It was also discovered that expressing unique combinations of MEP pathway enzymes increases isoprene production in these cyanobacteria.

*Synechococcus* sp. PCC 7002 (formerly *Agmenellum quadruplicatum* PR-6; American Type Culture Collection strain 27167) is a strain of marine cyanobacteria that was originally isolated by Van Baalen et al., *Botanica Marina* 4:129-139 (1962), from a marine estuarine mud flat in Puerto Rico. *Synechococcus* sp. PCC 7002 cyanobacteria are superior to other genetically modifiable cyanobacteria because of their rapid doubling time of approximately 3.5 hours, tolerance to and continued rapid growth under extreme light intensity (>2× full sunlight or 4000-5000 μmol photons $m^{-2}s^{-1}$), tolerance of a wide range of salt concentrations, and optimal growth at moderately high temperatures of 37° C. to 40° C. Furthermore, genetic modifications in *Synechococcus* sp. PCC 7002 cyanobacteria are quite stable. Unlike heterotrophic marine bacteria genetically modified to express components necessary for isoprene production (see WO2013/096683), recombinant *Synechococcus* sp. PCC 7002 cyanobacteria use sunlight and do not require biomass or other carbon source for isoprenoid production via the 2-C-methyl-D-erythritol 4-phosphate (MEP) or mevalonate (MVA) pathways.

Thus, *Synechococcus* sp. PCC 7002 cyanobacteria are particularly well-adapted for genetic modification, growth, and hydrocarbon production in photo-bioreactors under full sunlight in arid regions. In addition, while high $CO_2$ concentrations are toxic to many cyanobacteria, *Synechococcus* cyanobacteria grow and produce isoprene under an atmosphere of up to 100% $CO_2$, which suggests that the carbon necessary for isoprenoid production can be derived efficiently from concentrated, industrial, agricultural, or other waste $CO_2$ streams.

*Synechococcus* sp. PCC 7002 cyanobacteria may be obtained from the Pasteur Collection of Cyanobacteria (PCC), which is part of the Biological Resource Center Institut Pasteur (CRBIP) at the Institut Pasteur, Paris, France (see pasteur.fr/ip/easysite/pasteur/en/research/collectionscrbip on the World Wide Web).

In one aspect, the present invention provides a *Synechococcus* sp. PCC 7002 cyanobacterium comprising an exogenous nucleic acid sequence (e.g., a transgene) encoding one or more key enzymes for synthesizing isoprenoids and, more particularly, for converting DMAPP into isoprene and/or converting IPP and DMAPP into pinene. The term "transgene" as used herein refers to a gene that comprises a non-native, recombinant, or modified nucleotide sequence for introduction into a microorganism. In one embodiment, the present invention provides a *Synechococcus* sp. PCC 7002 cyanobacterium comprising transgenes encoding isopentenyl diphosphate isomerase (IDI) and isoprene synthase (IspS).

In certain embodiments, a transgenic *Synechococcus* sp. PCC 7002 cyanobacterium further comprises at least one transgene selected from the group consisting of a transgene encoding IPP-DMAPP isomerase (IDI), hydroxymethylbutenyl diphosphate reductase (HDR or IspH), 1-deoxy-D-xylulose-5-phosphate synthase (DXS), and deoxy-xylulose 5-phosphate reductoisomerase (DXR). For example, a transgenic *Synechococcus* sp. PCC 7002 cyanobacterium can comprise one or more transgenes encoding IDI, IspS, HDR, DXS, and DXR. These genes may be obtained from various bacterial, algal, or higher plant sources including but not limited to *Esherichia coli, Bacillus coagulans, Bacillus subtilis, Populus alba, Populus nigra, Populus trichocarpa, Pueraria montana*, and *Eucalyptus obliqua*. In some cases, genes obtained from one or more of these sources can be expressed from strong cyanobacterial promoters. In some cases, messenger RNA transcripts and protein-coding sequences for genes obtained from one or more of these sources can be optimized for transcription and translation in *Synechococcus* sp. PCC cyanobacteria. Nucleotide and amino acid sequences can be found in Gambliel et al., *Journal Biological Chemistry* 259:740 (1984); Bohlman et al., *Proceedings National Academy Science USA* 95:4126 (1998); Lu et al., *Plant Physiology* 130:477 (2002); Carter et al., *Phytochemistry* 64:425 (2003); and at the National Center for Biotechnology Information (found at ncbi.nlm.nih.gov on the World Wide Web).

For pinene production, a transgenic *Synechococcus* sp. PCC 7002 cyanobacterium can further comprise at least one transgene selected from the group consisting of geranyl diphosphate synthase (GPPS) and mono-terpene synthase (mono-TPS). For example, a transgenic *Synechococcus* sp. PCC 7002 cyanobacterium can comprise transgenes encoding IDI, IspS, GPPS, and mono-TPS. In some cases, a transgenic *Synechococcus* sp. PCC 7002 cyanobacterium can comprise transgenes encoding IDI, IspS, HDR, DXS, DXR, GPPS, and mono-TPS. These genes may be obtained from various bacterial, algal, or higher plant sources including but not limited to *Esherichia coli, Bacillus coagulans, Bacillus subtilis, Populus alba, Populus nigra, Populus trichocarpa, Pueraria Montana, Artemisia annua, Abies grandis*, and *Salvia officinalis*. In some cases, genes obtained from one or more of these sources can be expressed from strong cyanobacterial promoters. In some cases, messenger RNA transcripts and protein-coding sequences for genes obtained from one or more of these sources can be optimized for transcription and translation in *Synechococcus* sp. PCC 7002 cyanobacteria. Nucleotide and amino acid sequences for the *E. coli* enzymes can be found at ecocyc.org on the World Wide Web (see also Kessler et al., Nucleic Acids Research 39:0583 (2011). Nucleotide and amino acid sequences for the *Bacillus* and *Populus* species can be found in Zhao et al., *Applied Microbiology Biotechnology* 90:1915 (2011) and Wiberley et al., *Plant, Cell and Environment* 32:939 (2009), and at populus.db.umu.se on the World Wide Web. These sequences are also available at the National Center for Biotechnology Information (found at ncbi.nlm.nih.gov on the World Wide Web).

In some cases, at least one of the transgenes in a cyanobacterium described herein encodes a protein having an amino acid sequence identical or substantially identical to a protein isolated from a *Populus* species. IspS genes cloned from *Populus* species have demonstrated IspS enzymatic activity. See, e.g., Silver et al., *J. Biol. Chem.* 270:13010-13016 (1995); Sasaki et al., *FEBS Lett.* 579:2514-2518 (2005). See also U.S. Patent Publication No. 2011/0039323, which is incorporated herein by reference in its entirety.

Accordingly, in one embodiment, at least one of the transgenes encodes an isoprene synthase of identical amino acid sequence to *Populus trichocarpa* isoprene synthase (IspS, Accession no. EU693027, v.EU693027.1; SEQ ID NO:6). In some cases, at least one of the transgenes encodes an isoprene synthase having an amino acid sequence identical to *Populus trichocarpa* IspS (PIspS) and at least one of the transgenes encodes *E. coli* IDI. *Populus trichocarpa* IDI (PIDI, Accession no. EU693026, v. EU693026.1; SEQ ID NO:8) may also be used, as it has higher activity than *E. coli* IDI, and PIDI is easily expressed at high levels in *E. coli*. However, in some embodiments, *E. coli* IDI may be substituted. There is no known or putative bacterial IspS.

Cloning of MEP pathway genes from *Populus* species or from other sources can be performed as described in U.S. Patent Publication No. 2011/0039323, which is incorporated herein by reference in its entirety. In some cases, at least one of the transgenes in a cyanobacterium described herein can encode IspS or IDI enzymes having substantially identical amino acid sequences to those found in a *Kudzu* species, a *Eucalyptus* species, or a *Salix* (willow) species.

Figure 15:
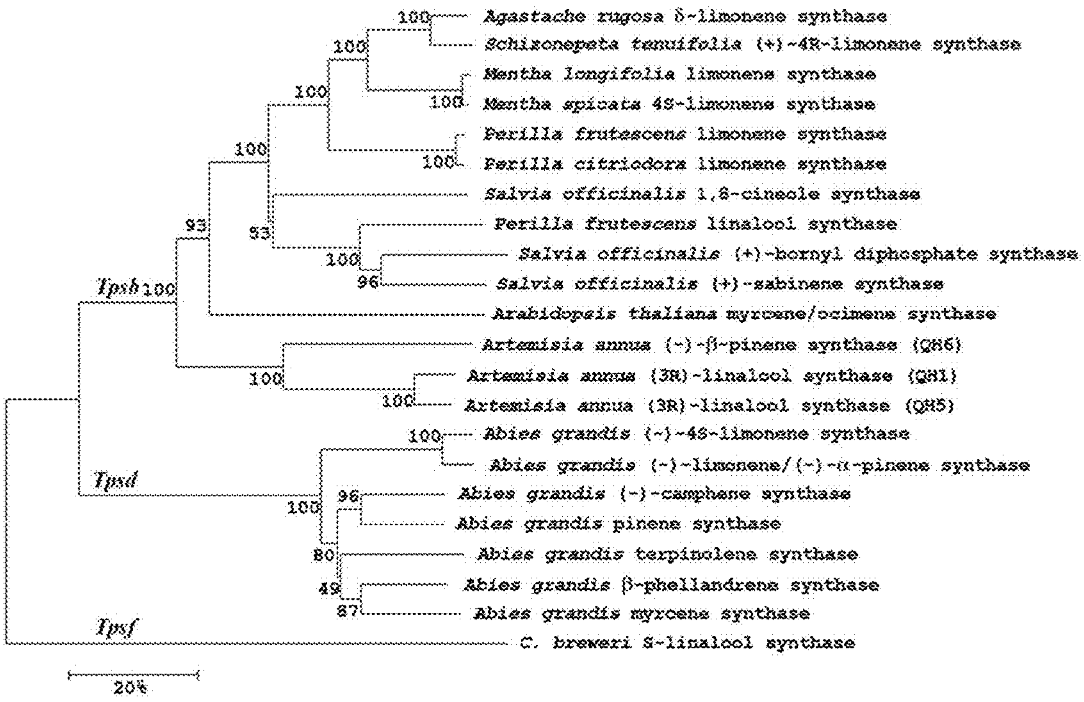
FIG. 15 presents a phylogenetic tree depicting inferred evolutionary relationships among several mono-terpene synthases from *Artemisia annua* and related species (modified from Lu et al., *Plant Physiology* 130(1): 477-486 (2002)).

In some cases, at least one of the transgenes is isolated from an *Artemisia* (family Asteraceae) species. For example, a transgene can be isolated from the species *Artemisia annua*. The mono-terpene synthase (mono-TPS) catalyzes almost exclusively the synthesis of β-pinene in *Artemisia annua*. Lu et al., *Plant Physiol.* 130:477-486 (2002). Accordingly, in some cases, at least one transgene is *Artemisia annua* mono-TPS (Accession no. AF276072, v.AF276072.1). Nucleotide and encoded amino acid sequences of the QH6 mono-TPS gene from *Artemisia annua* are shown in SEQ ID NOS:19-20). In some cases, mono-TPS enzymes from species related to *Artemisia annua* can be used to produce β-pinene in *Synechococcus* sp. PCC 7002 cyanobacteria. A phylogenetic tree (FIG. 15) presents species related to *Artemisia annua* from which alternative mono-TPS genes might be derived for expression in *Synechococcus* sp. PCC 7002.

MEP pathway genes from other sources such as, for example, kudzu and other legumes, *eucalyptus*, or *Melaleuca* species can be used according to the methods provided herein. For example, isoprene synthase sequences from gymnosperms such as *Picea* species could be used.

In certain embodiments, at least one of the transgenes comprises codons and messenger RNA secondary structure preferred for expression in *Synechococcus* sp. PCC 7002 cyanobacteria. For example, one may wish to optimize gene expression by modifying the transgenes with codons preferentially or optimally used by the host. Most amino acids are encoded by more than one codon. Each organism carries a bias in the usage of the 61 available amino acid codons. Codon-optimization of sequences for expression in a host organism can significantly improve protein abundance and metabolite production rates. In addition, optimization can minimize inhibitory secondary structures in mRNA transcripts and, thus, greatly increase protein synthesis. In certain embodiments, one may wish to modify a gene, for example IDI, with *Synechococcus*-specific codons and optimized mRNA secondary structure.

In some cases, a transgenic *Synechococcus* cyanobacterium further comprises a promoter from the cyanobacterium *Synechocystis* sp. PCC 6803 to drive expression of nucleic acid sequences encoding MEP pathway or isoprenoid synthesis components including, for example, isopentenyl diphosphate (IPP), IPP-isomerase (IDI), and isoprene synthase (IspS). An exemplary *Synechocystis* sp. PCC 6803 promoter is the *Synechocystis* c-phycocyanin β-subunit (cpcB) promoter (SEQ ID NO:1). The upstream sequence of the *Synechocystis* cpcB gene, which contains the promoter region for RNA polymerase binding has been used to construct expression vectors for high-level gene expression and genetic engineering of cyanobacteria. See, e.g., Xu et al., *Photosynth. Res. Protocols* 684:273-293 (2010). In some cases, the *Synechocystis* cpcB promoter can be used to avoid undesirable homologous recombination with an endogenous *Synechococcus* cpcB promoter.

For example, a transgene expressed in a genetically modified cyanobacterium of the present invention can encode mRNA secondary structure and comprise codons preferred for expression in the cyanobacterium *Synechococcus* sp. PCC 7002. In particular, a transgene can comprise codons preferred for expression in *Synechococcus* sp. PCC 7002 cyanobacteria of any of the seven MEP pathway enzymes: deoxy-xylulose 5-phosphate synthase (DXS), DXP reductoisomerase (DXR), diphosphocytidyl-methyl-erythritol (CDP-ME) synthase (IspD), CDP-ME kinase (IspE), methyl-erythritol-2,4-cyclodiphosphate (ME-cPP) synthase (IspF), hydroxymethylbutenyl diphosphate (HMBPP) synthase (IspG), and HMBPP reductase (IspH). For example, a transgene can comprise a nucleic acid sequence derived from *Bacillus amyloliquefaciens* FZB42, 2-C-methyl-D-erythritol 2,4-cyclodiphosphate synthase (IspF) gene that is optimized for mRNA secondary structure and codon-usage in *Synechococcus* sp. PCC 7002 (Locus tag RBAM_001160, SEQ ID NO:13). In some cases, a transgene comprises a codon-optimized sequence from *Bacillus amyloliquefaciens* FZB42, 4-hydroxy-3-methylbut-2-enyl diphosphate reductase (IspH) (Locus tag RBAM_023470, SEQ ID NO:11). In other cases, a codon-optimized sequence is from *Bacillus amyloliquefaciens* FZB42 deoxyxylulose phosphate synthase (DXS) (Locus tag RBAM_022600, SEQ ID NO:9).

A transgenic cyanobacterium as described herein can further comprise a nickel (Ni)-regulated promoter (Liu and Curtis, *Proc. Natl. Acad. Sci. USA* 106:21550-21544 (2009)), or other regulated promoter for Ni-induced or otherwise regulated expression of isoprenoid synthesis and MEP pathway genes.

Figure 12:
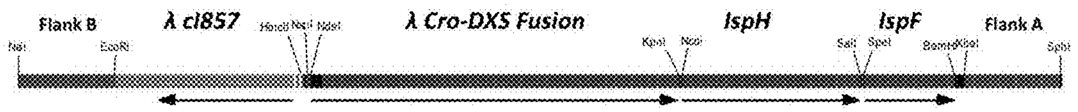
FIG. 12 presents a map of a bacteriophage lambda CI857-Cro-DXS fusion-IspH-IspF gene construct designed for high-level, temperature-regulated expression of MEP pathway DXS-IspH-IspF genes in *Synechococcus* sp. PCC 7002 cyanobacteria. SEQ ID NOS:21-22 set forth nucleotide and encoded amino acid sequences of the first 22 amino acids of the Cro gene from the bacteriophage lambda $P_R$ promoter in a fusion construct with the MEP pathway DXS gene codon optimized for expression in *Synechococcuss* PCC 7002. The first 7 amino acids of the DXS gene were excluded in this fusion design.
Figure 14:
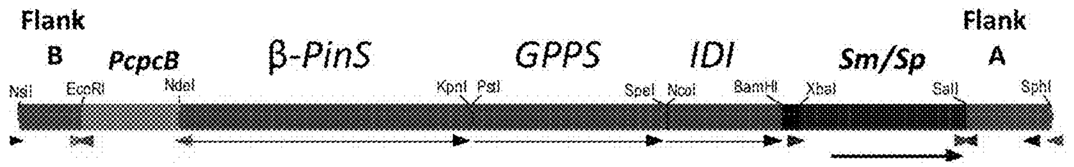
FIG. 14 presents a map of a gene construct designed for high-level expression of a mono-terpene synthase, β-pinene synthase (β-PinS) from *Artemisia annua* (Accession no. AF276072, v.AF276072.1; SEQ ID NOS:19-20) and a geranyl diphosphate synthase (GPPS1) from *Abies grandis* (Accession no. AF513111, v. AF513111.1; SEQ ID NOS:3-4), each optimized for mRNA secondary structure and codon-usage in *Synechococcus* sp. PCC 7002 cyanobacteria, and MEP pathway IDI isomerase genes. The construct also carries the codon-optimized IDI isomerase gene (SEQ ID NO:7) that encodes the *Populus trichocarpa* IDI enzyme (Accession no. EU693026, v. EU693026.1; SEQ ID NO:8) for enhanced carbon flux via the MEP pathway.

A transgenic cyanobacterium as described herein can further comprise a bacteriophage lambda $P_R$ promoter and thermolabile cI857 repressor protein (SEQ ID NOS:15-18) to enable temperature-regulated expression of isoprenoid synthesis and MEP pathway genes (see FIGS. 12-13).

A transgenic cyanobacterium as described herein can further comprise a promoter region regulated in response to isoprene, pinene, or other isoprenoids to enable isoprenoid-induced expression of isoprenoid synthesis and MEP pathway genes.

A transgenic cyanobacterium of the present invention can additionally or alternatively comprise mRNA secondary structure and codon-optimized transgenes that encode enzymes of the mevalonate (MVA) pathway. The MVA pathway, which is found in eukaryotes, archaea, and plants, includes seven enzymatic reactions that convert pyruvate to isopentenyl diphosphate (IPP), which is further converted via the IDI isomerase to the DMAPP precursor for isoprene (see, e.g., Xue and Ahring, *Appl. Environ. Microbiol.* 77:2399-2405 (2011)). The MVA pathway enzymes are pyruvate dehydrogenase (AceE), acetoacetyl-CoA thiolase (AtoB), hydroxymethylglutaryl-CoA synthase (HMGS), hydroxymethyl-glutaryl-CoA reductase (HMGR), mevalonate kinase (MK), phosphomevalonate kinase (PMK), and mevalonate pyrophosphate decarboxylase (MPD). At least one of the transgenes can encode MVA enzymes of identical amino acid sequence to those found in *Escherichia coli* species, *Bacillus* species, or *Saccharomyces* species.

In some cases, a transgenic *Synechococcus* cyanobacterium further comprises a promoter from the cyanobacterium *Synechocystis* sp. PCC 6803 to drive expression of nucleic acid sequences encoding one or more MVA pathway components. An exemplary *Synechocystis* sp. PCC 6803 promoter is the *Synechocystis* c-phycocyanin β-subunit (cpcB) promoter. The upstream sequence of the *Synechocystis* cpcB gene, which contain the promoter region for RNA polymerase binding has been used to construct expression vectors for high-level gene expression and genetic engineering of cyanobacteria. See, e.g., Xu et al., *Photosynth. Res. Protocols* 684:273-293 (2010). In some cases, the *Synechocystis* cpcB promoter (FIG. 5; SEQ ID NO:1) can be used to avoid undesirable homologous recombination with an endogenous *Synechococcus* cpcB promoter.

A transgenic cyanobacterium of the present invention can comprise, in some cases, one or more substitutions in a nucleotide sequence encoding a light-harvesting, phycobiliprotein polypeptide. A light-harvesting polypeptide can be a subunit of the allophycocyanin (APC) or phycocyanin (PC) light-harvesting, protein complexes. The introduction of one or more substitutions in a sequence encoding a light-harvesting polypeptide can reduce or eliminate expression of mRNA encoding ApcF (Locus Tag SynPCC7002_A1631) or a β-subunit polypeptide of APC, or reduce or eliminate expression of mRNA encoding CpcB (Locus Tag SynPCC7002_A2209) or a β-subunit polypeptide of PC in the transgenic cyanobacterium.

In another aspect, a transgenic cyanobacterium of the present invention can comprise one or more substitutions in a nucleotide sequence encoding a chlorophyll biosynthesis enzyme.

In a further aspect, a transgenic cyanobacterium can further comprise one or more substitutions in a nucleotide sequence encoding a glycogen synthase enzyme. For example, a glycogen synthase polypeptide can be Glycogen Synthase A1 (Locus Tag SynPCC7002_A1532) or Glycogen Synthase A2 (Locus Tag SynPCC7002_A2125). The introduction of one or more substitutions in a sequence encoding Glycogen Synthase A1 and/or Glycogen Synthase A2 can reduce or eliminate expression of mRNA encoding GlgA1 or GlgA2 or expression of the encoded polypeptides.

The cyanobacterium can further comprise one or more substitutions in a nucleotide sequence encoding an ADP-Glucose pyrophosphorylase that synthesizes the ADP-glucose precursor for synthesis of both glycogen and the soluble sugars, glucosylglycerol (GGol) and glucosylglycerate (GGate). The ADP-Glucose pyrophosphorylase polypeptide can be GlgC (Locus Tag SynPCC7002_A0095). The one or more substitutions can reduce or eliminate expression of mRNA encoding GlgC or expression of GlgC polypeptide.

The cyanobacterium can further comprise one or more substitutions in a nucleotide sequence encoding a sucrose phosphate synthase that synthesizes sucrose. The sucrose phosphate synthase polypeptide can be SpsA (Locus Tag SynPCC7002_A0888). The one or more substitutions can reduce or eliminate expression of mRNA encoding SpsA or expression of SpsA polypeptide).

The cyanobacterium can further comprise one or more substitutions in a nucleotide sequence encoding a GGol (GGate) synthase that synthesizes the soluble sugars glucosylglycerol (GGoI) and glucosylglycerate (GGate). The GGoI(GGate) synthase can be Glucosylglycerate-P-synthase (GpgS, ACCESSION No. A2021), Glucosylglycerate-P-phosphatase GpgP (A2022), Glucosylglycerol-P-synthase GgpS (Locus Tag SynPCC7002_A2851), or Glucosylglycerol-P-phosphatase GgpP (Locus Tag SynPCC7002_A2841). The introduction of one or more substitutions in such sequences can reduce or eliminate expression of mRNA encoding GpgS, GpgG, GgpS, or GgpP, or can reduce or eliminate expression of a GpgS, GpgG, GgpS, or GgpP polypeptide.

In a further embodiment, a transgenic cyanobacterium having one or more transgenes encoding geranyl diphosphate synthase (GPPS) and/or mono-terpene synthase (mono-TPS) can further comprise any or all mRNA structure and codon-optimized genes for the MEP and/or MVA pathways or dual sets of any of the genes of these pathways. In some cases, a transgenic cyanobacterium having one or more transgenes encoding geranyl diphosphate synthase (GPPS) and/or mono-terpene synthase (mono-TPS) can further comprise any or all of the light-harvesting protein deletions, glycogen synthase (GlgA1, GlgA2) deletions, ADP-Glucose pyrophosphorylase (GlgC), or soluble sugar synthase (SpsA, GpgS, GpgP, GgpS, or GgpP) deletions described herein. It may also be desirable to obtain a transgenic cyanobacterium having one or more transgenes encoding geranyl diphosphate synthase (GPPS) and/or mono-terpene synthase (mono-TPS), one or more inactivated light-harvesting polypeptides, a glycogen synthase enzyme, and one or more inactivated soluble sugar synthases. It will be understood that such a transgenic cyanobacterium may additionally comprise any or all mRNA structure- and codon-optimized genes for the MEP or MVA pathways or combinations thereof.

Figure 6:
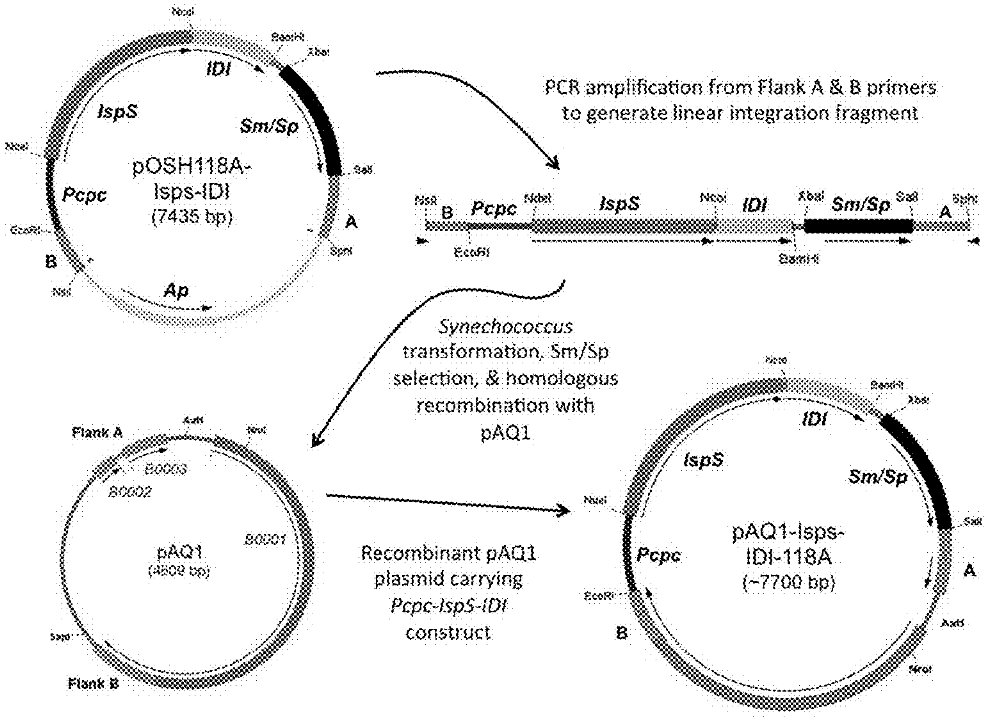
FIG. 6 illustrates a strategy for targeting genes into high-copy number plasmids for high-level gene expression in *Synechococcus* sp. PCC 7002. Synthetic, codon-optimized genes (e.g., poplar PIspS-IDI, codon-optimized for *Synechococcus* sp. PCC 7002) were amplified by polymerase chain reaction (PCR) and propagated on an *E. coli* plasmid such as pOSH118A-IspS-IDI (also designated pOSH1108). The 5014 bp DNA insert carries the strong cpcB promoter (Pcpc) controlling the PIspS-IDI genes and a selectable Sm/Sp-resistance marker sandwiched between 'Flank B and A' regions that are homologous to regions of plasmid pAQ1 of *Synechococcus* 7002. The region from Flank A to Flank B is amplified by PCR to generate linear, targeting DNA fragments. These fragments are introduced into *Synechococcus* by physiological transformation. Selection for Sm/Sp resistance forces double homologous recombination between the corresponding Flank A and B regions of the introduced DNA and plasmid pAQ1 to generate recombinant plasmids such as pAQ1-IspS-IDI-118A. Similar strategies can be used for targeting genes to other plasmids or chromosomal sites in *Synechococcus* sp. PCC 7002 or other cyanobacteria.

Any appropriate genetic transformation method can be used to introduce a nucleic acid (e.g., a transgene) into a *Synechococcus* cyanobacterium. In some cases, a nucleic acid as described herein is introduced into a *Synechococcus* sp. PCC 7002 cyanobacterium by physiological transformation and homologous recombination (Cierico et al., *Methods in Mol. Biol.* 362:155-171 (2007)) or by introducing one or more plasmids capable of replicating in certain cyanobacterial strains (Takeshima et al., *DNA Res.* 1:181-189 (1994)). For example, transgenes introduced into *Synechococcus* sp. PCC 7002 cyanobacteria may be targeted to plasmid or chromosomal sites. *Synechococcus* sp. PCC 7002 has six plasmids, pAQ1, pAQ3, pAQ4, pAQ5, pAQ6, and pAQ7, of which pAQ1 is a relatively small (~4800 bp), high-copy number plasmid (approximately 50 copies per cell). A strategy for targeting genes to plasmid pAQ1 (based on Xu et al., In: Photosynth. Res. Protocols (Carpentier, R. ed.) pp: 273-293 (2010)) is illustrated in FIG. 6. Similar strategies can be used to target transgenes to other neutral or selectable sites in the *Synechococcus* sp. PCC 7002 genome. Neutral sites in the chromosome include petJ2 (Locus Tag SynPCC7002_A2391), cytM (Locus Tag SynPCC7002_A0375), and many other genes of no known function that are expressed at basal levels in microarray (see, e.g., FIG. 2) or other global gene expression studies.

In some embodiments, introduced transgenes may have toxic impacts and may be easily lost, especially from plasmids. Plasmid pAQ4 of *Synechococcus* sp. PCC 7002 may be lost in the absence of selective pressure to maintain it. For commercial isoprenoid production, however, it is desirable to maintain transgenes without the need for antibiotic selection. In some cases, a "plasmid addiction" strategy can be used to maintain plasm ids and linked transgenes. See, e.g., Kroll et al., *Microb. Biotechnol.* 3:634 (2010). For example, an essential gene can be linked with one or more introduced transgenes (e.g., codon-optimized IspS, IDI, or MEP pathway genes) and targeted to a neutral site in a plasmid such as pAQ4. In some cases, petJ1 (Locus Tag SynPCC7002_A0167), which encodes an essential electron transport protein can be linked with transgenes and targeted to plasmid pAQ4. In some cases, petJ1, which encodes an essential electron transport protein can be linked with transgenes and targeted to plasmid pAQ4. Following segregational loss of native pAQ4 plasm ids, the chromosomal petJ1 gene can be inactivated to ensure maintenance of the engineered plasmid and introduced transgene. The introduced copy of petJ1 can be derived from another cyanobacterium (e.g., *Synechocystis* sp. PCC 6803) to avoid possible recombination with the native *Synechococcus* gene. Similar "plasmid addiction" strategies known to those practicing in the art, and which employ other essential genes, can be used to maintain a variety of transgenes.

Figure 9:
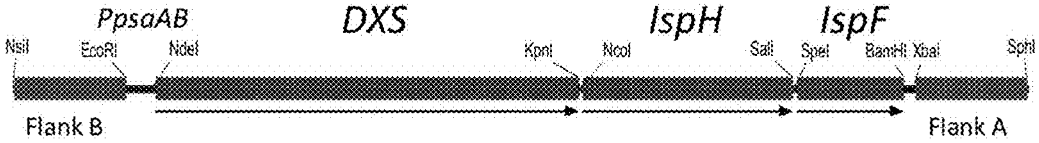
FIG. 9 presents the map of a synthetic, mRNA secondary structure and codon-optimized, gene construct for expression of MEP pathway DXS-IspH-IspF genes in *Synechococcus* sp. PCC 7002 cyanobacteria. These genes encode proteins identical to the *Bacillus amyloliquefaciens* FZB42 DXS (Locus Tag RBAM_022600; SEQ ID NO:10), IspH (Locus Tag RBAM_023470; SEQ ID NO:12), and IspF (Locus Tag RBAM_001160; SEQ ID NO:14) enzymes.
Figure 11:
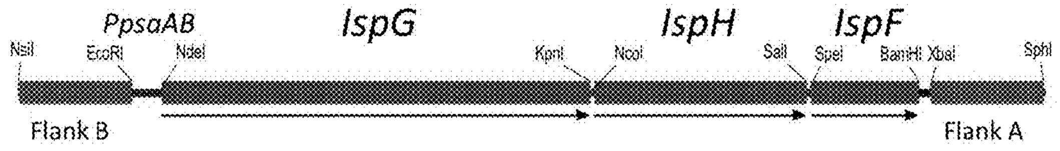
FIG. 11 presents a map of a gene construct designed for high-level expression of MEP pathway IspG-IspH-IspF genes in *Synechococcus* sp. PCC 7002 cyanobacteria.

In some embodiments, an optimized IspS, IDI, and/or MEP pathway transgene is maintained without the use of antibiotic resistance selection in *Synechococcus* sp. PCC 7002 cyanobacteria. For example, introduced transgenes can be targeted to an acsA gene (Locus Tag SynPCC7002_A1831) without the use of a linked antibiotic-resistance gene. Such a strategy is described by Pfleger and Begemann in U.S. application Ser. No. 13/798,835, which is incorporated herein by reference in its entirety. Native *Synechococcus* cyanobacteria that possess a functional acsA gene are killed in the presence of a selective agent; whereas those in which acsA has been inactivated by integration of a transgene construct survive in the presence of the agent. Transgene constructs useful for such a strategy are described herein. Transgene constructs useful for such a strategy are described herein. For example, both the DXS-IspH-IspF construct (FIG. 9), and the temperature regulated lambda cI857-Cro-DXS fusion-IspH-IspF construct (FIG. 12) are designed for targeted insertion into the acsA gene. The complete nucleotide sequence of the DXS-IspH-IspF construct and its flanking regions is shown in SEQ ID NO:23.

In some cases, the Pfleger-Begemann acsA strategy is useful for replacing antibiotic resistance genes that were used as the initial, selective markers for introduced transgenes. The transgene targeting strategy includes placing an acsA gene adjacent to an antibiotic resistance gene. Such a transgene-acsA construct can be targeted to a plasmid or chromosomal site in a *Synechococcus* sp. PCC 7002 strain lacking its chromosomal acsA gene. After selection for antibiotic resistance and replacement of the target DNA, another DNA segment is introduced that can replace both the antibiotic resistance gene and acsA gene through homologous recombination. Selection for growth in the presence of the acsA killing reagent selects for those cells in which the acsA gene has been replaced. This leaves only the desired, introduced transgenes in the cyanobacterial genome.

In some embodiments, promoters that promote increased mRNA transcription can be used to, for example, enhance or regulate IspS and IDI gene expression, or to control expression of additional MEP pathway and isoprenoid synthesis genes to introduced into *Synechococcus* sp. PCC 7002. Highly active promoters appropriate for the methods described herein include the *Synechocystis* sp. PCC 6803 psbA2 and cpeC promoters. See, e.g., Xu et al., Photosynth. Res. Protocols 684:273-293 (2010).

The present invention also provides other strains of *Synechococcus* cyanobacteria, as well as strains of unicellular cyanobacteria and $N_2$-fixing cyanobacteria such as *Anabaena* sp., *Nostoc* sp., *Calothrix* (*Fremyella*) sp., or *Cyanothece* sp., having genetic modifications to express unique combinations of MEP pathway enzymes for increased isoprene production.

Methods for Isoprenoid Production

In another aspect, the present invention provides methods for using a transgenic *Synechococcus* cyanobacterium described herein for producing isoprene. In one embodiment, a method of isoprene production comprises obtaining a host transgenic *Synechococcus* sp. PCC 7002 cyanobacterium comprising transgenes encoding isopentenyl diphosphate isomerase (IDI) and isoprene synthase (IspS); and observing the production of isoprene by the cyanobacterium, where isoprene is produced according to the methods provided herein at a rate of at least about 330 μg per gram dry weight (gDW) per hour ($gDW^{-1}$ $h^{-1}$), at least about 660 μg $gDW^{-1}$ $h^{-1}$, at least about 1200 μg $gDW^{-1}$ $h^{-1}$, and at least about 1600 μg $gDW^{-1}$ $h^{-1}$. These rates are equivalent to about 330 μg $L^{-1}$ $h^{-1}$, at least about 660 μg $L^{-1}$ $h^{-1}$, at least about 1200 μg $L^{1}$ $h^{-1}$, and at least about 1600 μg $L^{-1}$ $h^{-1}$. In certain embodiments, isoprene is produced according to the methods provided herein at a rate of at least about 660 μg $L^{-1}$ $h^{-1}$, at least about 1200 μg $L^{1}$ $h^{-1}$, and at least about 1600 μg $L^{-1}$ $h^{-1}$.

In some cases, a method for producing isoprene comprises obtaining a transgenic *Synechococcus* sp. PCC 7002 cyanobacterium further comprising at least one transgene selected from the group consisting of a transgene encoding DXS, DXR, or IspH (HDR). In such cases, isoprene is produced according to the methods provided herein at a rate of at least about 1000 μg $L^{-1}$ $h^{-1}$. In other cases, isoprene is produced according to the methods provided herein at a rate of at least about 2000 μg $L^{-1}$ $h^{-1}$. In some cases, isoprene is produced at a rate of at least about 1000 μg $L^{1}$ $h^{-1}$, at least about 1200 μg $L^{1}$ $h^{-1}$, at least about 1400 μg $L^{1}$ $h^{-1}$, at least about 1600 μg $L^{1}$ $h^{-1}$, at least about 1800 μg $L^{1}$ $h^{-1}$, at least about 2000 μg $L^{1}$ $h^{-1}$, or more.

In some cases, a method for producing isoprene comprises obtaining a transgenic *Synechococcus* sp. PCC 7002 cyanobacterium in which apc (allophycocyanin) and/or cpc (plastocyanin) genes for light-harvesting phycobilisome complexes or a gene for chlorophyll biosynthesis have been genetically inactivated. Minimization of light-harvesting capacity can prevent self-shading of cyanobacterial cells in culture and permit growth to higher cell densities at high light intensities, thereby increasing product production per culture volume. Such transgenic cyanobacteria will have reduced light-harvesting capacity relative to cyanobacteria in which apc, cpc, and/or a gene for chlorophyll biosynthesis are not inactivated. Light will penetrate deeper into cultures of such transgenic cyanobacteria and, therefore, the transgenic cyanobacteria can be cultured at higher cell densities (e.g., Melis, *Plant Science* 177:272 (2009)), allowing for higher volumetric rates of isoprenoid production. In such cases, transgenic cyanobacteria with one or more inactivated light-harvesting structures are expected to produce isoprene according to the methods provided herein at a rate of at least about 1000 μg $L^{-1}$ $h^{-1}$-2000 μg $L^{-1}$ $h^{-1}$. In some cases, such transgenic cyanobacteria are expected to produce isoprene according to the methods provided herein at a rate of at least about 1000 μg $L^{1}$ $h^{-1}$, at least about 1200 μg $L^{1}$ $h^{-1}$, at least about 1400 μg $L^{1}$ $h^{-1}$, at least about 1600 μg $L^{1}$ $h^{-1}$, at least about 1800 μg $L^{1}$ $h^{-1}$, at least about 2000 μg $L^{1}$ $h^{-1}$, or more.

In some cases, a method for producing isoprene comprises obtaining a transgenic *Synechococcus* sp. PCC 7002 cyanobacterium in which genes for competing carbon utilization pathways have been inactivated. An estimated 80% of the carbon flux in cyanobacteria is devoted to synthesis of glycogen storage carbohydrates. (Lindberg et al., *Metabolic Engineering* 12:70 (2010)). Inactivation of a glycogen synthase gene or a combination of glycogen synthase and soluble sugar synthase genes can reduce or eliminate this flow, thereby increasing carbon flow into the MEP pathway for isoprenoid production. Accordingly, the glgA1 (Locus Tag SynPCC7002_A1532) and glgA2 (Locus Tag SynPCC7002_A2125) genes, which encode glycogen synthases, have been genetically inactivated. In such cases, cyanobacteria having at least one gene encoding glgA1 or glgA2 inactivated (either alone or in combination with inactivated genes for soluble sugar synthesis such as glgC (for ADP-Glucose pyrophosphorylase, Locus Tag SynPCC7002_A0095), and/or spsA (for sucrose phosphate synthase, Locus Tag SynPCC7002_A0888), and/or combinations of gpgS, gpgP, ggpS, ggpP (for glucosylglycerate and glucosylglycerol synthesis, Locus Tags _A2021, _A2022, _A2851, and _A2841) are expected to produce isoprene according to the methods provided herein at a rate of at least about 1000 μg $L^{-1}$ $h^{-1}$ and, in some cases, at least about 2000 μg $L^{-1}$ $h^{-1}$.

Accordingly, another aspect of the present invention includes methods for producing isoprene, where the methods comprise obtaining a transgenic *Synechococcus* sp. PCC 7002 cyanobacterium comprising codon-optimized IspS and IDI genes and further comprising (1) at least one transgene that encodes a MEP pathway component (e.g., DXS, DXR, IspH) and (2) one or more transgenes that encodes an inactivated light-harvesting complex. With an inactivated light-harvesting complex, carbon flow to the MEP pathway is increased. According to the methods described herein, such transgenic cyanobacteria are expected to produce isoprene at a rate of at least about 1000 μg $L^{-1}$ $h^{-1}$, at least about 2000 μg $L^{-1}$ $h^{-1}$, or at least about 4000 μg $L^{-1}$ $h^{-1}$.

In some cases, a method for producing isoprene comprises obtaining a transgenic *Synechococcus* sp. PCC 7002 cyanobacterium, which carries codon-optimized IspS and IDI genes, together with at least one transgene encoding at least one of DXS, DXR, and IspH (HDR), together with one or more transgenes encoding an inactivated light-harvesting antenna complexes, together with inactivated glgA1 and/or glgA2 genes for glycogen synthesis, and/or an inactivated enzyme required for sucrose synthesis and/or glucosylglycerol(ate) synthesis. According to the methods described herein, such transgenic cyanobacteria are expected to produce isoprene according to the methods provided herein at a rate of at least about 1000 μg $L^{-1}$ $h^{-1}$, at least about 2000 μg $L^{-1}$ $h^{-1}$, at least about 4000 μg $L^{-1}$ $h^{-1}$, or at least about 8000 μg $L^{-1}$ $h^{-1}$.

In another aspect, methods of the present invention are also drawn to producing isoprene using a transgenic *Synechococcus* sp. PCC 7002 cyanobacterium comprising codon-optimized IspS and IDI genes and further comprising one or more transgenes encoding at least one inactivated sugar synthesis enzyme selected from the group consisting of glgC (ADP-Glucose pyrophosphorylase, Locus Tag _A0095), spsA (sucrose phosphate synthase A, _A0888), gpgS (glucosyl-3-phosphoglycerate synthase, _A2021), gpgP (glucosyl-3-phosphoglycerate phosphatase, _A2022), ggpS (glucosylglycerol-phosphate synthase, A2851), and ggpP (glucosylglycerol-phosphate phosphatase, A2841). In some cases, a transgenic cyanobacterium can comprise one or more transgenes encoding a combination of inactivated sugar synthesis enzymes including, without limitation, inactivated gpgS+inactivated gpgP or inactivated ggpS+inactivated ggpP.

In a further aspect, the present invention provides methods for using a transgenic *Synechococcus* cyanobacterium described herein for producing pinene. In one embodiment, a method of pinene production comprises obtaining a host transgenic *Synechococcus* sp. PCC 7002 cyanobacterium comprising transgenes encoding geranyl diphosphate synthase (GPPS) and mono-terpene synthase (mono-TPS); and observing the production of pinene by the cyanobacterium, where pinene is produced at a rate of at least about 330 μg per gram dry weight (gDW) per hour (e.g., at least about 330 μg $gDW^{-1}$ $h^{-1}$, at least about 660 μg $gDW^{-1}$ $h^{-1}$, at least about 1200 μg $gDW^{-1}$ $h^{-1}$, at least about 1600 μg $gDW^{-1}$ $h^{-1}$). These rates are equivalent to about 330 μg $L^{-1}$ $h^{-1}$ (e.g. at least about 330 μg $L^{-1}$ $h^{-1}$, at least about 660 μg $L^{-1}$ $h^{-1}$, at least about 1200 μg $L^{-1}$ $h^{-1}$, at least about 1600 μg $L^{-1}$ $h^{-1}$).

In some cases, a method for producing pinene comprises obtaining a transgenic *Synechococcus* sp. PCC 7002 cyanobacterium, which carries codon-optimized geranyl diphosphate synthase (GPPS) (SEQ ID NO:3) and mono-terpene synthase (mono-TPS), together with any combination of transgenes encoding DXS, DXR, or IspH (HDR), or with inactivated glgA1 and/or glgA2 genes for glycogen synthesis, and/or with genes for inactivated light-harvesting antenna complexes. Nucleotide and encoded amino acid sequences of a *Abies grandis* geranyl diphosphate synthase (GPPS1) gene optimized for mRNA secondary structure and codon-usage in *Synechococcus* sp. PCC 7002 cyanobacteria are set forth in SEQ ID NO:3 and SEQ ID NO:4, respectively. In such cases, the transgenic cyanobacteria are expected to produce pinene according to the methods provided herein at a rate of at least about 1000 μg $L^{-1}$ $h^{-1}$-2000 μg $L^{-1}$ $h^{-1}$. In some cases, the transgenic cyanobacteria are expected to produce pinene according to the methods provided herein at a rate of at least about 4000 μg $L^{-1}$ $h^{-1}$-8000 μg $L^{-1}$ $h^{-1}$.

The methods provided herein can comprise cultivating isoprene-producing and/or pinene-producing *Synechococcus* cyanobacteria under high $CO_2$ conditions. High $CO_2$ conditions can comprise up to 100% $CO_2$ atmospheric conditions. For example, isoprene-producing or pinene-producing *Synechococcus* cyanobacteria can be grown in enclosed bioreactors containing $CO_2$-saturated growth medium and up to 100% $CO_2$ in the head-space.

For experimental purposes, transgenic cyanobacteria can be cultured in small 100-150 mL cultures in marine A medium (Buzby et al., *Science* 230:805 (1985)) to exponential phase (O.D. 750 nm 0.5) or stationary phase (O.D. 750 nm ~4) at moderate light intensity (e.g., approximately 200 μmol $m^{-2}s^{-1}$) in enclosed bioreactors containing $CO_2$-saturated growth medium and up to 100% $CO_2$ in the head-space. Transgenic *Synechococcus* sp. PCC 7002 cyanobacteria can grow to cell densities of 10 O.D. 750 nm (approximately 2.2 gDW $L^{-1}$) (FIG. 21). Transgenic cyanobacteria carrying inactivated genes for light-harvesting are expected to grow to higher densities up to 15-20 10 O.D. 750 nm (approximately 3.3 to 4.4 gDW $L^{-1}$).

Culture vessels can be equipped for sampling to measure cell density, photosynthesis parameters, and head-space sampling for isoprene measurements by gas chromatography-mass spectrometry (GC-MS). Larger 1 to 5 Liter culture vessels (fermenters) can be used for the same measurements as above, and to monitor and record parameters such as pH, $O_2$, and cell density. Optimal growth and isoprenoid production in 100% $CO_2$ will require pH monitoring. 100% $CO_2$ gas can be pumped into cultures until the pH drops to approximately 6.5. At that point, $CO_2$ flow is stopped and the culture vessel sealed. Photosynthetic carbon fixation by the cyanobacteria will consume $CO_2$ and thus raise the culture pH. When the pH rises to a selected value, e.g. pH 7.5, the culture system can be programmed to deliver a fresh supply of $CO_2$, again until the pH drops to approximately 6.5.

Figure 22:
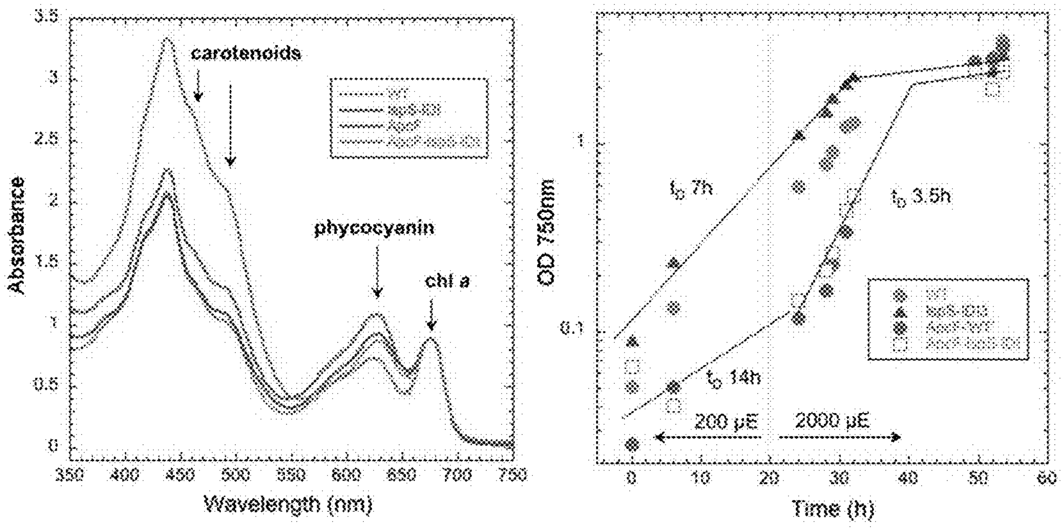
FIG. 22 presents absorbance spectra and growth curves for *Synechococcus* sp. PCC ΔApcF, light-harvesting mutants and control strains. (A) Spectra of cell lysates from ΔApcF (ApcF-'WT') and ΔApcF (IspS-IDI) strains grown to a high cell density (OD 750 nm ~3) show that both strains still contained phycobilisomes as indicated by the phycocyanin (PC) peak at ~620 nm. ΔApcF mutants had a higher carotenoid content relative to wild-type. (B) ΔApcF mutants grew slowly at a light intensity of approximately 200 μmol photons $m^{-2}$ $s^{-1}$, which is consistent with impaired light harvesting. The ΔApcF mutants grew very rapidly (~3.5 hour doubling times) as compared to wild type or IspS-IDI strains when shifted to a high light intensity of 2000 μmol photons $m^{-2}$ $s^{-1}$ (i.e., full sunlight).

The methods provided herein can comprise cultivating isoprene-producing or pinene-producing transgenic *Synechococcus* cyanobacteria under light and dark conditions. For example, a method of isoprene production can comprise subjecting the cyanobacterium to one or more light-dark cycles. A light-dark cycle can include an illumination period that comprises full intensity (continuous or fluctuating) sunlight or artificial conditions approximating full intensity sunlight or 2× full intensity sunlight (e.g., 4000-5000 μmol photons $m^{-2}$ $s^{-1}$). In some cases, transgenic *Synechococcus* cyanobacteria are subjected to natural day-night cycles. In such cases, an illumination period of the cycle can comprise full intensity sunlight. For commercial applications, it is expected that isoprenoid-producing, transgenic, *Synechococcus* sp. PCC 7002 cyanobacteria will be grown in enclosed photobioreactors in natural day-night cycles. Because these cyanobacteria are a marine, euryhaline species (i.e., tolerant to a wide range of salt concentrations), they are well suited for growth in saline, waste waters, e.g., from municipal or industrial sources, or from agricultural irrigation in arid regions of the world. Rapid growth of *Synechococcus* sp. PCC 7002 at >2× full intensity sunlight is well established (Nomura et al., Archives Microbiology 185:471 (2006)) and makes this cyanobacterium ideally suited as a host for solar energy driven bioproduct-biofuels production. As described herein, a ΔapcF, allophycocyanin light-harvesting mutant of *Synechococcus* sp. PCC 7002 (obtained using the methods provided herein) grew very well at a light-intensity equivalent to full sunlight (about 2000 μmol photons $m^{-2}$ $s^{-1}$) with a doubling time of approximately 3.5 hours (see FIG. 22).

Any appropriate method for observing isoprene and pinene production can be used according to the present invention. Isoprene accumulates in the head space of culture vessels and can be readily measured and quantified against standard isoprene by gas chromatography (GC) with a flame ionization detector (FID) or photo-ionization (PID) detector and a column for short-chain hydrocarbons, or by gas chromatography-mass spectrometry (GC-MS). In some embodiments, observing isoprene production comprises periodically sampling vessel head spaces to determine rates of isoprene synthesis. DMAPP levels can be assessed by an established method involving acidification of cell extracts, which converts a fixed fraction of DMAPP into isoprene that can then be measured by GC-FID or GC-MS. Observing production of pinene (a volatile liquid) can include obtaining culture head space samples or hexane extraction samples and assaying for pinene by GC-MS. In some cases, continuous and sensitive real-time monitoring of isoprene in cyanobacterial gas-effluent streams can be made using a Fast Isoprene Sensor (FIS) (Hills-Scientific, Boulder, Colo.). Carbon dioxide and gas-phase metabolites in culture inlet and effluent gases can be measured by an infrared gas analyzer (IRGA). Membrane inlet mass spectrometry (MIMS) also can be used to simultaneously quantify net $CO_2$ exchange, $O_2$ release, and $O_2$ uptake. Photosynthetic electron transfer rates and fluorescence parameters in, for example, isoprene-producing and control cyanobacterial cultures can be measured using a pump-probe kinetics spectrophotometer (BioLogic JTS-10) or a pulse-modulated chlorophyll fluorimeter (WALZ PAM-100 or similar).

In some cases, the methods provided herein can further include capturing one or both of isoprene and pinene from a transgenic *Synechococcus* sp. PCC 7002 cyanobacterial culture. As described herein, any appropriate method of capturing isoprene and pinene from a cyanobacterial culture can be used. Isoprene can be captured from a nitrogen or air gas stream, which is bubbled through a culture of isoprene-producing cyanobacteria of the present invention. This may be done by means of a cell-culture system with a built-in gas sparger. Exemplary methods of capturing isoprene from a cyanobacterial culture include, without limitation, distillation, adsorption onto a polymer membrane, and filtration using a filter gas purifier. These methods may be used individually or in combination to obtain high purity liquid isoprene. In some cases, isoprene capture can be followed by GC-MS analysis.

A method of capturing pinene from a cyanobacterial culture is hexane extraction. In some cases, hexane extraction is followed by GC-MS analysis. In large-scale cyanobacterial cultures, pinene will float on the top of the cultures and can be separated according to any appropriate method.

Additional methods for capturing isoprenoids include adsorption onto polymer-modified activated carbon, isopar oils (Dupont), or C18 matrices followed by extractive distillation or thermal desorption. Isoprene can be dimerized to limonene (a liquid isoprenoid, and high-density biofuel) on polymer-activated carbon at 150-200° C. The isoprenoids can be released at higher temperatures or by elution with organic solvents.

Various exemplary embodiments of compositions and methods according to this invention are now described in the following examples. The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Figure 2:
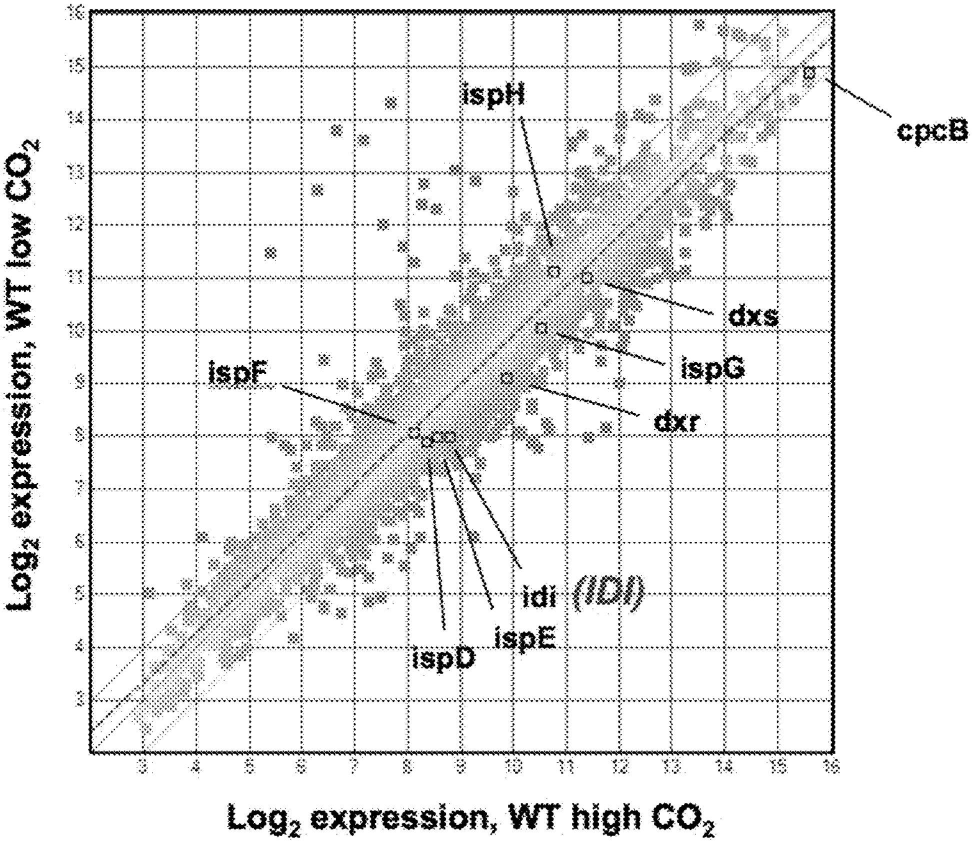
FIG. 2 presents global gene expression profiles from microarrays of *Synechococcus* sp. PCC 7002 cyanobacteria grown under ambient and high $CO_2$ conditions. Microarrays were performed to obtain whole-genome gene expression profiles for *Synechococcus* sp. PCC 7002 cyanobacteria grown in low (0.04%) ambient $CO_2$ relative to cells grown in high (3%) $CO_2$. Each data point represents the mean expression level (from triplicate samples) of one of the ~3200 genes in the genome. The expression of MEP pathway genes did not differ significantly between these two conditions, but these and other data reveal that several of the MEP pathway genes are expressed at low levels. One of these is the native IDI gene for a key, rate-limiting IPP-DMAPP isomerase. High-level expression of poplar IDI, together with IspS, from a strong cyanobacterial promoter enabled active isoprene production in these cyanobacteria. Shown for comparison is the highly expressed cpcB gene for the 13-subunit of the light-harvesting c-phycocyanin protein. A version of the cpcB promoter has been used to drive high-level expression of introduced IspS and IDI genes.

Global Gene Expression Analysis of *Synechococcus* sp. PCC 7002 Strains Under Diverse Growth Conditions Several microarray studies were performed to analyze whole-genome gene expression responses in *Synechococcus* sp. PCC 7002 cyanobacteria (wild-type and mutant strains) grown under a variety of environmental conditions. For example, data were obtained for cells grown under low, ambient $CO_2$ conditions and under high (3%) $CO_2$ conditions (FIG. 2). Data sets have been obtained from a total of 76 high-density microarray experiments, representing messenger RNAs from *Synechococcus* sp. PCC 7002 grown at optimal and high light intensities, ambient and high $CO_2$, dark aerobic and anaerobic conditions, iron starvation, and from several iron and stress-response regulator mutants. Further global gene-expression studies can be conducted using, for example, additional microarray analyses or RNA sequencing methods (see, e.g., Ludwig and Bryant, *Frontiers Microbiology* 3:1-14 (2012)).

The microarrays included high-density probes for upstream untranslated regions (UTRs) to map transcription start sites and define operons and promoter regions for all genes in the genome. Genes highly expressed in the microarrays, therefore, identified promoter regions potentially useful for obtaining high-level expression of introduced genes. Table 1 provides a list of genes that are highly expressed genes in *Synechococcus* sp. PCC 7002 grown at high (3%) $CO_2$ and different light intensities (for example, 200 μmol $m^{-2}$ $s^{-1}$ and 2000 μmol $m^{-2}$ $s^{-1}$). The promoter regions of these genes when derived from *Synechococcus* sp. PCC 7002 or other cyanobacteria might be used to drive active, high-level expression of genes encoding components of the MEP pathway and isoprenoid synthesis pathways.

TABLE 1

Highly Expressed Genes Under Diverse Light Intensity Conditions

| GENE ID | GENE NAME | DESCRIPTION | log2, WT, 3% $CO_2$ | log2, WT, 3% $CO_2$, HLT |
|---|---|---|---|---|
| SYNPCC7002_A0032 | | | 15.83653 | 15.81852 |
| SYNPCC7002_A0106 | gap | glyceradehyde-3-dehydrogenase, type 1 | 14.12389 | 14.31405 |
| SYNPCC7002_A0135 | psbZ | Photosystem II subunit PsbZ | 14.55428 | 15.17058 |
| SYNPCC7002_A0167 | petJ | Cytochrome c6 (Cytochrome c553) | 15.13937 | 15.14978 |
| SYNPCC7002_A0230 | psbE | cytochrome b559,alpha subunit (Photosystem II subunit PsbE) | 14.80816 | 15.22279 |
| SYNPCC7002_A0231 | psbF | cytochrome b559, beta subunit (Photosystem II subunit PsbF) | 14.38169 | 14.83004 |
| SYNPCC7002_A0232 | psbL | Photosystem II subunit PsbL | 14.52945 | 15.06825 |
| SYNPCC7002_A0242 | sodB | Mn-superoxide dismutase | 14.11571 | 14.25417 |
| SYNPCC7002_A0246 | gin | glutamine synthetase type III | 14.26789 | 14.45782 |
| SYNPCC7002_A0269 | psbO | photosystem II manganese stabilizing protein PsbO | 14.57481 | 14.43321 |
| SYNPCC7002_A0322 | psbU | Photosystem II 12 kDa extrinsic protein (PsbU) | 14.64241 | 14.64064 |
| SYNPCC7002_A0489 | rpmA | ribosomal protein L27 | 13.89388 | 14.73745 |
| SYNPCC7002_A0682 | psaD | photosystem I subunit II | 15.20196 | 14.58616 |
| SYNPCC7002_A0734 | atpA | ATP synthase F1, alpha subunit | 14.2905 | 14.28118 |
| SYNPCC7002_A0735 | atpH | ATP synthase F1, delta subunit | 13.89203 | 13.90982 |
| SYNPCC7002_A0736 | atpF | ATP synthase B chain (Subunit I) | 14.18096 | 13.97439 |
| SYNPCC7002_A0738 | atpE | ATP synthase C chain (Lipid-binding protein) | 15.07833 | 15.2894 |
| SYNPCC7002_A0739 | atpB | ATP synthase F0, A subunit | 14.68326 | 14.89041 |
| SYNPCC7002_A0740 | atp1 | ATP synthase subunit I | 14.96289 | 14.99414 |
| SYNPCC7002_A0749 | atpD | ATP synthase beta chain | 13.95872 | 14.18191 |

TABLE 1-continued

Highly Expressed Genes Under Diverse Light Intensity Conditions

| GENE ID | GENE NAME | DESCRIPTION | log2, WT, 3% $CO_2$ | log2, WT, 3% $CO_2$, HLT |
|---|---|---|---|---|
| SYNPCC7002_A0793 | N/A | AhpC/TSA family protein | 13.96553 | 14.57938 |
| SYNPCC7002_A0811 | cpcG | Phycobilisome rod-core linker polypeptide cpcG (L-RC 28.5) | 15.22332 | 14.96004 |
| SYNPCC7002_A0841 | petD | cytb6/f complex subunit IV | 14.81309 | 15.25553 |
| SYNPCC7002_A0842 | petB | cytochrome b6 | 14.64322 | 15.42215 |
| SYNPCC7002_A0957 | psbT | Photosystem II reaction center, PsbT protein | 15.69627 | 15.5891 |
| SYNPCC7002_A0981 | ycf12 | conserved hypothetical protein Ycf12 | 14.11484 | 14.13577 |
| SYNPCC7002_A1008 | psaF | photosystem I reaction center subunit II, PsaF | 14.78339 | 14.50609 |
| SYNPCC7002_A1026 | rplL | ribosomal protein L7/L12 | 13.85186 | 14.02581 |
| SYNPCC7002_A1027 | rpl10 | 50S ribosomal protein L10 | 14.1209 | 14.06374 |
| SYNPCC7002_A1031 | secE | preprotein translocase, SecE subunit | 14.05308 | 14.39619 |
| SYNPCC7002_A1044 | rpsM | ribosomal protein S13 | 13.86824 | 13.98057 |
| SYNPCC7002_A1058 | rplP | ribosomal protein L16 | 14.14127 | 14.1662 |
| SYNPCC7002_A1060 | rplV | ribosomal protein L22 | 14.02709 | 13.88103 |
| SYNPCC7002_A1233 | N/A | lipoprotein, putative | 13.86872 | 15.30694 |
| SYNPCC7002_A1285 | glnB | Nitrogen regulatory protein P-II | 13.88815 | 14.47371 |
| SYNPCC7002_A1313 | narK | nitrate transporter | 14.17042 | 14.69205 |
| SYNPCC7002_A1347 | N/A | photosystem II PsbY protein | 14.2329 | 14.48732 |
| SYNPCC7002_A1352 | Fba | fructose-bisphosphate aldolase, class II, Calvin cycle subtype | 14.10756 | 14.83667 |
| SYNPCC7002_A1393 | psaE | photosystem I reaction center subunit IV | 15.26565 | 14.59262 |
| SYNPCC7002_A1395 | | | 15.92843 | 15.89186 |
| SYNPCC7002_A1398 | | | 15.91689 | 15.85669 |
| SYNPCC7002_A1399 | | | 14.6606 | 15.25291 |
| SYNPCC7002_A1418 | psbA | photosystem q(b) protein | 15.5062 | 15.81899 |
| SYNPCC7002_A1559 | psbC | photosystem II 44 kDa subunit reaction center protein | 14.99019 | 15.48355 |
| SYNPCC7002_A1560 | psbD | photosystem II D2 protein (photosystem q(a) protein) | 15.38761 | 15.77398 |
| SYNPCC7002_A1589 | psaC | photosystem I iron-sulfur center subunit VII | 14.40936 | 13.75351 |
| SYNPCC7002_A1605 | N/A | hypothetical protein | 14.06539 | 14.1292 |
| SYNPCC7002_A1614 | Trx | thioredoxin | 14.37063 | 14.18893 |
| SYNPCC7002_A1759 | psbB | photosystem II protein | 14.87053 | 15.2034 |
| SYNPCC7002_A1796 | rbcS | Ribulose bisphosphate carboxylase, small subunit | 14.38815 | 14.59373 |
| SYNPCC7002_A1797 | rbcX | RbcX protein, possible rubisco chaperone | 15.30789 | 15.28725 |
| SYNPCC7002_A1798 | rbcL | ribulose-1,5-bisphosphate carboxylase, large subunit | 15.04828 | 15.37442 |
| SYNPCC7002_A1801 | ccmL | carbon dioxide concentrating mechanism protein | 13.8251 | 14.34093 |
| SYNPCC7002_A1802 | ccmK | Carbon dioxide concentrating mechanism protein | 14.19422 | 14.87962 |
| SYNPCC7002_A1803 | ccmK | carbon dioxide concentrating mechanism protein | 14.15719 | 14.99849 |
| SYNPCC7002_A1893 | rpmF | ribosomal protein L32 | 13.63403 | 14.29482 |
| SYNPCC7002_A1909 | petC | Rieske FeS protein | 13.87228 | 14.00427 |
| SYNPCC7002_A1928 | apcC | aliophycocyamin-associated phycobilisome 7.8 kDa core-linker pol | 15.1539 | 14.68701 |
| SYNPCC7002_A1929 | apcB | aliophycocyamin, beta subunit | 15.69597 | 15.73533 |
| SYNPCC7002_A1930 | apcA | aliophycocyamin alpha subunit | 15.73675 | 15.70621 |
| SYNPCC7002_A1961 | psaA | Photosystem I P700 chlorophyll A apoprotein A1 | 15.75197 | 15.65849 |
| SYNPCC7002_A1962 | psaB | photosystem I protein A2 | 15.53234 | 15.43821 |
| SYNPCC7002_A1965 | N/A | DNA-binding protein HU | 14.701 | 14.0354 |
| SYNPCC7002_A2009 | apcE | phycobilisome core-membrane linker phycobiliprotein ApcE | 14.53541 | 14.02525 |
| SYNPCC7002_A2061 | Tuf | translation elongation factor Tu | 14.62049 | 15.23139 |
| SYNPCC7002_A2062 | fusA | translation elongation factor G | 13.70922 | 14.30685 |
| SYNPCC7002_A2064 | rpsL | 30S ribosomal protein S12 | 13.96441 | 14.18645 |
| SYNPCC7002_A2151 | psbM | photosystem II reaction centre M protein | 14.02823 | 14.12322 |
| SYNPCC7002_A2177 | N/A | hypothetical protein | 14.6033 | 14.71203 |
| SYNPCC7002_A2199 | psbD | photosystem II D2 protein | 15.50601 | 15.70198 |
| SYNPCC7002_A2208 | N/A | ammonium/methylammonium permease | 14.8346 | 15.03224 |
| SYNPCC7002-A2209 | cpcB | phycocyanin, beta subunit | 15.88389 | 15.76497 |
| SYNPCC7002_A2210 | cpcA | phycocyanin, alpha subunit | 15.86755 | 15.65395 |

TABLE 1-continued

| Highly Expressed Genes Under Diverse Light Intensity Conditions | | | | |
|---|---|---|---|---|
| GENE ID | GENE NAME | DESCRIPTION | log2, WT, 3% $CO_2$ | log2, WT, 3% $CO_2$, HLT |
| SYNPCC7002_A2326 | petF | ferredoxin I (2Fe-25) | 14.76666 | 14.98905 |
| SYNPCC7002_A2476 | chIP | geranylgeranyl reductase | 13.94225 | 13.93118 |
| SYNPCC7002_A2531 | N/A | hypothetical protein | 14.18043 | 14.25335 |
| SYNPCC7002_A2579 | N/A | hypothetical protein | 13.43055 | 14.8614 |
| SYNPCC7002_A2620 | psaI | photosystem I reaction center subunit XI | 15.47607 | 14.70786 |
| SYNPCC7002_A2621 | N/A | Photosystem I reaction center subunit VIII | 14.68393 | 13.42949 |
| SYNPCC7002_A2779 | N/A | Photosystem II 4 kDa reaction center component superfamily | 14.35598 | 15.11529 |

Example 2

Figure 3:
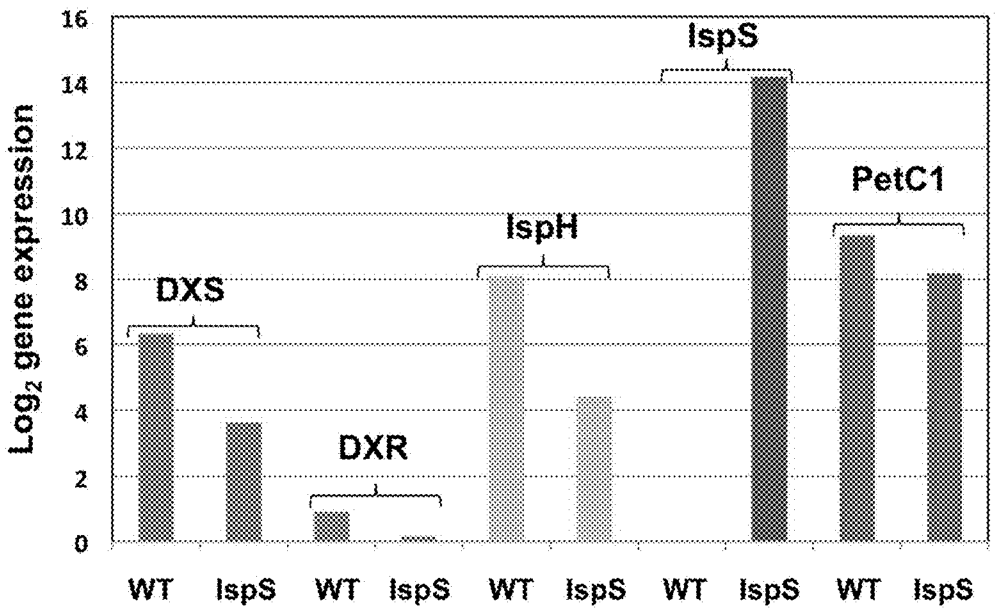
FIG. 3 shows a graph of reverse transcriptase quantitative PCR (RT-qPCR) data showing expression levels of an introduced native poplar IspS gene (not yet codon optimized) and selected MEP pathway genes in *Synechococcus*. Expression levels are shown for the native MEP pathway genes DXS, DXR, and IspH in wild-type (control) *Synechococcus* and in a recombinant strain (IspS) carrying the poplar IspS gene under control of the PcpcB promoter. Expression levels were compared against PetC1, a highly expressed photosynthetic electron transport gene. Gene expression levels are shown as $\log_2$ values; gene expression at $\log_2$=14 (or $2^{14}$) is $2^6$, or 64-fold higher than expression at $\log_2$=8 (or $2^8$). Thus, the introduced IspS gene was expressed at a very high level from the *Synechocystis* sp. PCC 6803 PcpcB promoter.
Figure 8:
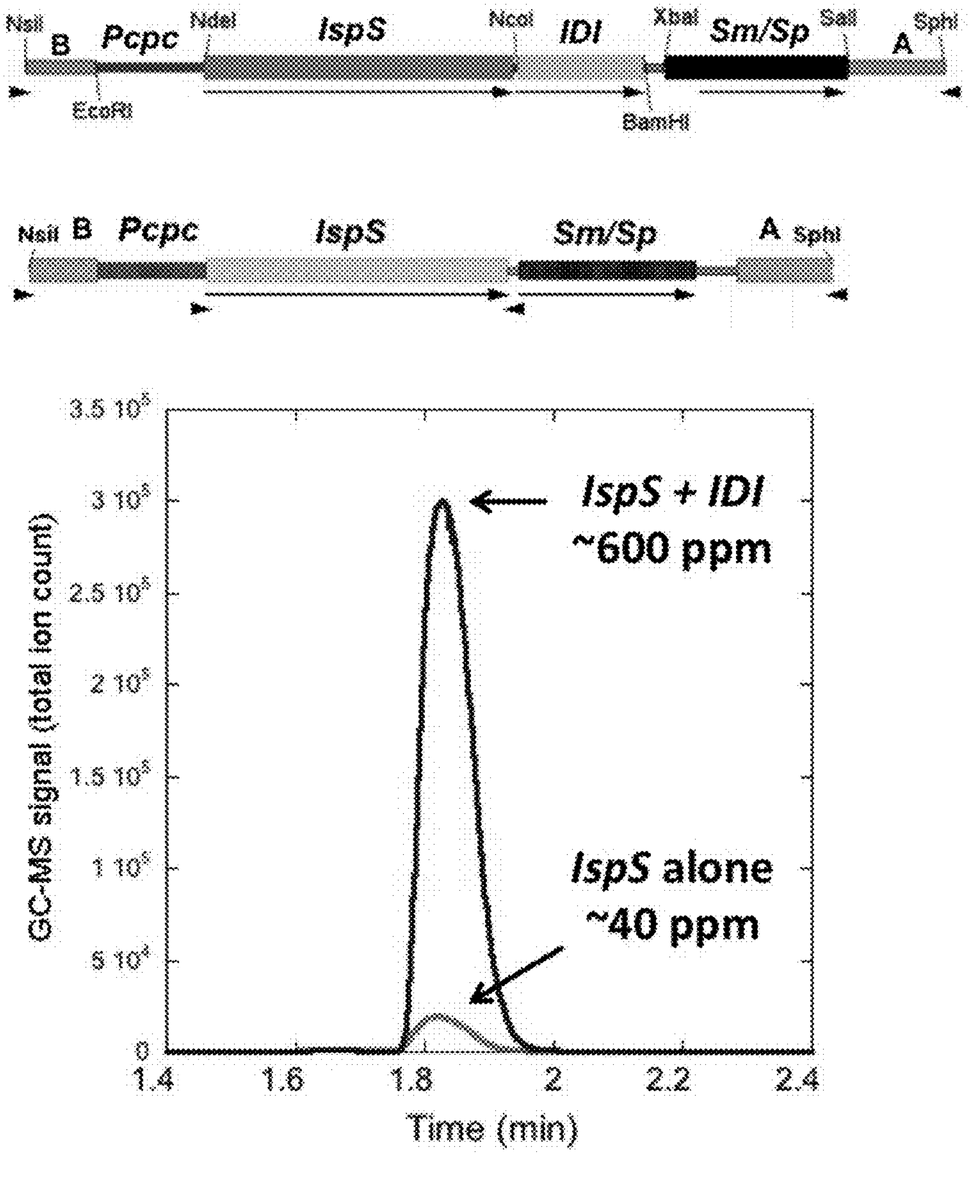
FIG. 8 presents maps of IspS-IDI and IspS gene targeting constructs as well as GC-MS analysis of isoprene yields in *Synechococcus* sp. PCC 7002 strains that carry and express these gene sets. The isoprene yield was approximately 15-fold higher in the strain carrying both the mRNA secondary structure and codon-optimized IPP-DMAPP isomerase (IDI) and isoprene synthase (IspS) genes relative to a strain carrying the optimized IspS gene alone.

Gene Expression and Isoprene Production in Control and Recombinant *Synechococcus* Strains As shown in FIG. 3, RT-qPCR was performed to analyze the expression of poplar PIspS and native MEP pathway DXS, DXR, and IspH genes in control and recombinant *Synechococcus* strains. The introduced PIspS gene was expressed at a very high level—approximately 16-fold higher than PetC1, which encodes a major photosynthesis protein. Despite high expression of IspS genes at the mRNA level, isoprene production was not detected in *Synechococcus* sp. PCC 7002 cyanobacteria carrying only an introduced, native (non codon-optimized) Poplar PIspS gene. Even an mRNA and codon-optimized PIspS gene, when expressed by itself in the cyanobacteria, produced isoprene at a yield about 15-fold lower than when expressed together with an optimized MEP pathway IDI-DMAPP isomerase, IDI gene (FIG. 8). These data indicate that enzymes in the MEP pathway may limit carbon flux and thus steps that increase carbon flow through this pathway will increase isoprenoid production. Further increases in isoprenoid production rates and yields can be expected by increasing the expression levels of additional MEP pathway genes. Note, for example, that the DXR gene was expressed at quite a low level, especially in the *Synechococcus*-PIspS strain (FIG. 3).

Example 3

Preferred Codons for IspS and IDI-DMAPP Isomerase Genes

Codon optimization for the isoprene synthase (IspS) and IDI-DMAPP isomerase (IDI) genes expressed in *Synechococcus* sp. PCC 7002 was based on Kudla et. al., *Science* 324:255 (2009). Kudla et al. observed that the two most typical measures of codon bias, the Codon Adaptation Index (CAI) and the frequency of optimal codons, did not necessarily correlate with high protein expression levels, and that even rare codons could be used if localized to particular regions of mRNA transcripts. According to Kudla et al., minimizing mRNA secondary structure in the ribosome binding site and −4 to +42 nucleotide region relative to the start of the coding sequence had the most dramatic impact on elevated protein expression. Accordingly, 46 nucleotides of the IspS and IDI genes were "codon optimized" with the aid of a web-based program from Integrated DNA technologies (see the idtdna.com site on the World Wide Web). The program was used to determine and minimize the free energies (ΔG) of mRNA transcripts in the 5' regions of these genes. Using this approach, the most stable mRNA secondary structures in these 5' regions had ΔG values no lower than approximately +0.3 kcal/mol, where negative ΔG values reflect more stable, and thus less desirable, structures.

Codon-optimized IDI (SEQ ID NO:7) and IspS (SEQ ID NO:5) nucleic acid sequences for expression in *Synechococcus* sp. PCC 7002 were based on the *Populus trichocarpa* sequences (ACCESSION No. EU693026, VERSION EU693026.1, GI:189017051 and ACCESSION No. EU693027, VERSION, EU693027.1, GI:189017053 for IDI and IspS, respectively) as modified by Singsaas and Wiberley for expression in *Escherichia coli*. Further modifications of IspS and IDI genes for *Synechococcus* sp. PCC 7002 may be based either on the *Populus* or *E. coli* modified sequences. Amino acid sequences encoded by the above-described codon-optimized nucleic acid sequences for IspS and IDI are set forth in SEQ ID NO:6 and SEQ ID NO:8, respectively.

Example 4

Expression of Codon-Optimized IspS and MEP Pathway Genes in *Synechococcus* sp. PCC 7002

Figure 4:
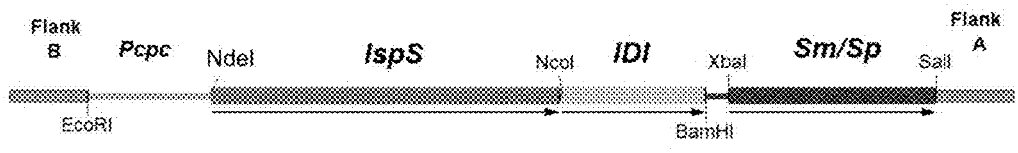
FIG. 4 presents a map of the synthetic, codon-optimized gene construct for expression of isoprene synthase (IspS) (SEQ ID NOS:5-6) and IPP-DMAPP isomerase (IDI) (SEQ ID NOS:7-8) genes in *Synechococcus*. A 5014 base-pair gene construct containing *Populus* IspS and IDI genes codon-optimized for *Synechococcus* sp. PCC 7002 was synthesized. The entire construct contains the IspS and IDI genes and a streptomycin-spectinomycin (Sm/Sp) antibiotic-resistance cassette surrounded by 'Flank B' (before) and 'Flank A' (after) segments for recombination with homologous regions on the endogenous, high-copy pAQ1 plasmid. Expression of both genes is under the control of a strong PcpcB promoter (Pcpc) from the cyanobacterium *Synechocystis* sp. PCC 6803 (FIG. 5, SEQ ID NO:1). A *Synechocystis* promoter was used to avoid unwanted recombination with the endogenous *Synechococcus* 7002 cpcB promoter region.

For expression of IspS and IDI genes in *Synechococcus* sp. 7002 using the constructs presented in FIGS. 4-5, the 601 base-pair sequence containing the *Synechocystis* sp. PCC 6803 cpcB promoter (SEQ ID NO:1) was used. FIG. 6 illustrates a strategy used to target IspS and IDI genes to the high-copy number pAQ1 plasmid of *Synechococcus* sp. PCC 7002.

Figure 7:
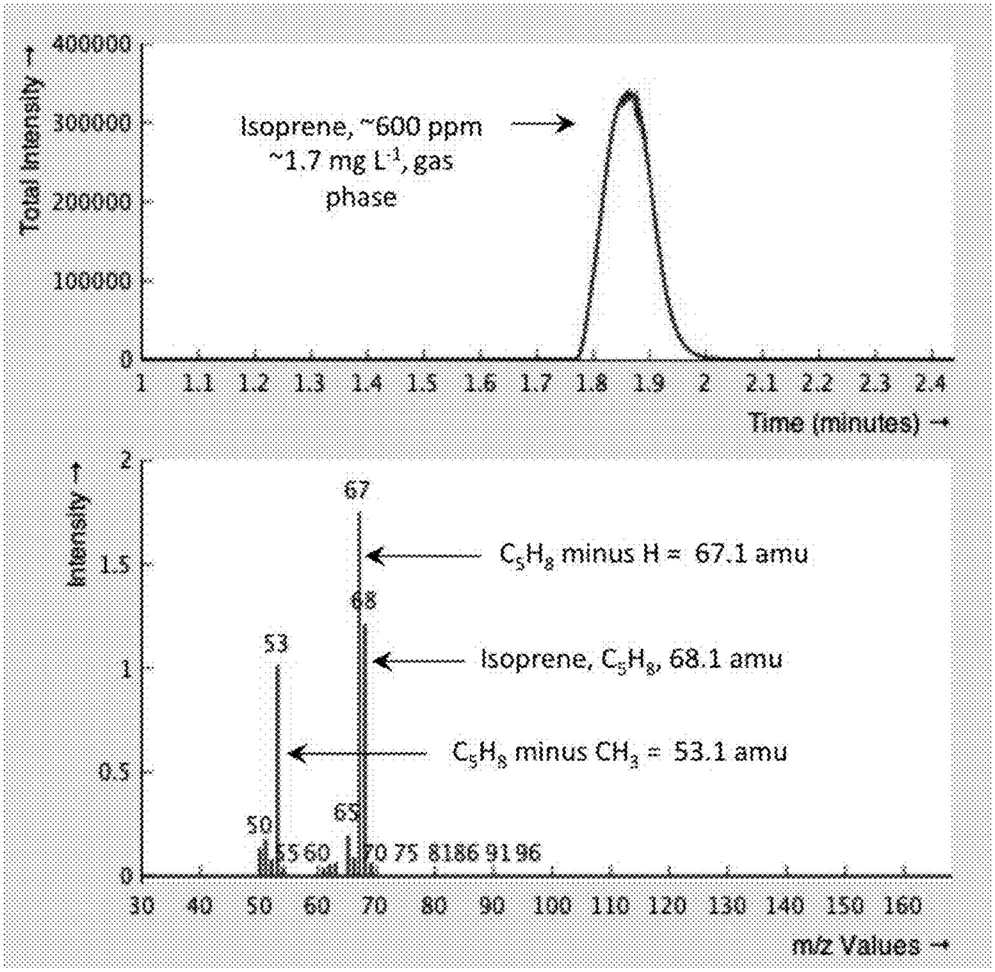
FIG. 7 presents gas chromatography-mass spectrometry (GC-MS) data demonstrating substantial isoprene production in genetically modified *Synechococcus* sp. PCC 7002 cyanobacteria carrying codon-optimized isoprene synthase (IspS, SEQ ID NO:5) and IPP-DMAPP isomerase (IDI, SEQ ID NO:7) genes. (A) GC-MS chromatogram showing a high concentration of isoprene (approximately 600 ppm, or approximately 1.7 mg $L^{-1}$) in the head-space of a *Synechococcus* (IspS-IDI) culture grown under 100% $CO_2$. (B) Fragment ion mass spectrum showing that the GC peak displayed in Panel A contains highly pure isoprene as evidenced by characteristic masses for isoprene (68.1 amu) and its degradation products. Isoprene in the head-space was produced at a rate of approximately 330 μg isoprene $gDW^{-1}$ $h^{-1}$, equivalent to approximately 4 mg $gDW^{-1}$ 12 h $day^{-1}$, which is approximately 80 times higher than any published rate for cyanobacteria.

Previous work with non-photosynthetic bacteria demonstrated that expression of introduced IspS genes alone resulted in little or no detectable synthesis of isoprene in *E. coli*. Reasonable levels of isoprene production were detected only after the introduction of IspS genes together with optimized expression of flux-limiting MEP pathway genes. Thus, a gene construct was designed for expression of IspS and IDI genes, codon-optimized for efficient mRNA secondary structure and protein synthesis in *Synechococcus* sp. PCC 7002 (FIG. 4). The IDI gene encodes a rate-limiting IPP-DMAPP isomerase enzyme. These IspS-IDI genes were introduced into *Synechococcus* and several transformant colonies were obtained. The same genes were also introduced to and expressed in an *E. coli* host strain, which resulted in isoprene production at a rate of approximately 50 μg $L^{-1}$ $h^{-1}$. IspS-IDI transformants of *Synechococcus* sp. PCC 7002 grown under 100% $CO_2$ produced isoprene at a promising rate of approximately 330 μg $gDW^{-1}$ $h^{-1}$, equivalent to about 330 μg $L^{-1}$ $h^{-1}$ (FIG. 7).

Example 5

Inactivation of Light-Harvesting Genes for Increased Volumetric Yields

Figure 16:
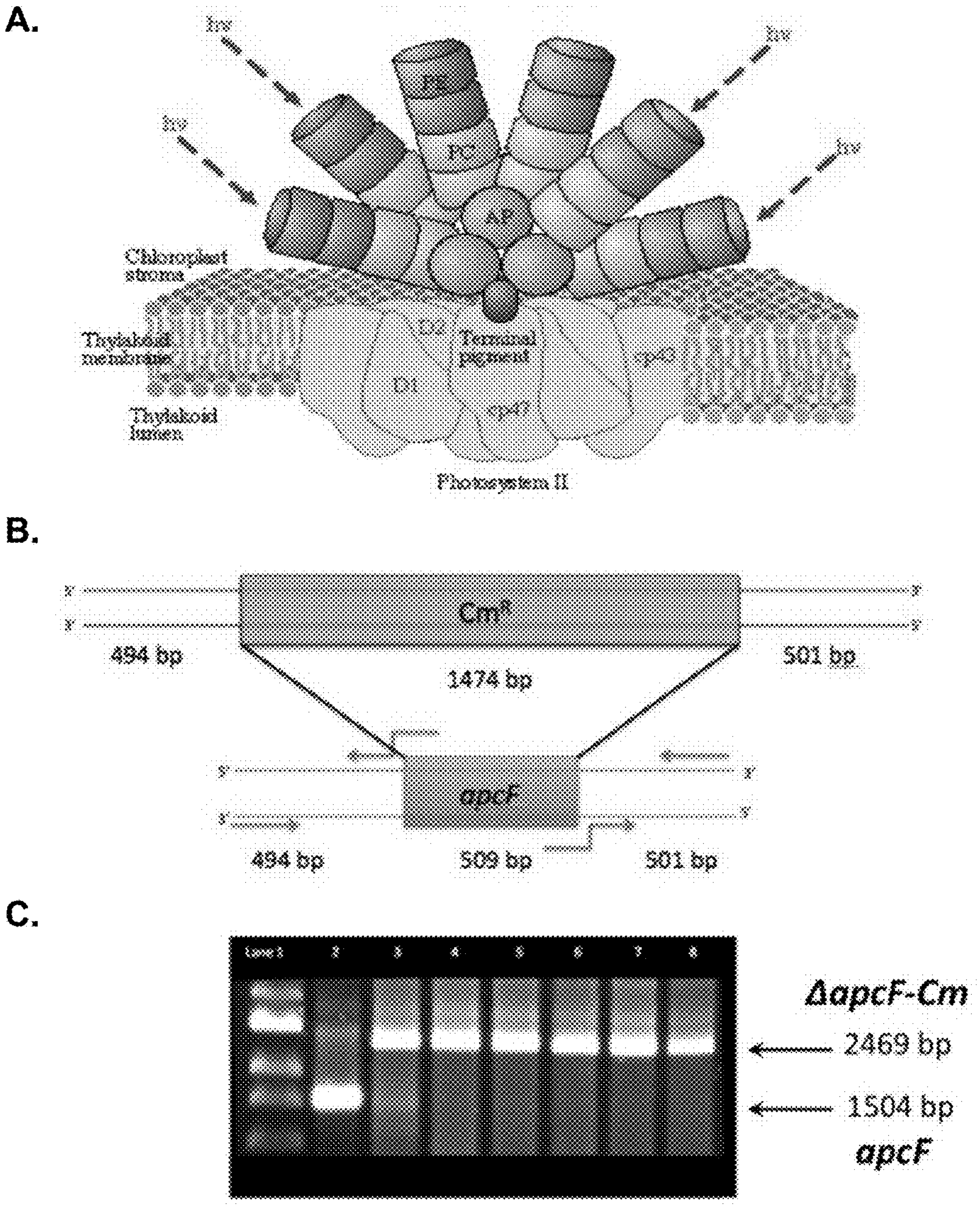
FIG. 16 illustrates (A) a cyanobacterial phycobilisome light-harvesting complex (see genome.jp/kegg/pathway on the World Wide Web) and (B) an example of targeted inactivation of a light-harvesting gene, the apcF gene (Locus Tag SynPCC7002_A1631) for allophycocyanin. The apcF gene encodes an allophycocyanin β-subunit of the phycobilisome light-harvesting complex. (C) Gel electrophoresis data demonstrate PCR amplification of DNA from primers flanking the apcF region. The PCR product is of the expected size for the inactivated apcF-Cm gene region with no remaining copies of the wild-type gene (lanes 3-8). Lane 2 shows a wild-type control.
Figure 17:
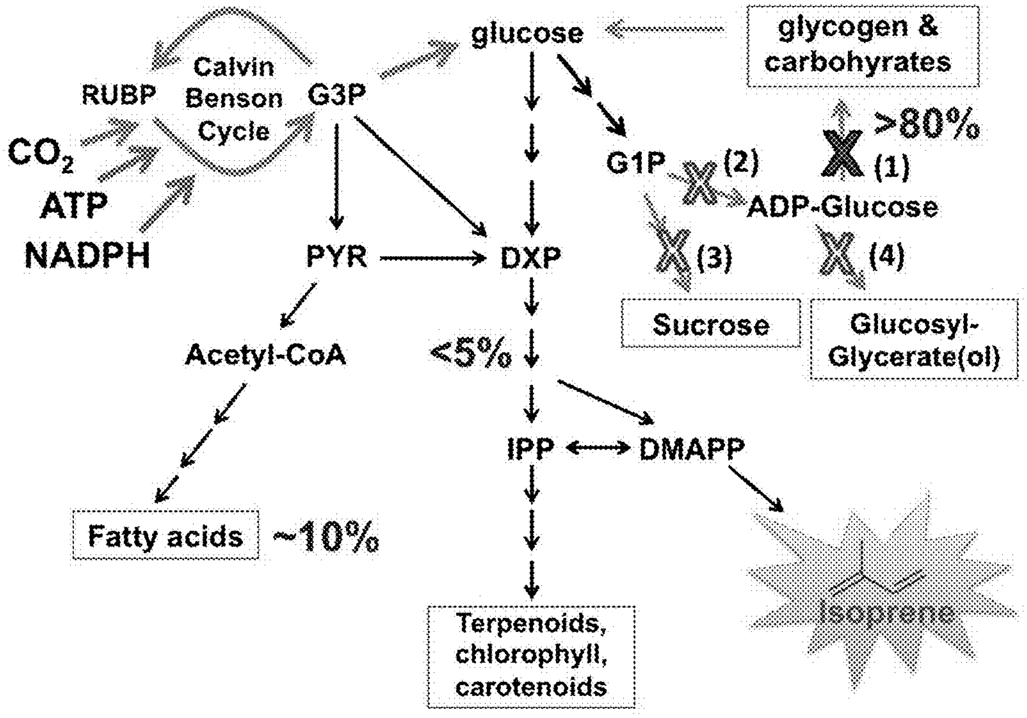
FIG. 17 illustrates major carbon flow pathways of *Synechococcus* sp. PCC 7002 cyanobacteria and targets for inactivation of competing glycogen synthesis and soluble sugar synthesis pathways. Genes for glycogen synthases (GlgA1, Locus Tag SynPCC7002_A1532 and GlgA2, Locus Tag SynPCC7002_A2125, at step (1)) have been inactivated. Gene/enzyme targets for inactivation of soluble sugar synthesis are ADP-Glucose pyrophosphorylase (GlgC, Locus Tag SynPCC7002_A0095, at step (2)), sucrose phosphate synthase (SpsA, Locus Tag SynPCC7002_A0888, at step (3)), and glucosylglycerol(ate) GGoI(GGate) synthases (GpgS, GpgP, GgpS, and GgpP, at step (4)). Locus Tags for the glucosylglycerol(ate) GGoI(GGate) synthases are SynPCC7002_A2021, _A2022, _A2851, and _A2841, respectively. GgpP is also designated StpA.

In cyanobacteria, phycobilisomes are the major light-harvesting complexes. As illustrated in FIG. 16, energy is funneled from phycoerythrin (PE) to phycocyanin (PC) to allophycocyanin (APC) to the photosynthetic reaction center protein complexes. *Synechococcus* sp. PCC 7002 does not express PE. ApcF encodes a p-subunit of APC (Locus Tag SynPCC7002_A1631) and is implicated in energy transfer to PS II (Dong et al., *BBA* 1787:1122 (2009)). A "mega-primer" PCR method (Frigaard et al., *Methods in Molecular Biology* 274:325 (2004)) was used to inactivate apcF by inserting a gene for chloramphenicol (Cm) antibiotic resistance into the apcF coding sequence (FIG. 16). As presented in FIG. 22, ApcF knockout mutations did not completely eliminate phycobilisomes, but the ΔApcF mutants grew very rapidly (having a doubling time of about 3.5 hours) at high (2000 μmol photons $m^{-2}$ $s^{-1}$) light intensity. These data demonstrate gene inactivation by "interposon" mutagenesis in cyanobacteria. Other light-harvesting genes to be targeted for inactivation include the allophycocyanin apcA (Locus Tag SynPCC7002_A1930) and phycocyanin cpcB (β-subunit of PC, Locus Tag SynPCC7002_A2209) genes. Mutations in these genes will eliminate expression of the entire allophycocyanin and phycocyanin operons, respectively and will, thus, eliminate the corresponding APC and PC light-harvesting complexes.

Example 6

Figure 18:
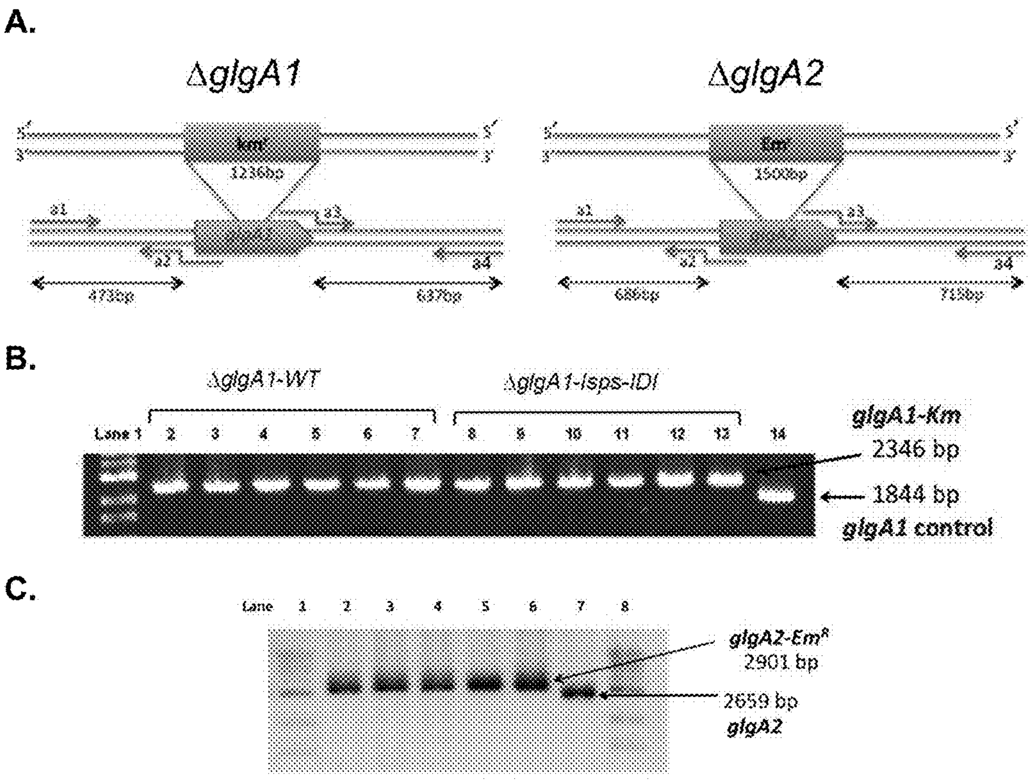
FIG. 18 presents the strategy used to inactivate glgA1 and glgA2 genes for glycogen synthesis (A), and data showing the inactivation of these genes (B and C). Gel electrophoresis data show PCR amplification of DNA from primers flanking the glgA1 and glgA2 regions. In both cases, the PCR products are the expected size for inactivated glgA1-Km and glgA2-Em regions, respectively, with no remaining copies of the wild-type genes. Lanes 14 and 17 in Panels A and B, respectively, show the wild-type controls.
Figure 19:
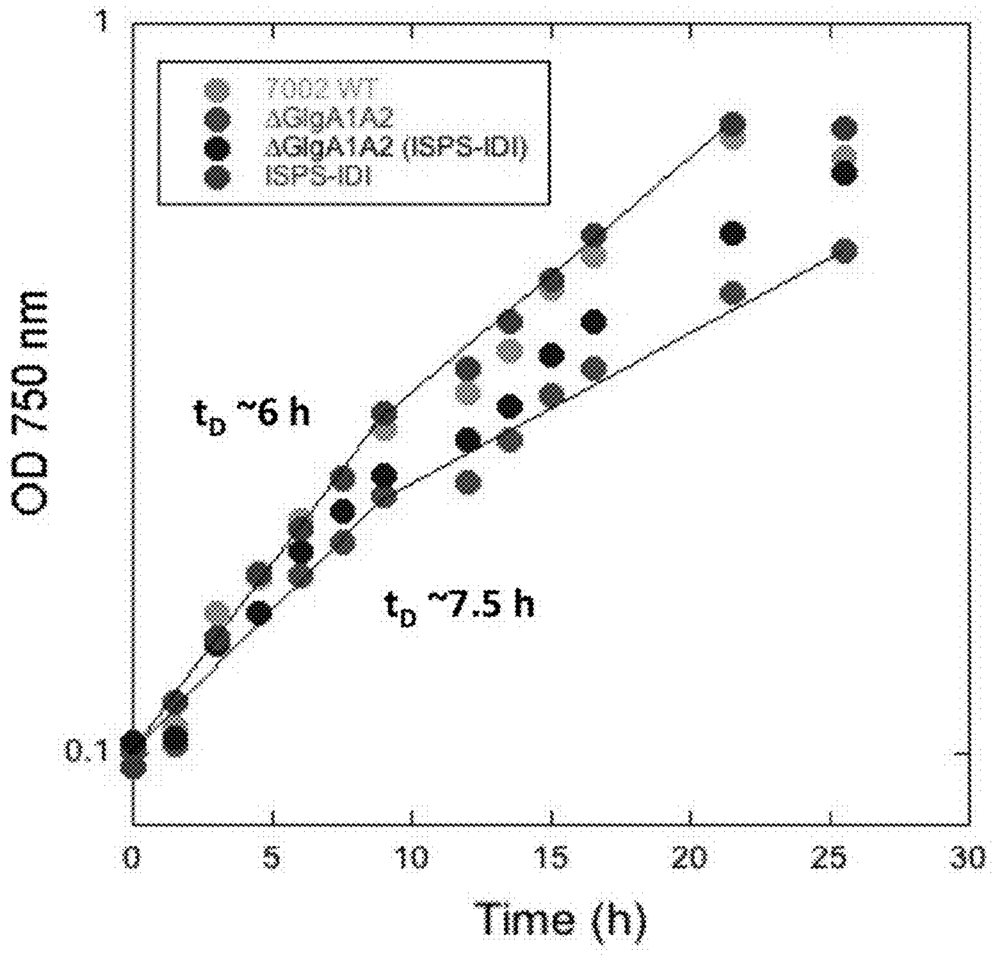
FIG. 19 presents growth data for *Synechococcus* sp. PCC 7002 (Isps-IDI) and ΔGlgA1A2 (IspS-IDI) strains under isoprene producing conditions. The IspS-IDI strain carries the optimized IspS and IDI genes illustrated in FIG. 4. The ΔGlgA1A2 (IspS-IDI) strain carries the same IspS and IDI genes together with inactivated glycogen synthase glgA1 and glgA2 genes. Cells were grown under 100% $CO_2$, 200 μmol photons $m^{-2}$ $s^{-1}$ light intensity, in sealed bottles to allow isoprene accumulation.
Figure 20:
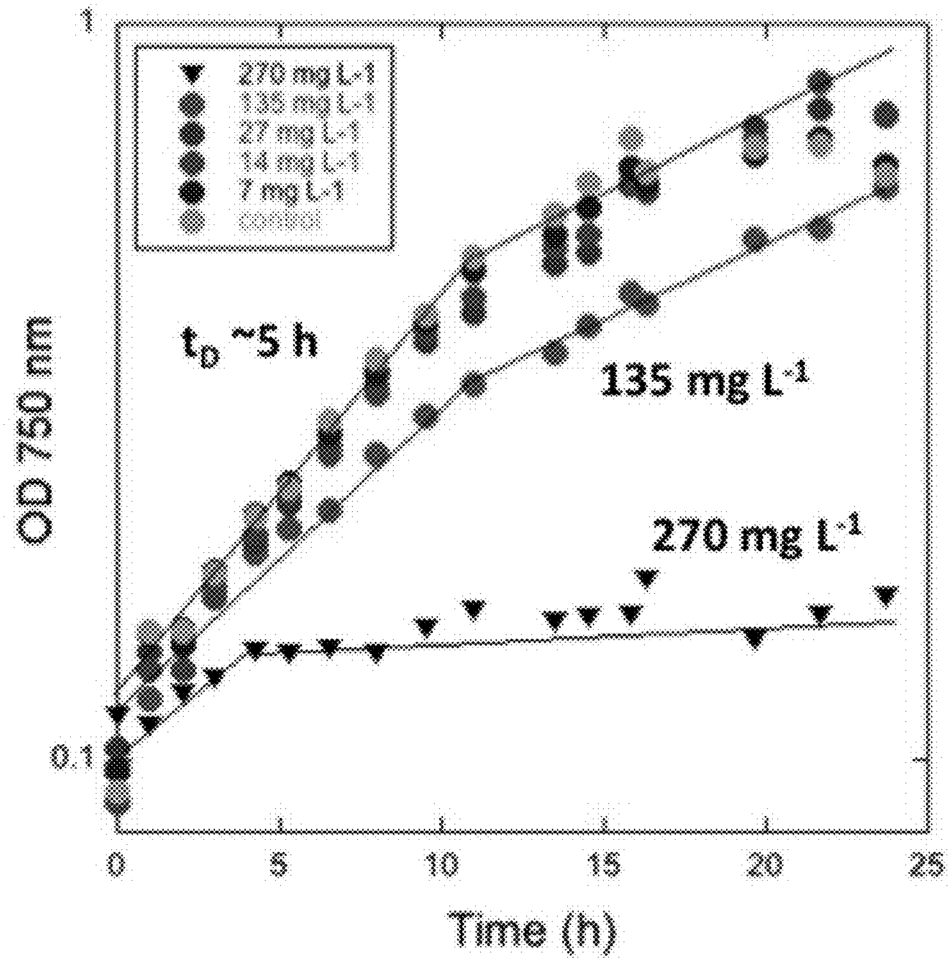
FIG. 20 presents growth data for wild-type *Synechococcus* sp. PCC 7002 in the presence of added, liquid isoprene. Growth conditions were otherwise as described in FIG. 19.

Inactivation of Glycogen Synthase Genes for Increased Carbon Flux to the MEP Pathway for Isoprenoid Synthesis In cyanobacteria, most of the carbon fixed by photosynthesis is stored as glycogen in reactions catalyzed by glycogen synthases GlgA1 and GlgA2 (Locus TagsSynPCC7002_A1532, _A2125). Only a small fraction of carbon typically flows into the MEP pathway. See Lindberg et al., *Metabolic Engineering* 12:70 (2010). The glgA1 and glgA2 genes (FIG. 18) in *Synechococcus* sp. PCC 7002 have been inactivated. It is expected that glgA1 and glgA2 inactivation, either alone or in combination with inactivated genes for soluble sugar synthesis such as glgC (for ADP-Glucose pyrophosphorylase, Locus Tag SynPCC7002_A0095), and/or spsA (for sucrose phosphate synthase, Locus Tag SynPCC7002_A0888), and/or combinations of gpgS, gpgP, ggpS, ggpP (for glucosylglycerate and glucosylglycerol synthesis, Locus Tag SynPCC7002_A2021, _A2022, _A2851, and _A2841), will significantly decrease carbon flux to glycogen and soluble sugars and substantially increase flux via the MEP pathway for isoprenoid production.

We claim:

1. A method for pinene production, the method comprising the steps of:
   (a) obtaining a host transgenic *Synechococcus* sp. PCC 7002 cyanobacterium comprising one or more transgenes encoding geranyl diphosphate synthase (GPPS), and mono-terpene synthase (mono-TPS); and
   (b) observing pinene production by the cyanobacterium, wherein pinene is produced at a rate of at least about 330 μg gDW$^{-1}$ h$^{-1}$.

2. The method of claim 1, wherein pinene is produced at a rate of at least about 660 μg gDW$^{-1}$ h$^{-1}$.

3. The method of claim 1, wherein pinene is produced at a rate of at least about 2000 μg gDW$^{-1}$ h$^{-1}$.

4. The method of claim 1, wherein pinene is produced at a rate of at least about 4000 μg gDW$^{-1}$ h$^{-1}$.

5. The method of claim 1, wherein the cyanobacterium further comprises a promoter derived from *Synechocystis* sp. PCC 6803.

6. The method of claim 5, wherein the promoter derived from *Synechocystis* sp. PCC 6803 is PcpcB.

7. The method of claim 5, wherein the promoter derived from *Synechocystis* sp. PCC 6803 is a synthetic PpsaA/B promoter.

8. The method of claim 1, wherein the one or more transgenes comprises codons preferred for expression in the cyanobacterium.

9. The method of claim 1, wherein the one or more transgenes encodes a protein identical to that isolated from an *Artemisia* species.

10. The method of claim 9, wherein the protein isolated from an *Artemisia* species is mono-TPS from *Artemisia annua*.

11. The method of claim 1, wherein the cyanobacterium of step (a) further comprises at least one transgene selected from the group consisting of a transgene encoding hydroxymethylbutenyl diphosphate reductase (HDR) and 1-deoxy-D-xylulose-5-phosphate synthase (DXS).

12. The method of claim 1, wherein pinene is produced under high $CO_2$ conditions.

13. The method of claim 12, wherein high $CO_2$ conditions comprise 100% $CO_2$ atmospheric conditions.

14. The method of claim 1, wherein pinene production comprises subjecting the cyanobacterium to a light-dark cycle, wherein a light portion of the light-dark cycle comprises full intensity sunlight.

15. The method of claim 1, further comprising recovering pinene produced by the cyanobacterium.

* * * * *

UNITED STATES PATENT AND TRADEMARK OFFICE

CERTIFICATE OF CORRECTION

PATENT NO. : 9,580,728 B2
APPLICATION NO. : 15/156557
DATED : February 28, 2017
INVENTOR(S) : Toivo Kallas, Matthew Nelson and Eric Singsaas It is certified that error appears in the above-identified patent and that said Letters Patent is hereby corrected as shown below:

In the Specification

Column 2, Line 26: $gDW^{-1}$ should be $gDW^{-1}$ $h^{-1}$

Column 3, Line 6: p-subunit should be β-subunit

Column 4, Line 65: 13-subunit should be β-subunit

Signed and Sealed this
Ninth Day of April, 2019

Andrei Iancu
*Director of the United States Patent and Trademark Office*

SEQUENCE LISTING

```
<160> NUMBER OF SEQ ID NOS: 23

<210> SEQ ID NO 1
<211> LENGTH: 601
<212> TYPE: DNA
<213> ORGANISM: Synechocystis PCC6803

<400> SEQUENCE: 1

gaattcgtta taaaataaac ttaacaaatc tatacccacc tgtagagaag agtccctgaa     60

tatcaaaatg gtgggataaa aagctcaaaa aggaaagtag gctgtggttc cctaggcaac    120

agtcttccct accccactgg aaactaaaaa aacgagaaaa gttcgcaccg aacatcaatt    180

gcataatttt agccctaaaa cataagctga acgaaactgg ttgtcttccc ttcccaatcc    240

aggacaatct gagaatcccc tgcaacatta cttaacaaaa aagcaggaat aaaattaaca    300

agatgtaaca gacataagtc ccatcaccgt tgtataaagt taactgtggg attgcaaaag    360

cattcaagcc taggcgctga gctgtttgag catcccggtg gcccttgtcg ctgcctccgt    420

gtttctccct ggatttattt aggtaatatc tctcataaat ccccgggtag ttaacgaaag    480

ttaatggaga tcagtaacaa taactctagg gtcattactt tggactccct cagtttatcc    540

gggggaattg tgtttaagaa aatcccaact cataaagtca agtaggagat taattcatat    600

g                                                                    601


<210> SEQ ID NO 2
<211> LENGTH: 134
<212> TYPE: DNA
<213> ORGANISM: Synechocystis PCC6803

<400> SEQUENCE: 2

gaattcagga gctagaactg gtcagggctg gggcaatttt taattattgt tacgcaggtc     60
```

-continued

```
ttgcctaggg gggggaggc cgtattatct tctagtgatg tttgctgaaa acgcctgaag    120

gagaataaca tatg                                                      134
```

<210> SEQ ID NO 3
<211> LENGTH: 1152
<212> TYPE: DNA
<213> ORGANISM: Abies grandis

<400> SEQUENCE: 3

```
atggcttatt catgtatggc cgcaagttgt cacggacttc attttatgaa tattgctagt     60

caagaatgca acctgaaacg cgggatcatt cccagcaaac gcttgcacgg tatcagctcc    120

tctctgtggg cgagcaacgg ctttcaaggc catctcgaac gggatctgag tgcctaccgt    180

cacttagtga gtagctcccg ttgcttgaat acgattgcca tgttaagcaa tctgtccgaa    240

caggccaaag aaaaagctac ggagttcgat tttaaggaat acctccattc caaagcgatc    300

tctgtgaacg aagccttgga acgtgctgtg cccttgcgct acccggaaaa gatccacgaa    360

gctatgcgtt attctttact ggcgggtggg aaacgcatcc ggcctattct caccattgcg    420

gcctgtgaac tcgtgggtgg gagcgaagag ctggctatgc cgaccgcctg cgcgatggaa    480

atgattcata ccatgtcctt aattcatgac gatttgccca gcatggacaa tgatgacctc    540

cgtcgcggca agctcaccaa tcataaggtt tttggtgaag gcacggcggt gctcgccggg    600

gatgccctct tgtctttcgc ttttgaacac attgcggtca gtacgcgcaa gaccgtcgct    660

tctcatcggg tgctgcgtgt tgtgagcgag ttaggcaagg ccattggttc ccaaggggtg    720

gccggcggtc aggtggcgga tattacctcc gagggtgacc ccagtgtcgg tttagagacg    780

ctggaatgga ttcacattca caagaccgcg gtcctcctgg aatgtgcggt ggtttccggt    840

gccattatcg gtggggcgag tgaaaatgaa atcgaacgga ccggccggta cgcgcgttgt    900

gttggcctct tgtttcaagt cgtcgatgac atcctcgacg ttacccgcag ctccgaagag    960

ctgggtaaaa cggccggcaa agatttagtg agtgataaag ctacgtatcc caaattgatg   1020

ggcttagaaa aagccaaaga atttgccgat gagctgctcg atcgcgccaa agaggaattg   1080

tcctgtttca atcccgcaaa agctgcgcct ctcctcgggt tggccgatta tatcgctttg   1140

cggcagaact ag                                                       1152
```

<210> SEQ ID NO 4
<211> LENGTH: 383
<212> TYPE: PRT
<213> ORGANISM: Abies grandis

<400> SEQUENCE: 4

```
Met Ala Tyr Ser Cys Met Ala Ala Ser Cys His Gly Leu His Phe Met
1               5                   10                  15

Asn Ile Ala Ser Gln Glu Cys Asn Leu Lys Arg Gly Ile Ile Pro Ser
            20                  25                  30

Lys Arg Leu His Gly Ile Ser Ser Ser Leu Trp Ala Ser Asn Gly Phe
        35                  40                  45

Gln Gly His Leu Glu Arg Asp Leu Ser Ala Tyr Arg His Leu Val Ser
    50                  55                  60

Ser Ser Arg Cys Leu Asn Thr Ile Ala Met Leu Ser Asn Leu Ser Glu
65                  70                  75                  80

Gln Ala Lys Glu Lys Ala Thr Glu Phe Asp Phe Lys Glu Tyr Leu His
                85                  90                  95
```

-continued

```
Ser Lys Ala Ile Ser Val Asn Glu Ala Leu Glu Arg Ala Val Pro Leu
            100                 105                 110

Arg Tyr Pro Glu Lys Ile His Glu Ala Met Arg Tyr Ser Leu Leu Ala
        115                 120                 125

Gly Gly Lys Arg Ile Arg Pro Ile Leu Thr Ile Ala Ala Cys Glu Leu
    130                 135                 140

Val Gly Gly Ser Glu Glu Leu Ala Met Pro Thr Ala Cys Ala Met Glu
145                 150                 155                 160

Met Ile His Thr Met Ser Leu Ile His Asp Asp Leu Pro Ser Met Asp
                165                 170                 175

Asn Asp Asp Leu Arg Arg Gly Lys Leu Thr Asn His Lys Val Phe Gly
            180                 185                 190

Glu Gly Thr Ala Val Leu Ala Gly Asp Ala Leu Leu Ser Phe Ala Phe
        195                 200                 205

Glu His Ile Ala Val Ser Thr Arg Lys Thr Val Ala Ser His Arg Val
    210                 215                 220

Leu Arg Val Val Ser Glu Leu Gly Lys Ala Ile Gly Ser Gln Gly Val
225                 230                 235                 240

Ala Gly Gly Gln Val Ala Asp Ile Thr Ser Glu Gly Asp Pro Ser Val
                245                 250                 255

Gly Leu Glu Thr Leu Glu Trp Ile His Ile His Lys Thr Ala Val Leu
            260                 265                 270

Leu Glu Cys Ala Val Val Ser Gly Ala Ile Ile Gly Gly Ala Ser Glu
        275                 280                 285

Asn Glu Ile Glu Arg Thr Gly Arg Tyr Ala Arg Cys Val Gly Leu Leu
    290                 295                 300

Phe Gln Val Val Asp Asp Ile Leu Asp Val Thr Arg Ser Ser Glu Glu
305                 310                 315                 320

Leu Gly Lys Thr Ala Gly Lys Asp Leu Val Ser Asp Lys Ala Thr Tyr
                325                 330                 335

Pro Lys Leu Met Gly Leu Glu Lys Ala Lys Glu Phe Ala Asp Glu Leu
            340                 345                 350

Leu Asp Arg Ala Lys Glu Glu Leu Ser Cys Phe Asn Pro Ala Lys Ala
        355                 360                 365

Ala Pro Leu Leu Gly Leu Ala Asp Tyr Ile Ala Leu Arg Gln Asn
    370                 375                 380


<210> SEQ ID NO 5
<211> LENGTH: 1680
<212> TYPE: DNA
<213> ORGANISM: Populus trichocarpa

<400> SEQUENCE: 5

atgtgtagtg ttagtaccga gaatgttagt tttaccgaga ccgaaaccga aacccgtcga     60

tccgcgaatt acgaacctaa tagttgggac tacgattatc tattaagctc cgatacagac    120

gaaagcattg aagtctataa agataaggca aaaaagctag aggcggaggt tcgtcgagaa    180

atcaataacg aaaaagctga atttttaacc ttactggagt tgattgataa cgttcagcgc    240

ctaggtttgg gttaccggtt tgagagtgat attcgccgtg cattagatcg gtttgtgtcc    300

tctggcggct ttgatgcggt gaccaagacc agtctccacg ccacagctct gtcctttcgc    360

ctgttgcgcc aacatggctt cgaggttagc caagaggctt ttggaggctt taaagaccag    420

aatggcaatt ttatggaaaa cctaaaagaa gacattaaag ccatcctctc tctctacgaa    480

gcttccttcc tcgcactcga aggtgaaaac attttagatg aagcgaaagt ctttgcgatt    540
```

-continued

```
agtcacctaa aggaactatc cgaagagaaa atcggtaaag atctcgccga acaggtgaat     600

cacgccctgg aactccccct acatcgtcgc acacagcgac tggaagccgt actaagtatt     660

gaagcttacc gcaagaaaga ggacgcagat caggtactgt tagaactcgc tattttagac     720

tacaatatga ttcaatccgt gtatcaacgg gatttacgcg aaacgtcccg gtggtggcgg     780

cgtgtggggt tggctaccaa actgcatttt gccagggatc gtttgattga aagtttttat     840

tgggccgttg gggtggcgtt tgaaccgcaa tatagcgact gtaggaatag tgtggctaag     900

atgtttagct ttgttacaat tatcgacgat atttatgacg tctatggaac cttggatgaa     960

ttggaattgt tcaccaacgc cgtggaacgg tgggacgtca atgcgattga cgatttaccc    1020

gattatatga aattgtgctt tttagcctta tataacacca ttaacgagat tgcctatgat    1080

aacttaaaag aaaaagggga aaacatccta ccctacttga ccaaagcctg ggctgatttg    1140

tgcaacgctt tcctgcaaga ggccaaatgg ttgtacaata aatccacgcc tacgtttgat    1200

gactattttg ggaatgcctg gaaatcctcc tctggaccct tgcaactggt tttcgcctat    1260

ttcgccgtcg tgcaaaatat taagaaagaa gaaatcgaga atttgaaaaa gtatcacgat    1320

atcatcagca ggccgagtca catttttcgg ttatgtaatg atttggccag cgcaagcgcc    1380

gaaattgccc ggggtgagac tgccaatagt gttagttgct acatgcggac taaagggatt    1440

agtgaggaac tggcgaccga aagtgtaatg aacttaattg acgagacgtg gaaaaagatg    1500

aataaggaga aattaggagg ttccttgttt gccaaaccct ttgtggaaac cgctatcaat    1560

ctcgcccgcc aatctcattg tacttatcat aatggcgatg cccatacttc tccagatgaa    1620

ctgacccgta aacgagtatt gagtgtgatc actgaaccaa ttctcccctt tgaacgctaa    1680
```

```
<210> SEQ ID NO 6
<211> LENGTH: 559
<212> TYPE: PRT
<213> ORGANISM: Populus trichocarpa

<400> SEQUENCE: 6

Met Cys Ser Val Ser Thr Glu Asn Val Ser Phe Thr Glu Thr Glu Thr
1               5                   10                  15

Glu Thr Arg Arg Ser Ala Asn Tyr Glu Pro Asn Ser Trp Asp Tyr Asp
            20                  25                  30

Tyr Leu Leu Ser Ser Asp Thr Asp Glu Ser Ile Glu Val Tyr Lys Asp
        35                  40                  45

Lys Ala Lys Lys Leu Glu Ala Glu Val Arg Arg Glu Ile Asn Asn Glu
    50                  55                  60

Lys Ala Glu Phe Leu Thr Leu Leu Glu Leu Ile Asp Asn Val Gln Arg
65                  70                  75                  80

Leu Gly Leu Gly Tyr Arg Phe Glu Ser Asp Ile Arg Arg Ala Leu Asp
                85                  90                  95

Arg Phe Val Ser Ser Gly Gly Phe Asp Ala Val Thr Lys Thr Ser Leu
            100                 105                 110

His Ala Thr Ala Leu Ser Phe Arg Leu Leu Arg Gln His Gly Phe Glu
        115                 120                 125

Val Ser Gln Glu Ala Phe Gly Gly Phe Lys Asp Gln Asn Gly Asn Phe
    130                 135                 140

Met Glu Asn Leu Lys Glu Asp Ile Lys Ala Ile Leu Ser Leu Tyr Glu
145                 150                 155                 160

Ala Ser Phe Leu Ala Leu Glu Gly Glu Asn Ile Leu Asp Glu Ala Lys
                165                 170                 175
```

```
Val Phe Ala Ile Ser His Leu Lys Glu Leu Ser Glu Glu Lys Ile Gly
            180                 185                 190

Lys Asp Leu Ala Glu Gln Val Asn His Ala Leu Glu Leu Pro Leu His
        195                 200                 205

Arg Arg Thr Gln Arg Leu Glu Ala Val Leu Ser Ile Glu Ala Tyr Arg
    210                 215                 220

Lys Lys Glu Asp Ala Asp Gln Val Leu Leu Glu Leu Ala Ile Leu Asp
225                 230                 235                 240

Tyr Asn Met Ile Gln Ser Val Tyr Gln Arg Asp Leu Arg Glu Thr Ser
                245                 250                 255

Arg Trp Trp Arg Arg Val Gly Leu Ala Thr Lys Leu His Phe Ala Arg
            260                 265                 270

Asp Arg Leu Ile Glu Ser Phe Tyr Trp Ala Val Gly Val Ala Phe Glu
        275                 280                 285

Pro Gln Tyr Ser Asp Cys Arg Asn Ser Val Ala Lys Met Phe Ser Phe
    290                 295                 300

Val Thr Ile Ile Asp Asp Ile Tyr Asp Val Tyr Gly Thr Leu Asp Glu
305                 310                 315                 320

Leu Glu Leu Phe Thr Asn Ala Val Glu Arg Trp Asp Val Asn Ala Ile
                325                 330                 335

Asp Asp Leu Pro Asp Tyr Met Lys Leu Cys Phe Leu Ala Leu Tyr Asn
            340                 345                 350

Thr Ile Asn Glu Ile Ala Tyr Asp Asn Leu Lys Glu Lys Gly Glu Asn
        355                 360                 365

Ile Leu Pro Tyr Leu Thr Lys Ala Trp Ala Asp Leu Cys Asn Ala Phe
    370                 375                 380

Leu Gln Glu Ala Lys Trp Leu Tyr Asn Lys Ser Thr Pro Thr Phe Asp
385                 390                 395                 400

Asp Tyr Phe Gly Asn Ala Trp Lys Ser Ser Ser Gly Pro Leu Gln Leu
                405                 410                 415

Val Phe Ala Tyr Phe Ala Val Val Gln Asn Ile Lys Lys Glu Glu Ile
            420                 425                 430

Glu Asn Leu Lys Lys Tyr His Asp Ile Ile Ser Arg Pro Ser His Ile
        435                 440                 445

Phe Arg Leu Cys Asn Asp Leu Ala Ser Ala Ser Ala Glu Ile Ala Arg
    450                 455                 460

Gly Glu Thr Ala Asn Ser Val Ser Cys Tyr Met Arg Thr Lys Gly Ile
465                 470                 475                 480

Ser Glu Glu Leu Ala Thr Glu Ser Val Met Asn Leu Ile Asp Glu Thr
                485                 490                 495

Trp Lys Lys Met Asn Lys Glu Lys Leu Gly Gly Ser Leu Phe Ala Lys
            500                 505                 510

Pro Phe Val Glu Thr Ala Ile Asn Leu Ala Arg Gln Ser His Cys Thr
        515                 520                 525

Tyr His Asn Gly Asp Ala His Thr Ser Pro Asp Glu Leu Thr Arg Lys
    530                 535                 540

Arg Val Leu Ser Val Ile Thr Glu Pro Ile Leu Pro Phe Glu Arg
545                 550                 555
```

```
<210> SEQ ID NO 7
<211> LENGTH: 693
<212> TYPE: DNA
<213> ORGANISM: Populus trichocarpa
```

-continued

<400> SEQUENCE: 7

```
atggctgctg gtatggatgc tgttcaacgt cgtttaatgt ttgaagatga gtgcattctc      60

gtggatgaaa atgaccgggt ggtcggccat gattctaaat acaactgcca tttatgggaa     120

aatattctaa aaggcaacgc cttgcatcgc gcgttttccg tgttcttgtt taatagcaaa     180

cacgagttac tgttacaaca aaggagtgcc actaaagtta cgtttcccct cgtttggacc     240

aatacctgtt gtagtcatcc tctgtatcgc gaaagcgaac taattcatga agacgctcta     300

ggcgttcgca acgcggccca aaggaagtta ttcgatgaac taggaatccc tgccgaagac     360

gtgcccgtgg accagttttc taccttaggg cgtattctgt ataaggcccc gtccgatggg     420

aaatggggtg agcacgaact ggactatttg ctgtttatcg tccgagatgt ttccgtcaac     480

cccaatccag acgaagtagc tgatatcaaa tacgtgaatc aagatgaatt gaaggaattg     540

ttgcggaaag ctgatgcagg agaagagggt ttgaaattaa gtccctggtt ccggctggta     600

gtggataatt ttttatttaa atggtgggat cacgtggaaa aggggacttt agaggaagct     660

gccgatatga aagccattca taaactcaca taa                                  693
```

<210> SEQ ID NO 8
<211> LENGTH: 230
<212> TYPE: PRT
<213> ORGANISM: Populus trichocarpa

<400> SEQUENCE: 8

```
Met Ala Ala Gly Met Asp Ala Val Gln Arg Arg Leu Met Phe Glu Asp
1               5                   10                  15

Glu Cys Ile Leu Val Asp Glu Asn Asp Arg Val Val Gly His Asp Ser
            20                  25                  30

Lys Tyr Asn Cys His Leu Trp Glu Asn Ile Leu Lys Gly Asn Ala Leu
        35                  40                  45

His Arg Ala Phe Ser Val Phe Leu Phe Asn Ser Lys His Glu Leu Leu
    50                  55                  60

Leu Gln Gln Arg Ser Ala Thr Lys Val Thr Phe Pro Leu Val Trp Thr
65                  70                  75                  80

Asn Thr Cys Cys Ser His Pro Leu Tyr Arg Glu Ser Glu Leu Ile His
                85                  90                  95

Glu Asp Ala Leu Gly Val Arg Asn Ala Ala Gln Arg Lys Leu Phe Asp
            100                 105                 110

Glu Leu Gly Ile Pro Ala Glu Asp Val Pro Val Asp Gln Phe Ser Thr
        115                 120                 125

Leu Gly Arg Ile Leu Tyr Lys Ala Pro Ser Asp Gly Lys Trp Gly Glu
    130                 135                 140

His Glu Leu Asp Tyr Leu Leu Phe Ile Val Arg Asp Val Ser Val Asn
145                 150                 155                 160

Pro Asn Pro Asp Glu Val Ala Asp Ile Lys Tyr Val Asn Gln Asp Glu
                165                 170                 175

Leu Lys Glu Leu Leu Arg Lys Ala Asp Ala Gly Glu Glu Gly Leu Lys
            180                 185                 190

Leu Ser Pro Trp Phe Arg Leu Val Val Asp Asn Phe Leu Phe Lys Trp
        195                 200                 205

Trp Asp His Val Glu Lys Gly Thr Leu Glu Glu Ala Ala Asp Met Lys
    210                 215                 220

Ala Ile His Lys Leu Thr
225                 230
```

-continued

<210> SEQ ID NO 9
<211> LENGTH: 1902
<212> TYPE: DNA
<213> ORGANISM: Bacillus amyloliquefaciens FZB42

<400> SEQUENCE: 9

```
atggacctgt taagtattca agatccgagt tttttaaaga agatgtccat tgagcaactc     60
gaggaactct ctgaagaaat tcgcaatttt ctcatcacca gtctcagcgc gtcgggagga    120
catattgggc cgaatctggg cgtggtcgaa ttaacaattg ccttgcacaa agaatttgac    180
agccccaaag acaaatttct gtgggacgtc ggccaccagt cgtatgtcca caaattgctt    240
accggccgtg ggaaagaatt tgaaactctg cgccaataca aagggttgtg cgggttccct    300
aaacgtagcg aaagtgaaca tgatgtgtgg gaaacgggcc atagttccac aagtttatcc    360
ggggcgatgg gtatggctgc cgcccgagac attaaaggct cgaaagaata catcatcccc    420
attattggtg acggtgcgtt aaccggcggc atggccttag aggcgctcaa ccacattggc    480
gacgagaaga aagatatgat cgtgatcctg aatgataatg aaatgtccat cgcgcccaat    540
gtcggagcta ttcactccat gctggggcgc cttcggacag cgggcaaata tcaatgggtg    600
aaagatgaac tggaatactt gtttaaacgc atcccggctg ttgggggcaa attggcggcg    660
accgctgagc gtattaaaga tagtctgaag tacatgctcg tgtctggaat gtttttcgaa    720
gaactcggct ttacctacct gggcccggtt gatggccact cttatcacga attgtttgaa    780
aacctgcagt atgcaaagaa aactaagggg cccgtgctct tgcacgtcat taccaagaag    840
ggaaagggct ataaacccgc cgaaactgat acaattggga cctggcatgg caccggcccc    900
tataagatta ataccgggga ttttgtaaaa cctaaagcag cagcccccag ctggagcggg    960
ctcgtttctg gcacggttca agaattagcc cgcgaggatg accgtattgt cgctatcact   1020
cctgcgatgc ctgtgggctc caaattggag ggggtttgcca aagagtttcc ggaacgtatg   1080
tttgatgtcg gtatcgccga acaacatgcg gccacgatgg ccgccggtat ggcgttgcaa   1140
ggtatgaaac cttttttagc catctacagc acctttctcc agcgcgccta tgatcaggtg   1200
gtgcacgaca tttgtcggca gaacgccaat gtatttatcg ggattgatcg cgcaggcctc   1260
gttggtgctg atggagaaac ccatcaaggg gtatttgata ttgctttctt acgccatatc   1320
cccaatttgg tcctgatgat gccgaaggat gagaacgaag gtcggcacat ggttaatact   1380
gcactcaact acgaagaagg tcccatcgcc atgcgctttc cacgcggtaa cggtttgggt   1440
gtcaaaatgg ataaagaact caagacgatt ccaattggca cgtgggaagt gttacgtcca   1500
ggcaaagatg ccgtgatttt aacgttcggt acgaccattg aaatggctct cgaagcggcc   1560
gaagaattac aaaaagaagg tttgagtgtt cgggtagtta acgcgcggtt catcaaaccc   1620
atcgataagc agatgatgaa agccattctt aatgagggtt tacccatcct cacgatcgaa   1680
gaagcggtgc tggagggtgg tttcggttct accatcctcg aatatgcaca tgatctcggc   1740
atgtatcaca ccccaattga tcgaatgggg attccggatc ggtttattga acatggttcg   1800
gtgacagccc tccttgagga aatcgggctt accaaggctg aagtgatgaa tcggattaaa   1860
cttcttatgc cccccaagac ccataaagga attggttctt aa                       1902
```

<210> SEQ ID NO 10
<211> LENGTH: 633
<212> TYPE: PRT
<213> ORGANISM: Bacillus amyloliquefaciens FZB42

<400> SEQUENCE: 10

-continued

Met Asp Leu Leu Ser Ile Gln Asp Pro Ser Phe Leu Lys Lys Met Ser
1 5 10 15

Ile Glu Gln Leu Glu Glu Leu Ser Glu Glu Ile Arg Asn Phe Leu Ile
20 25 30

Thr Ser Leu Ser Ala Ser Gly Gly His Ile Gly Pro Asn Leu Gly Val
35 40 45

Val Glu Leu Thr Ile Ala Leu His Lys Glu Phe Asp Ser Pro Lys Asp
50 55 60

Lys Phe Leu Trp Asp Val Gly His Gln Ser Tyr Val His Lys Leu Leu
65 70 75 80

Thr Gly Arg Gly Lys Glu Phe Glu Thr Leu Arg Gln Tyr Lys Gly Leu
85 90 95

Cys Gly Phe Pro Lys Arg Ser Glu Ser Glu His Asp Val Trp Glu Thr
100 105 110

Gly His Ser Ser Thr Ser Leu Ser Gly Ala Met Gly Met Ala Ala Ala
115 120 125

Arg Asp Ile Lys Gly Ser Lys Glu Tyr Ile Ile Pro Ile Ile Gly Asp
130 135 140

Gly Ala Leu Thr Gly Gly Met Ala Leu Glu Ala Leu Asn His Ile Gly
145 150 155 160

Asp Glu Lys Lys Asp Met Ile Val Ile Leu Asn Asp Asn Glu Met Ser
165 170 175

Ile Ala Pro Asn Val Gly Ala Ile His Ser Met Leu Gly Arg Leu Arg
180 185 190

Thr Ala Gly Lys Tyr Gln Trp Val Lys Asp Glu Leu Glu Tyr Leu Phe
195 200 205

Lys Arg Ile Pro Ala Val Gly Gly Lys Leu Ala Ala Thr Ala Glu Arg
210 215 220

Ile Lys Asp Ser Leu Lys Tyr Met Leu Val Ser Gly Met Phe Phe Glu
225 230 235 240

Glu Leu Gly Phe Thr Tyr Leu Gly Pro Val Asp Gly His Ser Tyr His
245 250 255

Glu Leu Phe Glu Asn Leu Gln Tyr Ala Lys Lys Thr Lys Gly Pro Val
260 265 270

Leu Leu His Val Ile Thr Lys Lys Gly Lys Gly Tyr Lys Pro Ala Glu
275 280 285

Thr Asp Thr Ile Gly Thr Trp His Gly Thr Gly Pro Tyr Lys Ile Asn
290 295 300

Thr Gly Asp Phe Val Lys Pro Lys Ala Ala Ala Pro Ser Trp Ser Gly
305 310 315 320

Leu Val Ser Gly Thr Val Gln Glu Leu Ala Arg Glu Asp Asp Arg Ile
325 330 335

Val Ala Ile Thr Pro Ala Met Pro Val Gly Ser Lys Leu Glu Gly Phe
340 345 350

Ala Lys Glu Phe Pro Glu Arg Met Phe Asp Val Gly Ile Ala Glu Gln
355 360 365

His Ala Ala Thr Met Ala Ala Gly Met Ala Leu Gln Gly Met Lys Pro
370 375 380

Phe Leu Ala Ile Tyr Ser Thr Phe Leu Gln Arg Ala Tyr Asp Gln Val
385 390 395 400

Val His Asp Ile Cys Arg Gln Asn Ala Asn Val Phe Ile Gly Ile Asp
405 410 415

-continued

```
Arg Ala Gly Leu Val Gly Ala Asp Gly Glu Thr His Gln Gly Val Phe
            420                 425                 430

Asp Ile Ala Phe Leu Arg His Ile Pro Asn Leu Val Leu Met Met Pro
        435                 440                 445

Lys Asp Glu Asn Glu Gly Arg His Met Val Asn Thr Ala Leu Asn Tyr
    450                 455                 460

Glu Glu Gly Pro Ile Ala Met Arg Phe Pro Arg Gly Asn Gly Leu Gly
465                 470                 475                 480

Val Lys Met Asp Lys Glu Leu Lys Thr Ile Pro Ile Gly Thr Trp Glu
                485                 490                 495

Val Leu Arg Pro Gly Lys Asp Ala Val Ile Leu Thr Phe Gly Thr Thr
            500                 505                 510

Ile Glu Met Ala Leu Glu Ala Ala Glu Glu Leu Gln Lys Glu Gly Leu
        515                 520                 525

Ser Val Arg Val Val Asn Ala Arg Phe Ile Lys Pro Ile Asp Lys Gln
    530                 535                 540

Met Met Lys Ala Ile Leu Asn Glu Gly Leu Pro Ile Leu Thr Ile Glu
545                 550                 555                 560

Glu Ala Val Leu Glu Gly Gly Phe Gly Ser Thr Ile Leu Glu Tyr Ala
                565                 570                 575

His Asp Leu Gly Met Tyr His Thr Pro Ile Asp Arg Met Gly Ile Pro
            580                 585                 590

Asp Arg Phe Ile Glu His Gly Ser Val Thr Ala Leu Leu Glu Glu Ile
        595                 600                 605

Gly Leu Thr Lys Ala Glu Val Met Asn Arg Ile Lys Leu Leu Met Pro
    610                 615                 620

Pro Lys Thr His Lys Gly Ile Gly Ser
625                 630
```

<210> SEQ ID NO 11
<211> LENGTH: 945
<212> TYPE: DNA
<213> ORGANISM: Bacillus amyloliquefaciens

<400> SEQUENCE: 11

```
atggatgtta ttaagattag ccctcgcggt tattgttacg gtgtggtcga tgcgatggtt     60

attgccaaaa acgcgtctct ggacaaaacc ttgccccgcc cgatttatat tctgggcatg    120

atcgtgcaca acaagcacgt tacagatgcc ttcgaggaag atgggattta tactcttgat    180

ggcaccaacc gactcgagat tctcaaacag gtggaaaagg ggaccgtaat ttttaccgct    240

cacggcgtaa gtcctgaagt gcgtaaagcg gccgaggaga aaggtttagt cactatcgat    300

gctacctgtc ccgatgtgac caagacgcat gatttgatcc ggaaagtcaa agccgaaggc    360

tatcacgtca tctatatcgg gaaaaagggt catccagaac cagaaggagc agttggtgtg    420

gcccccgaaa tcgtgcattt agtcgaaacc gaagaagatg tgcggaatct ggacatccaa    480

gccgaaaaac tgatcgtgac taatcaaacg accatgagtc agtgggatgt gcatgacatc    540

atggaatccg tcaaagaaaa atacccctat gtggaatacc accaagagat ttgcctcgcg    600

acccaagtcc ggcaagaagc tgtttctgaa caggcgaaga aagcagatct cacgattgtt    660

gttggtgacc ccaaatcgaa taacagcaat cgtctggctc aagtgtccga agaaattgcg    720

ggcaccaaag cctaccgcat tggcgacatc agtgaattga aattggaatg gcttaaggat    780

gtaaatacag tggcggtaac agcaggagcc tcgaccccga cgcccattac gaaggaagtc    840

attcgctttc tcgagcagtt tgatcacaat gacgaatcca cctggcagtt agagcatagc    900
```

gtccccctca agaagatttt gccgaaagtt aaaatcaaaa attaa 945

<210> SEQ ID NO 12
<211> LENGTH: 314
<212> TYPE: PRT
<213> ORGANISM: Bacillus amyloliquefaciens

<400> SEQUENCE: 12

```
Met Asp Val Ile Lys Ile Ser Pro Arg Gly Tyr Cys Tyr Gly Val Val
1               5                   10                  15

Asp Ala Met Val Ile Ala Lys Asn Ala Ser Leu Asp Lys Thr Leu Pro
            20                  25                  30

Arg Pro Ile Tyr Ile Leu Gly Met Ile Val His Asn Lys His Val Thr
        35                  40                  45

Asp Ala Phe Glu Glu Asp Gly Ile Tyr Thr Leu Asp Gly Thr Asn Arg
    50                  55                  60

Leu Glu Ile Leu Lys Gln Val Glu Lys Gly Thr Val Ile Phe Thr Ala
65                  70                  75                  80

His Gly Val Ser Pro Glu Val Arg Lys Ala Ala Glu Glu Lys Gly Leu
                85                  90                  95

Val Thr Ile Asp Ala Thr Cys Pro Asp Val Thr Lys Thr His Asp Leu
            100                 105                 110

Ile Arg Lys Val Lys Ala Glu Gly Tyr His Val Ile Tyr Ile Gly Lys
        115                 120                 125

Lys Gly His Pro Glu Pro Glu Gly Ala Val Gly Val Ala Pro Glu Ile
    130                 135                 140

Val His Leu Val Glu Thr Glu Glu Asp Val Arg Asn Leu Asp Ile Gln
145                 150                 155                 160

Ala Glu Lys Leu Ile Val Thr Asn Gln Thr Thr Met Ser Gln Trp Asp
                165                 170                 175

Val His Asp Ile Met Glu Ser Val Lys Glu Lys Tyr Pro Tyr Val Glu
            180                 185                 190

Tyr His Gln Glu Ile Cys Leu Ala Thr Gln Val Arg Gln Glu Ala Val
        195                 200                 205

Ser Glu Gln Ala Lys Lys Ala Asp Leu Thr Ile Val Val Gly Asp Pro
    210                 215                 220

Lys Ser Asn Asn Ser Asn Arg Leu Ala Gln Val Ser Glu Glu Ile Ala
225                 230                 235                 240

Gly Thr Lys Ala Tyr Arg Ile Gly Asp Ile Ser Glu Leu Lys Leu Glu
                245                 250                 255

Trp Leu Lys Asp Val Asn Thr Val Ala Val Thr Ala Gly Ala Ser Thr
            260                 265                 270

Pro Thr Pro Ile Thr Lys Glu Val Ile Arg Phe Leu Glu Gln Phe Asp
        275                 280                 285

His Asn Asp Glu Ser Thr Trp Gln Leu Glu His Ser Val Pro Leu Lys
    290                 295                 300

Lys Ile Leu Pro Lys Val Lys Ile Lys Asn
305                 310
```

<210> SEQ ID NO 13
<211> LENGTH: 477
<212> TYPE: DNA
<213> ORGANISM: Bacillus amyloliquefaciens FZB42

<400> SEQUENCE: 13

-continued

```
atgtttcgta tcggccaggg ttttgacgtt caccagttaa cggaaggtcg cccactcatt     60

attggtggca tcgaaattcc gtatgaaaaa gggttgctgg gccatagtga tgccgatgta    120

ctgttacaca cggtggccga tgcgtgctta ggcgctgcag gcgaaggaga catcggtaaa    180

cattttcctg acactgatcc cgagttcaag gatgccgact ccttcaagct ccttcagcac    240

gtgtggaaca tcgtcaaaga gaaaggatac gtcctcggga atattgattg taccatcatt    300

gcccagaaac ccaaaatggc cccccatatc gatgcgatgc ggaagcgaat tgccgaaggc    360

ctcgaagctg atgtgagcca agttaatgtg aaggctacca ccacggaaaa attggggttt    420

accgggcgtg cggaaggcat tgcagcccaa gccaccgtcc tcattcaaaa agcgtaa       477


<210> SEQ ID NO 14
<211> LENGTH: 158
<212> TYPE: PRT
<213> ORGANISM: Bacillus amyloliquefaciens FZB42

<400> SEQUENCE: 14

Met Phe Arg Ile Gly Gln Gly Phe Asp Val His Gln Leu Thr Glu Gly
1               5                   10                  15

Arg Pro Leu Ile Ile Gly Gly Ile Glu Ile Pro Tyr Glu Lys Gly Leu
            20                  25                  30

Leu Gly His Ser Asp Ala Asp Val Leu Leu His Thr Val Ala Asp Ala
        35                  40                  45

Cys Leu Gly Ala Ala Gly Glu Gly Asp Ile Gly Lys His Phe Pro Asp
    50                  55                  60

Thr Asp Pro Glu Phe Lys Asp Ala Asp Ser Phe Lys Leu Leu Gln His
65                  70                  75                  80

Val Trp Asn Ile Val Lys Glu Lys Gly Tyr Val Leu Gly Asn Ile Asp
                85                  90                  95

Cys Thr Ile Ile Ala Gln Lys Pro Lys Met Ala Pro His Ile Asp Ala
            100                 105                 110

Met Arg Lys Arg Ile Ala Glu Gly Leu Glu Ala Asp Val Ser Gln Val
        115                 120                 125

Asn Val Lys Ala Thr Thr Thr Glu Lys Leu Gly Phe Thr Gly Arg Ala
    130                 135                 140

Glu Gly Ile Ala Ala Gln Ala Thr Val Leu Ile Gln Lys Ala
145                 150                 155


<210> SEQ ID NO 15
<211> LENGTH: 1108
<212> TYPE: DNA
<213> ORGANISM: Artificial Sequence
<220> FEATURE:
<223> OTHER INFORMATION: NT sequence of bacteriophage lambda PR promoter
      with the thermolabile cI857 repressor and 22 AA lambda PR Cro

<400> SEQUENCE: 15

tgcaggtgat gattatcagc cagcagagaa ttaaggaaaa cagacaggtt tattgagcgc     60

ttatctttcc ctttattttt gctgcggtaa gtcgcataaa aaccattctt cataattcaa    120

tccatttact atgttatgtt ctgaggggag tgaaaattcc cctaattcga tgaagattct    180

tgctcaattg ttatcagcta tgcgccgacc agaacacctt gccgatcagc caaacgtctc    240

ttcaggccac tgactagcga taactttccc cacaacggaa caactctcat tgcatgggat    300

cattgggtac tgtgggttta gtggttgtaa aaacacctga ccgctatccc tgatcagttt    360

cttgaaggta aactcatcac ccccaagtct ggctatgcag aaatcacctg gctcaacagc    420
```

```
ctgctcaggg tcaacgagaa ttaacattcc gtcaggaaag cttggcttgg agcctgttgg    480

tgcggtcatg gaattacctt caacctcaag ccagaatgca gaatcactgg ctttttggt    540

tgtgcttacc catctctccg catcaccttt ggtaaaggtt ctaagctcag gtgagaacat    600

ccctgcctga acatgagaaa aaacagggta ctcatactca cttctaagtg acggctgcat    660

actaaccgct tcatacatct cgtagatttc tctggcgatt gaagggctaa attcttcaac    720

gctaactttg agaatttttg caagcaatgc ggcgttataa gcatttaatg cattgatgcc    780

attaaataaa gcaccaacgc ctgactgccc catccccatc ttgtctgcga cagattcctg    840

ggataagcca agttcatttt tcttttttc ataaattgct ttaaggcgac gtgcgtcctc    900

aagctgctct tgtgttaatg gtttcttttt tgtgctcata cgttaaatct atcaccgcaa    960

gggataaata tctaacaccg tgcgtgttga ctattttacc tctggcggtg ataatggttg   1020

catgtactaa ggaggttgta tggaacaacg cataaccctg aaagattatg caatgcgctt   1080

tgggcaaacc aagacagcta aagatccg                                      1108


<210> SEQ ID NO 16
<211> LENGTH: 237
<212> TYPE: PRT
<213> ORGANISM: Artificial Sequence
<220> FEATURE:
<223> OTHER INFORMATION: AA sequence of bacteriophage lambda PR promoter
      with the thermolabile cI857 repressor and 22 AA lambda PR Cro

<400> SEQUENCE: 16

Met Ser Thr Lys Lys Lys Pro Leu Thr Gln Glu Gln Leu Glu Asp Ala
1               5                   10                  15

Arg Arg Leu Lys Ala Ile Tyr Glu Lys Lys Lys Asn Glu Leu Gly Leu
            20                  25                  30

Ser Gln Glu Ser Val Ala Asp Lys Met Gly Met Gly Gln Ser Gly Val
        35                  40                  45

Gly Ala Leu Phe Asn Gly Ile Asn Ala Leu Asn Ala Tyr Asn Ala Ala
    50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235
```

<210> SEQ ID NO 17
<211> LENGTH: 1042
<212> TYPE: DNA
<213> ORGANISM: Artificial Sequence
<220> FEATURE:
<223> OTHER INFORMATION: NT sequence of bacteriophage lambda PR promoter with the thermolabile cI857 repressor

<400> SEQUENCE: 17

```
tgcaggtgat gattatcagc cagcagagaa ttaaggaaaa cagacaggtt tattgagcgc     60

ttatctttcc ctttattttt gctgcggtaa gtcgcataaa aaccattctt cataattcaa    120

tccatttact atgttatgtt ctgaggggag tgaaaattcc cctaattcga tgaagattct    180

tgctcaattg ttatcagcta tgcgccgacc agaacacctt gccgatcagc caaacgtctc    240

ttcaggccac tgactagcga taactttccc cacaacggaa caactctcat tgcatgggat    300

cattgggtac tgtgggttta gtggttgtaa aaacacctga ccgctatccc tgatcagttt    360

cttgaaggta aactcatcac ccccaagtct ggctatgcag aaatcacctg gctcaacagc    420

ctgctcaggg tcaacgagaa ttaacattcc gtcaggaaag cttggcttgg agcctgttgg    480

tgcggtcatg gaattacctt caacctcaag ccagaatgca gaatcactgg cttttttggt    540

tgtgcttacc catctctccg catcaccttt ggtaaaggtt ctaagctcag gtgagaacat    600

ccctgcctga acatgagaaa aaacagggta ctcatactca cttctaagtg acggctgcat    660

actaaccgct tcatacatct cgtagatttc tctggcgatt gaagggctaa attcttcaac    720

gctaactttg agaatttttg caagcaatgc ggcgttataa gcatttaatg cattgatgcc    780

attaaataaa gcaccaacgc ctgactgccc catccccatc ttgtctgcga cagattcctg    840

ggataagcca agttcatttt tctttttttc ataaattgct ttaaggcgac gtgcgtcctc    900

aagctgctct tgtgttaatg gtttcttttt tgtgctcata cgttaaatct atcaccgcaa    960

gggataaata tctaacaccg tgcgtgttga ctattttacc tctggcggtg ataatggttg   1020

catgtactaa ggaggttgta tg                                            1042
```

<210> SEQ ID NO 18
<211> LENGTH: 237
<212> TYPE: PRT
<213> ORGANISM: Artificial Sequence
<220> FEATURE:
<223> OTHER INFORMATION: AA sequence of bacteriophage lambda PR promoter with the thermolabile cI857 repressor

<400> SEQUENCE: 18

```
Met Ser Thr Lys Lys Lys Pro Leu Thr Gln Glu Gln Leu Glu Asp Ala
1               5                   10                  15

Arg Arg Leu Lys Ala Ile Tyr Glu Lys Lys Lys Asn Glu Leu Gly Leu
            20                  25                  30

Ser Gln Glu Ser Val Ala Asp Lys Met Gly Met Gly Gln Ser Gly Val
        35                  40                  45

Gly Ala Leu Phe Asn Gly Ile Asn Ala Leu Asn Ala Tyr Asn Ala Ala
    50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110
```

-continued

```
Gly Met Phe Ser Pro Glu Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235


<210> SEQ ID NO 19
<211> LENGTH: 1749
<212> TYPE: DNA
<213> ORGANISM: Artemisia annua

<400> SEQUENCE: 19

atggcttcaa tgtgcacctt ttcttctcct tttctcttat gcaacagcag tattagtcgt      60

accaatattg tggcttgcaa taaacagacg tctacgttgc aggcccaggt taaaaatgtg     120

gctacgattg aaacgaccaa ccgccgttct gccaattacg ccccgtccct ctggagctat     180

gattttgtcc agagtttaag cagcaaatac aaaggggaca attatatggc ccggtcccgc     240

gccttaaaag gggtcgttcg gacgatgatt ttagaggcca atgggattga gaaccccttg     300

tctctgctca acttagttga tgatctccaa cggttgggta tctcttatca cttcttggac     360

gaaatctcta acgtgttgga gaaaatttat ttaaattttt ataaatcccc cgaaaaatgg     420

acgaacatgg atctcaatct gcgctccctg ggctttcgcc tgttgcgcca acatggttat     480

cacattcccc aagagatttt taaagacttt atcgatgtga atggtaactt caagggtgac     540

atcatctcta tgctcaacct ctacgaagcc agttaccact ctgtcgaaga agaatccatc     600

ttagatgatg cgcgtgaatt taccaccaaa tatttgaaag aaaccttgga aaatattgaa     660

gatcagaata tcgcattgtt tattagtcac gcgcttgtgt ttcctttaca ttggatggtg     720

ccacgggtgg agacgagttg gtttattgaa gtgtacccca agaaagtggg catgaatccg     780

acggtcctcg agttcgcgaa gttggatttt aacattctcc aggcggttca ccaagaagat     840

atgaagaaag cctcccgttg gtggaaagaa acctgttggg aaaaatttgg cttcgcccgg     900

gaccggctcg tcgagaattt catgtggacc gttgccgaaa actacttgcc ccattttcag     960

accggccgcg gtgttctgac caaagtcaat gcgatgatca ccaccatcga tgatgtctac    1020

gacgtgtatg gcaccctccc tgagttagaa ttgtttacca acattgtcaa tagctgggac    1080

attaatgcca ttgatgagct gcccgattat ctcaaaattt gttttctggc gtgttacaac    1140

gctaccaatg aactgagtta taataccctg accaacaaag gtttttttgt tcatccctac    1200

ctcaagaaag cctggcaaga tctctgtaat agctacatca ttgaagcgaa gtggtttaat    1260

gacgggtaca ccccgacgtt caacgaattt attgagaatg cttatatgag cattggcatc    1320

gcgcctatca ttcgccatgc ctatctcttg accctcacga gcgtcacgga agaagccctg    1380
```

```
caacatatcg aacgtgcgga gtccatgatt cgtaatgctt gcttaattgt gcgtctcacc   1440

aatgatatgg gtacgagttc cgatgagctg gaacggggtg atattcccaa gagtattcaa   1500

tgctatatgc acgaaagtgg cgccaccgaa atggaagcgc gtgcctatat caagcaattc   1560

atcgttgaaa cgtggaagaa actgaataag gaacgccaag aaatcgggtc tgaatttccg   1620

caagaatttg tcgattgcgt tatcaactta ccccgcatgg gccactttat gtatacggat   1680

ggggacaaac atgggaagcc cgatatgttc aaaccttacg tctttagctt attcgtgaac   1740

cccatctaa                                                           1749


<210> SEQ ID NO 20
<211> LENGTH: 582
<212> TYPE: PRT
<213> ORGANISM: Artemisia annua

<400> SEQUENCE: 20

Met Ala Ser Met Cys Thr Phe Ser Ser Pro Phe Leu Leu Cys Asn Ser
1               5                   10                  15

Ser Ile Ser Arg Thr Asn Ile Val Ala Cys Asn Lys Gln Thr Ser Thr
            20                  25                  30

Leu Gln Ala Gln Val Lys Asn Val Ala Thr Ile Glu Thr Thr Asn Arg
        35                  40                  45

Arg Ser Ala Asn Tyr Ala Pro Ser Leu Trp Ser Tyr Asp Phe Val Gln
    50                  55                  60

Ser Leu Ser Ser Lys Tyr Lys Gly Asp Asn Tyr Met Ala Arg Ser Arg
65                  70                  75                  80

Ala Leu Lys Gly Val Val Arg Thr Met Ile Leu Glu Ala Asn Gly Ile
                85                  90                  95

Glu Asn Pro Leu Ser Leu Leu Asn Leu Val Asp Asp Leu Gln Arg Leu
            100                 105                 110

Gly Ile Ser Tyr His Phe Leu Asp Glu Ile Ser Asn Val Leu Glu Lys
        115                 120                 125

Ile Tyr Leu Asn Phe Tyr Lys Ser Pro Glu Lys Trp Thr Asn Met Asp
    130                 135                 140

Leu Asn Leu Arg Ser Leu Gly Phe Arg Leu Leu Arg Gln His Gly Tyr
145                 150                 155                 160

His Ile Pro Gln Glu Ile Phe Lys Asp Phe Ile Asp Val Asn Gly Asn
                165                 170                 175

Phe Lys Gly Asp Ile Ile Ser Met Leu Asn Leu Tyr Glu Ala Ser Tyr
            180                 185                 190

His Ser Val Glu Glu Glu Ser Ile Leu Asp Asp Ala Arg Glu Phe Thr
        195                 200                 205

Thr Lys Tyr Leu Lys Glu Thr Leu Glu Asn Ile Glu Asp Gln Asn Ile
    210                 215                 220

Ala Leu Phe Ile Ser His Ala Leu Val Phe Pro Leu His Trp Met Val
225                 230                 235                 240

Pro Arg Val Glu Thr Ser Trp Phe Ile Glu Val Tyr Pro Lys Lys Val
                245                 250                 255

Gly Met Asn Pro Thr Val Leu Glu Phe Ala Lys Leu Asp Phe Asn Ile
            260                 265                 270

Leu Gln Ala Val His Gln Glu Asp Met Lys Lys Ala Ser Arg Trp Trp
        275                 280                 285

Lys Glu Thr Cys Trp Glu Lys Phe Gly Phe Ala Arg Asp Arg Leu Val
    290                 295                 300
```

-continued

Glu Asn Phe Met Trp Thr Val Ala Glu Asn Tyr Leu Pro His Phe Gln
305 310 315 320

Thr Gly Arg Gly Val Leu Thr Lys Val Asn Ala Met Ile Thr Thr Ile
325 330 335

Asp Asp Val Tyr Asp Val Tyr Gly Thr Leu Pro Glu Leu Glu Leu Phe
340 345 350

Thr Asn Ile Val Asn Ser Trp Asp Ile Asn Ala Ile Asp Glu Leu Pro
355 360 365

Asp Tyr Leu Lys Ile Cys Phe Leu Ala Cys Tyr Asn Ala Thr Asn Glu
370 375 380

Leu Ser Tyr Asn Thr Leu Thr Asn Lys Gly Phe Phe Val His Pro Tyr
385 390 395 400

Leu Lys Lys Ala Trp Gln Asp Leu Cys Asn Ser Tyr Ile Ile Glu Ala
405 410 415

Lys Trp Phe Asn Asp Gly Tyr Thr Pro Thr Phe Asn Glu Phe Ile Glu
420 425 430

Asn Ala Tyr Met Ser Ile Gly Ile Ala Pro Ile Ile Arg His Ala Tyr
435 440 445

Leu Leu Thr Leu Thr Ser Val Thr Glu Glu Ala Leu Gln His Ile Glu
450 455 460

Arg Ala Glu Ser Met Ile Arg Asn Ala Cys Leu Ile Val Arg Leu Thr
465 470 475 480

Asn Asp Met Gly Thr Ser Ser Asp Glu Leu Glu Arg Gly Asp Ile Pro
485 490 495

Lys Ser Ile Gln Cys Tyr Met His Glu Ser Gly Ala Thr Glu Met Glu
500 505 510

Ala Arg Ala Tyr Ile Lys Gln Phe Ile Val Glu Thr Trp Lys Lys Leu
515 520 525

Asn Lys Glu Arg Gln Glu Ile Gly Ser Glu Phe Pro Gln Glu Phe Val
530 535 540

Asp Cys Val Ile Asn Leu Pro Arg Met Gly His Phe Met Tyr Thr Asp
545 550 555 560

Gly Asp Lys His Gly Lys Pro Asp Met Phe Lys Pro Tyr Val Phe Ser
565 570 575

Leu Phe Val Asn Pro Ile
580

<210> SEQ ID NO 21
<211> LENGTH: 1944
<212> TYPE: DNA
<213> ORGANISM: Artificial Sequence
<220> FEATURE:
<223> OTHER INFORMATION: NT sequence of DXS-IspH-IspF with first 22 AA of lambda Pr Cro promoter

<400> SEQUENCE: 21
atggaacaac gcataaccct gaaagattat gcaatgcgct ttgggcaaac caagacagct 60
aaagatccga gtttttttaaa gaagatgtcc attgagcaac tcgaggaact ctctgaagaa 120
attcgcaatt ttctcatcac cagtctcagc gcgtcgggag gacatattgg gccgaatctg 180
ggcgtggtcg aattaacaat tgccttgcac aaagaatttg acagccccaa agacaaattt 240
ctgtgggacg tcggccacca gtcgtatgtc cacaaattgc ttaccggccg tgggaaagaa 300
tttgaaactc tgcgccaata caaagggttg tgcgggttcc ctaaacgtag cgaaagtgaa 360
catgatgtgt gggaaacggg ccatagttcc acaagtttat ccggggcgat gggtatggct 420

-continued

```
gccgcccgag acattaaagg ctcgaaagaa tacatcatcc ccattattgg tgacggtgcg    480

ttaaccggcg gcatggcctt agaggcgctc aaccacattg gcgacgagaa gaaagatatg    540

atcgtgatcc tgaatgataa tgaaatgtcc atcgcgccca atgtcggagc tattcactcc    600

atgctggggc gccttcggac agcgggcaaa tatcaatggg tgaaagatga actggaatac    660

ttgtttaaac gcatcccggc tgttgggggc aaattggcgg cgaccgctga gcgtattaaa    720

gatagtctga agtacatgct cgtgtctgga atgtttttcg aagaactcgg ctttacctac    780

ctgggcccgg ttgatggcca ctcttatcac gaattgtttg aaaacctgca gtatgcaaag    840

aaaactaagg ggcccgtgct cttgcacgtc attaccaaga agggaaaggg ctataaaccc    900

gccgaaactg atacaattgg gacctggcat ggcaccggcc cctataagat taataccggg    960

gattttgtaa aacctaaagc agcagccccc agctggagcg ggctcgtttc tggcacggtt   1020

caagaattag cccgcgagga tgaccgtatt gtcgctatca ctcctgcgat gcctgtgggc   1080

tccaaattgg aggggtttgc caaagagttt ccggaacgta tgtttgatgt cggtatcgcc   1140

gaacaacatg cggccacgat ggccgccggt atggcgttgc aaggtatgaa accttttta   1200

gccatctaca gcacctttct ccagcgcgcc tatgatcagg tggtgcacga catttgtcgg   1260

cagaacgcca atgtatttat cgggattgat cgcgcaggcc tcgttggtgc tgatggagaa   1320

acccatcaag ggtatttga tattgctttc ttacgccata tccccaattt ggtcctgatg   1380

atgccgaagg atgagaacga aggtcggcac atggttaata ctgcactcaa ctacgaagaa   1440

ggtcccatcg ccatgcgctt tccacgcggt aacggtttgg gtgtcaaaat ggataaagaa   1500

ctcaagacga ttccaattgg cacgtgggaa gtgttacgtc caggcaaaga tgccgtgatt   1560

ttaacgttcg gtacgaccat tgaaatggct ctcgaagcgg ccgaagaatt acaaaaagaa   1620

ggtttgagtg ttcgggtagt taacgcgcgg ttcatcaaac ccatcgataa gcagatgatg   1680

aaagccattc ttaatgaggg tttacccatc ctcacgatcg aagaagcggt gctggagggt   1740

ggtttcggtt ctaccatcct cgaatatgca catgatctcg gcatgtatca caccccaatt   1800

gatcgaatgg ggattccgga tcggtttatt gaacatggtt cggtgacagc cctccttgag   1860

gaaatcgggc ttaccaaggc tgaagtgatg aatcggatta aacttcttat gccccccaag   1920

acccataaag gaattggttc ttaa                                          1944
```

```
<210> SEQ ID NO 22
<211> LENGTH: 647
<212> TYPE: PRT
<213> ORGANISM: Artificial Sequence
<220> FEATURE:
<223> OTHER INFORMATION: AA sequence of DXS-IspH-IspF with first 22 AA
      of lambda Pr Cro promoter

<400> SEQUENCE: 22

Met Glu Gln Arg Ile Thr Leu Lys Asp Tyr Ala Met Arg Phe Gly Gln
1               5                   10                  15

Thr Lys Thr Ala Lys Asp Pro Ser Phe Leu Lys Lys Met Ser Ile Glu
            20                  25                  30

Gln Leu Glu Glu Leu Ser Glu Glu Ile Arg Asn Phe Leu Ile Thr Ser
        35                  40                  45

Leu Ser Ala Ser Gly Gly His Ile Gly Pro Asn Leu Gly Val Val Glu
    50                  55                  60

Leu Thr Ile Ala Leu His Lys Glu Phe Asp Ser Pro Lys Asp Lys Phe
65                  70                  75                  80

Leu Trp Asp Val Gly His Gln Ser Tyr Val His Lys Leu Leu Thr Gly
```

-continued

```
                85                  90                  95

Arg Gly Lys Glu Phe Glu Thr Leu Arg Gln Tyr Lys Gly Leu Cys Gly
            100                 105                 110

Phe Pro Lys Arg Ser Glu Ser Glu His Asp Val Trp Glu Thr Gly His
        115                 120                 125

Ser Ser Thr Ser Leu Ser Gly Ala Met Gly Met Ala Ala Ala Arg Asp
    130                 135                 140

Ile Lys Gly Ser Lys Glu Tyr Ile Ile Pro Ile Ile Gly Asp Gly Ala
145                 150                 155                 160

Leu Thr Gly Gly Met Ala Leu Glu Ala Leu Asn His Ile Gly Asp Glu
                165                 170                 175

Lys Lys Asp Met Ile Val Ile Leu Asn Asp Asn Glu Met Ser Ile Ala
            180                 185                 190

Pro Asn Val Gly Ala Ile His Ser Met Leu Gly Arg Leu Arg Thr Ala
        195                 200                 205

Gly Lys Tyr Gln Trp Val Lys Asp Glu Leu Glu Tyr Leu Phe Lys Arg
    210                 215                 220

Ile Pro Ala Val Gly Gly Lys Leu Ala Ala Thr Ala Glu Arg Ile Lys
225                 230                 235                 240

Asp Ser Leu Lys Tyr Met Leu Val Ser Gly Met Phe Phe Glu Glu Leu
                245                 250                 255

Gly Phe Thr Tyr Leu Gly Pro Val Asp Gly His Ser Tyr His Glu Leu
            260                 265                 270

Phe Glu Asn Leu Gln Tyr Ala Lys Lys Thr Lys Gly Pro Val Leu Leu
        275                 280                 285

His Val Ile Thr Lys Lys Gly Lys Gly Tyr Lys Pro Ala Glu Thr Asp
    290                 295                 300

Thr Ile Gly Thr Trp His Gly Thr Gly Pro Tyr Lys Ile Asn Thr Gly
305                 310                 315                 320

Asp Phe Val Lys Pro Lys Ala Ala Ala Pro Ser Trp Ser Gly Leu Val
                325                 330                 335

Ser Gly Thr Val Gln Glu Leu Ala Arg Glu Asp Asp Arg Ile Val Ala
            340                 345                 350

Ile Thr Pro Ala Met Pro Val Gly Ser Lys Leu Glu Gly Phe Ala Lys
        355                 360                 365

Glu Phe Pro Glu Arg Met Phe Asp Val Gly Ile Ala Glu Gln His Ala
    370                 375                 380

Ala Thr Met Ala Ala Gly Met Ala Leu Gln Gly Met Lys Pro Phe Leu
385                 390                 395                 400

Ala Ile Tyr Ser Thr Phe Leu Gln Arg Ala Tyr Asp Gln Val Val His
                405                 410                 415

Asp Ile Cys Arg Gln Asn Ala Asn Val Phe Ile Gly Ile Asp Arg Ala
            420                 425                 430

Gly Leu Val Gly Ala Asp Gly Glu Thr His Gln Gly Val Phe Asp Ile
        435                 440                 445

Ala Phe Leu Arg His Ile Pro Asn Leu Val Leu Met Met Pro Lys Asp
    450                 455                 460

Glu Asn Glu Gly Arg His Met Val Asn Thr Ala Leu Asn Tyr Glu Glu
465                 470                 475                 480

Gly Pro Ile Ala Met Arg Phe Pro Arg Gly Asn Gly Leu Gly Val Lys
                485                 490                 495

Met Asp Lys Glu Leu Lys Thr Ile Pro Ile Gly Thr Trp Glu Val Leu
            500                 505                 510
```

```
Arg Pro Gly Lys Asp Ala Val Ile Leu Thr Phe Gly Thr Thr Ile Glu
        515                 520                 525

Met Ala Leu Glu Ala Ala Glu Glu Leu Gln Lys Glu Gly Leu Ser Val
    530                 535                 540

Arg Val Val Asn Ala Arg Phe Ile Lys Pro Ile Asp Lys Gln Met Met
545                 550                 555                 560

Lys Ala Ile Leu Asn Glu Gly Leu Pro Ile Leu Thr Ile Glu Glu Ala
                565                 570                 575

Val Leu Glu Gly Gly Phe Gly Ser Thr Ile Leu Glu Tyr Ala His Asp
            580                 585                 590

Leu Gly Met Tyr His Thr Pro Ile Asp Arg Met Gly Ile Pro Asp Arg
        595                 600                 605

Phe Ile Glu His Gly Ser Val Thr Ala Leu Leu Glu Glu Ile Gly Leu
    610                 615                 620

Thr Lys Ala Glu Val Met Asn Arg Ile Lys Leu Leu Met Pro Pro Lys
625                 630                 635                 640

Thr His Lys Gly Ile Gly Ser
                645


<210> SEQ ID NO 23
<211> LENGTH: 4565
<212> TYPE: DNA
<213> ORGANISM: Artificial Sequence
<220> FEATURE:
<223> OTHER INFORMATION: NTsequence of DXS-IspH-IspF with bacteriophage
      lambda promoter and thermolabile cI857 repressor

<400> SEQUENCE: 23

atgcatacag cccaacgacc ccgaaatttt gatggccctg ggttttgtcc attacctcaa     60

tgcagattac gaagccgcca atgatcgttg gtatgaagcc ttagcggcgg caacgaccca    120

ggatttcccc ccagccctcc aggcggagat ttatgcgggc ctggcgatta gtatgtacga    180

tttggcccaa aggcaaccca ccgacgttga ccaggaaatt cttgtaggga aagccgaaaa    240

actccgggcg atcgccctag atctcgatcg ttcccagctc aaccccgcc gcctcgaaca     300

aagttggtta tggttccctg aggcgatcgc cacttggcaa accctgctcg ctttagaaga    360

atctccctag gtcatatccg gggcatacat tcgatcaact tgagcgcaaa aatcttgcaa    420

accattacgg cttaagcacg agaccccctg atggggcgga cttgggggac aatggggtga    480

aataaatccc acgataataa ccctattgaa ttcaggagct agaactggtc agggctgggg    540

caatttttaa ttattgttac gcaggtcttg cctagggggg gggaggccgt attatcttct    600

agtgatgttt gctgaaaacg cctgaaggag aataacatat ggacctgtta agtattcaag    660

atccgagttt tttaaagaag atgtccattg agcaactcga ggaactctct gaagaaattc    720

gcaattttct catcaccagt ctcagcgcgt cgggaggaca tattgggccg aatctgggcg    780

tggtcgaatt aacaattgcc ttgcacaaag aatttgacag ccccaaagac aaatttctgt    840

gggacgtcgg ccaccagtcg tatgtccaca aattgcttac cggccgtggg aaagaatttg    900

aaactctgcg ccaatacaaa gggttgtgcg ggttccctaa acgtagcgaa agtgaacatg    960

atgtgtggga aacgggccat agttccacaa gtttatccgg ggcgatgggt atggctgccg   1020

cccgagacat taaaggctcg aaagaataca tcatccccat tattggtgac ggtgcgttaa   1080

ccggcggcat ggccttagag gcgctcaacc acattggcga cgagaagaaa gatatgatcg   1140

tgatcctgaa tgataatgaa atgtccatcg cgcccaatgt cggagctatt cactccatgc   1200
```

-continued

```
tggggcgcct tcggacagcg ggcaaatatc aatgggtgaa agatgaactg gaatacttgt   1260
ttaaacgcat cccggctgtt gggggcaaat tggcggcgac cgctgagcgt attaaagata   1320
gtctgaagta catgctcgtg tctggaatgt ttttcgaaga actcggcttt acctacctgg   1380
gcccggttga tggccactct tatcacgaat tgtttgaaaa cctgcagtat gcaaagaaaa   1440
ctaaggggcc cgtgctcttg cacgtcatta ccaagaaggg aaagggctat aaacccgccg   1500
aaactgatac aattgggacc tggcatggca ccggcccccta taagattaat accggggatt   1560
ttgtaaaacc taaagcagca gcccccagct ggagcgggct cgtttctggc acggttcaag   1620
aattagcccg cgaggatgac cgtattgtcg ctatcactcc tgcgatgcct gtgggctcca   1680
aattggaggg gtttgccaaa gagtttccgg aacgtatgtt tgatgtcggt atcgccgaac   1740
aacatgcggc cacgatggcc gccggtatgg cgttgcaagg tatgaaacct tttttagcca   1800
tctacagcac ctttctccag cgcgcctatg atcaggtggt gcacgacatt tgtcggcaga   1860
acgccaatgt atttatcggg attgatcgcg caggcctcgt tggtgctgat ggagaaaccc   1920
atcaaggggt atttgatatt gctttcttac gccatatccc caatttggtc ctgatgatgc   1980
cgaaggatga gaacgaaggt cggcacatgg ttaatactgc actcaactac gaagaaggtc   2040
ccatcgccat gcgctttcca cgcggtaacg gtttgggtgt caaaatggat aaagaactca   2100
agacgattcc aattggcacg tgggaagtgt tacgtccagg caaagatgcc gtgattttaa   2160
cgttcggtac gaccattgaa atggctctcg aagcggccga agaattacaa aaagaaggtt   2220
tgagtgttcg ggtagttaac gcgcggttca tcaaacccat cgataagcag atgatgaaag   2280
ccattcttaa tgagggttta cccatcctca cgatcgaaga agcggtgctg gagggtggtt   2340
tcggttctac catcctcgaa tatgcacatg atctcggcat gtatcacacc ccaattgatc   2400
gaatggggat tccggatcgg tttattgaac atggttcggt gacagccctc cttgaggaaa   2460
tcgggcttac caaggctgaa gtgatgaatc ggattaaact tcttatgccc cccaagaccc   2520
ataaaggaat tggttcttaa ggtaccaagg agatatacca tggatgttat taagattagc   2580
cctcgcggtt attgttacgg tgtggtcgat gcgatggtta ttgccaaaaa cgcgtctctg   2640
gacaaaacct tgccccgccc gatttatatt ctgggcatga tcgtgcacaa caagcacgtt   2700
acagatgcct tcgaggaaga tgggatttat actcttgatg gcaccaaccg actcgagatt   2760
ctcaaacagg tggaaaaggg gaccgtaatt tttaccgctc acggcgtaag tcctgaagtg   2820
cgtaaagcgg ccgaggagaa aggtttagtc actatcgatg ctacctgtcc cgatgtgacc   2880
aagacgcatg atttgatccg gaaagtcaaa gccgaaggct atcacgtcat ctatatcggg   2940
aaaaagggtc atccagaacc agaaggagca gttggtgtgg cccccgaaat cgtgcattta   3000
gtcgaaaccg aagaagatgt gcggaatctg gacatccaag ccgaaaaact gatcgtgact   3060
aatcaaacga ccatgagtca gtgggatgtg catgacatca tggaatccgt caaagaaaaa   3120
taccccctatg tggaatacca ccaagagatt tgcctcgcga cccaagtccg gcaagaagct   3180
gtttctgaac aggcgaagaa agcagatctc acgattgttg ttggtgaccc caaatcgaat   3240
aacagcaatc gtctggctca agtgtccgaa gaaattgcgg gcaccaaagc ctaccgcatt   3300
ggcgacatca gtgaattgaa attggaatgg cttaaggatg taaatacagt ggcggtaaca   3360
gcaggagcct cgaccccgac gcccattacg aaggaagtca ttcgctttct cgagcagttt   3420
gatcacaatg acgaatccac ctggcagtta gagcatagcg tccccctcaa gaagattttg   3480
ccgaaagtta aaatcaaaaa ttaagtcgac aaggagatac tagtatgttt cgtatcggcc   3540
agggttttga cgttcaccag ttaacggaag gtcgcccact cattattggt ggcatcgaaa   3600
```

```
ttccgtatga aaaagggttg ctgggccata gtgatgccga tgtactgtta cacacggtgg    3660

ccgatgcgtg cttaggcgct gcaggcgaag gagacatcgg taaacatttt cctgacactg    3720

atcccgagtt caaggatgcc gactccttca agctccttca gcacgtgtgg aacatcgtca    3780

aagagaaagg atacgtcctc gggaatattg attgtaccat cattgccag aaacccaaaa     3840

tggcccccca tatcgatgcg atgcggaagc gaattgccga aggcctcgaa gctgatgtga    3900

gccaagttaa tgtgaaggct accaccacgg aaaaattggg gtttaccggg cgtgcggaag    3960

gcattgcagc ccaagccacc gtcctcattc aaaaagcgta aggatccaaa aagcgcagct    4020

gaaatagctg cgcttttttt gttttgtcat aatctagacc ccccattctc ccttgaggga    4080

gatgtccaga ggggagtcag taaattccaa agacaaaact gattccccct tttaaacaca    4140

ggcctaggtt tgactttagt tcgtttcaat gaaggcgaaa cgcccctgtt gacccgattc    4200

atccatttca atttgggcca caaaaaattc cttctggaca atttcccctt cctctgtgaa    4260

ggaaatttca cccaaaggcg tgacgtaggg acctgcaaaa atttcgtccc gcagttgtcg    4320

tcgcaagtcc ggtagagcaa gagtttctaa gggcgttttt tcatcgaggc tgctgagggc    4380

ttcaacaaaa acttggatcg ccgtaaaagc ctgggcacta aattggggcg gctctttttg    4440

gttttgttga aaataggcgt cccgaaacgc gcggttaatc tcattatcta actcggcact    4500

gtaggcttgg gccaccaaca ccccatcaca ttttgcttgg cagacgggga aaatattagg    4560

catgc                                                                4565
```